(12) United States Patent
Leonard et al.

(10) Patent No.: US 11,116,851 B2
(45) Date of Patent: Sep. 14, 2021

(54) ANTI-CANCER AND ANTI-INFLAMMATORY THERAPEUTICS AND METHODS THEREOF

(71) Applicant: University of Massachusetts, Boston, MA (US)

(72) Inventors: Jack L. Leonard, Shrewsbury, MA (US); Karl J. Simin, Princeton, MA (US); Deborah M. Leonard, Shrewsbury, MA (US)

(73) Assignee: University of Massachusetts, Boston, MA (US)

( * ) Notice: Subject to any disclaimer, the term of this patent is extended or adjusted under 35 U.S.C. 154(b) by 367 days.

(21) Appl. No.: 15/765,431

(22) PCT Filed: Oct. 18, 2016

(86) PCT No.: PCT/US2016/057491
§ 371 (c)(1),
(2) Date: Apr. 2, 2018

(87) PCT Pub. No.: WO2017/070092
PCT Pub. Date: Apr. 27, 2017

(65) Prior Publication Data
US 2018/0272001 A1 Sep. 27, 2018

Related U.S. Application Data

(60) Provisional application No. 62/243,612, filed on Oct. 19, 2015, provisional application No. 62/281,702, filed on Jan. 21, 2016, provisional application No. 62/380,525, filed on Aug. 29, 2016.

(51) Int. Cl.
| | |
|---|---|
| *A61K 48/00* | (2006.01) |
| *C07K 14/47* | (2006.01) |
| *A01K 67/027* | (2006.01) |
| *A61K 33/243* | (2019.01) |
| *A61P 35/00* | (2006.01) |
| *C12N 15/86* | (2006.01) |
| *A61K 31/337* | (2006.01) |
| *A61K 31/351* | (2006.01) |

(52) U.S. Cl.
CPC ........ *A61K 48/005* (2013.01); *A01K 67/0275* (2013.01); *A61K 33/243* (2019.01); *A61P 35/00* (2018.01); *C07K 14/4703* (2013.01); *A01K 2217/072* (2013.01); *A01K 2227/105* (2013.01); *A01K 2267/0331* (2013.01); *A61K 31/337* (2013.01); *A61K 31/351* (2013.01); *A61K 2300/00* (2013.01); *C12N 15/86* (2013.01)

(58) Field of Classification Search
None
See application file for complete search history.

(56) References Cited

U.S. PATENT DOCUMENTS

| | | | | |
|---|---|---|---|---|
| 7,057,017 | B2 * | 6/2006 | McCarthy | C07K 14/47 530/300 |
| 7,767,642 | B2 | 8/2010 | Schroeder | |
| 8,618,273 | B2 | 12/2013 | Kumon et al. | |
| 8,658,611 | B2 | 2/2014 | Kumon et al. | |
| 2004/0014209 | A1* | 1/2004 | Lassar | C12N 5/0657 435/366 |
| 2006/0269921 | A1 | 11/2006 | Segara et al. | |
| 2009/0215690 | A1* | 8/2009 | Mercola | A61P 35/00 514/1.1 |
| 2011/0166545 | A1* | 7/2011 | Kumon | C07K 14/4747 604/500 |
| 2013/0031118 | A1 | 1/2013 | Takamura et al. | |
| 2013/0171235 | A1* | 7/2013 | Parsons | A61P 3/00 424/450 |
| 2014/0107189 | A1 | 4/2014 | Bancel et al. | |
| 2014/0147432 | A1 | 5/2014 | Bancel et al. | |
| 2015/0283178 | A1 | 10/2015 | June et al. | |

FOREIGN PATENT DOCUMENTS

| | | |
|---|---|---|
| CN | 103080309 | 5/2013 |
| CN | 103667492 | 3/2014 |
| CN | 104017083 | 9/2014 |
| CN | 104662037 | 5/2015 |

(Continued)

OTHER PUBLICATIONS

Abarzua et al. An N-Terminal 78 Amino Acid Tr, 614-uncation of REIC/Dkk-3 Effectively Induces Apoptosis. Biocehmical and Biophysical Research Communications, 2008; 614-618.*
Brottand Sokol. Regulation of Wnt/LRP Signaling by Distinct Domains of Dickkopf Proteins. Molecular and Cellular Biology, 2002. 22(17):6100-6110.*
Coupade et al. Novel Human-Derived Cell-Penetrating Peptides for Specific Subcellular Delivery of Therapeutic Biomolecules. Biochemistry Journal, 2005. 390:407-418.*
Barash et al. Human Secretory Signal Peptide Description By Hidden Markov Model and Generation of a Strong Artificial Signal Peptide for Secreted protein Expression. Biochemical and Biophysical Research Communications, 2002. 294:835-842.*
EP Office Action in European Appln. No. 16858059.5, dated Jul. 20, 2020, 4 pages.

(Continued)

*Primary Examiner* — James D Schultz
*Assistant Examiner* — Kimberly A Aron
(74) *Attorney, Agent, or Firm* — Fish & Richardson P.C.

(57) ABSTRACT

The invention relates to the discovery of a vital new component of the Wnt pathway that regulates trafficking of β-catenin to the cell nucleus and novel therapeutic approaches to cancer treatment. Disclosed herein is a previously unknown, essential component of the Wnt/β-catenin signaling pathway that governs the quantity of β-catenin delivered to the cell nucleus. This intracellular inhibitor of β-catenin signaling (IBS) is transcribed from a second transcriptional start site adjacent to exon 3 of the Dkk3 gene and is required for early mouse development. IBS captures β-catenin destined for the nucleus in a complex with β-TrCP that is bound to the actin cytoskeleton and unavailable for nuclear translocation.

20 Claims, 24 Drawing Sheets

Specification includes a Sequence Listing.

(56) References Cited

FOREIGN PATENT DOCUMENTS

| EP | 2589658 | 5/2013 | | |
|---|---|---|---|---|
| JP | 2008-536873 A | 9/2008 | | |
| JP | 2009-114103 | 5/2009 | | |
| WO | WO 2003106657 | 12/2003 | | |
| WO | WO2012/002582 | 1/2012 | | |
| WO | WO2012/079000 | 6/2012 | | |
| WO | WO2013/148224 | 10/2013 | | |
| WO | WO-2014005219 A1 | * | 1/2014 | ....... C07K 14/43504 |
| WO | WO2015/048331 | 4/2015 | | |

OTHER PUBLICATIONS

Farwell, A.P., et al., "Identification of a 27-kDa Protein with the Properties of Type II Iodothyronine 5'-Deiodinase in Dibutyryl Cyclic AMP-Stimulated Glial Cells*," The Journal of Biological Chemistry, vol. 264(34), pp. 20561-20567 (1989).

Leonard, D., et al., "Cloning, Expression, and Functional Characterization of the Substrate Binding Subunit of Rat Type II Iodothyronine 5'-Deiodinase*," The Journal of Biological Chemistry, vol. 275(33); pp. 25194-25201 (2000).

Leonard, J., et al., "The Dkk3 Gene Encodes a Vital Intracellular Regulator of Cell Proliferation," PLOS One 12(7): e0181724, pp. 1-27 (2017).

Marciniak, R.A., et al., "HIV-1 Tat Protein Trans-Activates Transcription in Vitro," Cell, vol. 63, pp. 791-802 (1990).

Green, M., et al., "Autonomous Functional Domains of Chemically Synthesized Human Immunodeficiency Virus Tat Trans-Activator Protein," Cell, vol. 55, pp. 1179-1188 (1988).

Vives, E., et al., "A Truncated HIV-1 Tat Protein Basic Domain Rapidly Translocates Through the Plasma Membrane and Accumulates in the Cell Nucleus*," The Journal of Biological Chemistry, vol. 272(25): pp. 16010-16017 (1997).

Milletti, F., "Cell-Penetrating Peptides: Classes, Origin, and Current Landscape," Drug Discovery Today, vol. 17(15/16) 2012.

Ho, A., et al., "Synthetic Protein Transduction Domains: Enhanced Transduction Potential in Vitro and in Vivo," Cancer Research 61, pp. 474-477 (2001).

Guidotti, G., et al., "Cell-Penetrating Peptides: from Basic Research to Clinics," Trends in Pharmacological Sciences, vol. 38(4): pp. 406-424 (2017).

Krupnik, V.E., et al., "Functional and Structural Diversity of the Human Dickkopf Gene Family," Gene 238; pp. 301-313 (1999).

Wadia, J.S., et al., Protein Transduction Technology, Current Opinion in Biotechnology, 13: pp. 52-56 (2002).

Kobayashi, K., et al., "Reduced Expression of the REIC/Dkk-3 Gene by Promotor-Hypermethylation in Human Tumor Cells," Gene 282: pp. 151-158 (2002).

Anson et al., "Oncogenic β-catenin triggers an inflammatory response that determines the aggressiveness of hepatocellular carcinoma in mice," The Journal of clinical investigation, Feb. 1, 2012, 122(2):586-99.

JP Office Action in Japanese Appln. No. 2018-539251, dated Jul. 28, 2020, 10 pages (with English translation).

IL Office Action in Israeli Appln. No. 258771, dated Feb. 19, 2020, 9 pages (with English Translation).

Abarzua et al, "Adenovirus-Mediated Overexpression of REIC/Dkk-3 Selectively Induces Apoptosis in Human Prostate Cancer Cells through Activation of c-Jun-NH2-Kinase," Cancer Res., 2005, 65:9617-9622.

Alm et al, "Structural Basis of Wnt Signaling Inhibition by Dickkopf Binding to LRP5/6," Developmental Cell, 2011, 21:862-873.

Barrantes et al, "Generation and Characterization of dickkopf3 Mutant Mice," Mol Cell Biol, 2006, 26:2317-2326.

Cheng et al, "Crystal structures of the extracellular domain of LRP6 and its complex with DKK1," Nature Structural & Molecular Biology, 2011, 18:1204-1210.

Chia et al, "Both the RGS Domain and the Six C-Terminal Amino Acids of Mouse Axin are Required for Normal Embryogenesis," Genetics, 2009, 181:1359-1368.

Edamura et al, "Adenovirus-mediated REIC/Dkk-3 gene transfer inhibits tumor growth and metastasis in an orthotopic prostate cancer model," Cancer Gene. Ther., 2007, 14:765-772.

EP Supplementary European Search Report in European Appln. No. EP16858059, dated Feb. 18, 2019, 8 pages.

Fedders et al, "A Dickkopf-3-related gene is expressed in differentiating nematocytes in the basal metazoan Hydra," Development Genes and Evolution, 2004, 214:72-80.

Fine et al, "An online bioinformatics tool predicts zinc finger and TALE nuclease off-target cleavage," Nucleic Acids Research, 2014, 13 pages.

Fong et al, "BET inhibitor resistance emerges from leukaemia stem cells," Nature, 2015, 525(7570):538-542.

Frescas et al, "Deregulated proteolysis by the F-box proteins SKP2 and β-TrCP: tipping the scales of cancer," Nature Reviews Cancer, 2008, 8:6:438-449.

Fujii et al, "Molecular Simulation Analysis of the Structure Complex of C2 Domains of DKK Family Members and β-propeller Domains of LRP5/6: Explaining Why DKK3 Does Not Bind to LRP5/6," Acta Med Okayama, 2014, 68:63-78.

Gotze et al, "Frequent promoter hypermethylation of Wnt pathway inhibitor genes in malignant astrocytic gliomas," Int. J. Cancer, 2009, 126:2584-2593.

Gu et al, "Dickkopf3 overexpression inhibits pancreatic cancer cell growth in vitro," World J Gastroenterol, 2017, 17:3810-3817.

Guardavaccaro et al, "Control of Meiotic and Mitotic Progression by the F Box Protein β-Trcp1 in Vivo," Developmental Cell, 2003, 4:799-812.

Guder et al, "An ancient Wnt-Dickkopf antagonism in Hydra," Development, 2006, 133:901-911.

Gupta et al, "An optimized two-finger archive for ZFN-mediated gene targeting," Nature Methods, 2012, 9:(6):588-590.

Hayashi et al, "Efficient gene modulation in mouse epiblast using a Sox2Cre transgenic mouse strain," Mechanisms of Development, 2002, S97-S101.

Hayashi et al, "Maternal Inheritance of Cre Activity in a Sox2Cre Deleter Strain," Genesis, 2003, 37:51-53.

Hopkins et al, "A Secreted PTEN Phosphatase that Enters Cells to Alter Signaling and Survival," 2013, Science, 341:399-402.

Hsieh et al, "Dickkopf-3/REIC functions as a suppressor gene of tumor growth," Oncogene, 2004, 23:9183-9189.

Jamora et al, "Links between signal transduction, transcription and adhesion in epithelial bud development," Nature, 2003, 422:317-322.

Kawano & Kypta, "Secreted antagonists of the Wnt signalling pathway," Journal of Cell Science, 2003, 116:2627-2634.

Kawasaki et al, "REIC/Dkk-3 overexpression downregulates P-glycoprotein in multidrugresistant MCF7/ADR cells and induces apoptosis in breast cancer," Cancer Gene. Ther., 2009, 16:65-72.

Kerkela et al, "Deletion of GSK-3b in mice leads to hypertrophic cardiomyopathy secondary to cardiomyoblast hyperproliferation," The Journal of Clinical Investigation, 2008, 118:3609-3618.

Krupnik et al, "Functional and structural diversity of the human Dickkopf gene family," Gene, 1999, 238:301-313.

Lee et al, "Dkk3, downregulated in cervical cancer, functions as a negative regulator of b-catenin," Int J Cancer, 2009, 124:287-297.

Leonard et al, "Cloning, Expression, and Functional Characterization of the Substrate Binding Subunit of Rat Type II Iodothyronine 5*-Deiodinase," J Biol Chem, 2000, 275:25194-25201.

Lewis et al, "Dkk1 and Wnt3 interact to control head morphogenesis in the mouse," Development, 2008, 135:1791-1801.

Li et al, "Bcl-2 overexpression in PhIP-induced colon tumors: cloning of the rat Bcl-2 promoter and characterization of a pathway involving b-catenin, c-Myc and E2F1," Oncogene, 2007, 26:6194-6202.

Li et al, "Dkk2 has a role in terminal osteoblast differentiation and mineralized matrix formation," Nature Genetics, 2005, 37:945-952.

Lodygin et al, "Functional Epigenomics Identifies Genes Frequently Silenced in Prostate Cancer," Cancer Res., 2005, 65(10):4218-4227.

(56) References Cited

OTHER PUBLICATIONS

Low et al, "A systems-wide screen identifies substrates of the SCFbTrCP ubiquitin ligase," Sci. Signal., 2014, 16:7(356).
Maniatis, "A ubiquitin ligase complex essential for the NF-kB, Wnt/Wingless, and Hedgehog signaling pathways," Genes & Development, 1999, 13:505-510.
Mao & Niehrs, "Kremen2 modulates Dickkopf2 activity during Wnt/LRP6 signaling," Gene, 2003, 302:179-183.
Miyamoto, et al,"RNA-Seq of Single Prostate CTCs Implicates Noncanonical Wnt Signaling in Antiandrogen Resistance," Science, 2015, 349:(6254):1351-6.
Monaghan et al, "Dickkopf genes are co-ordinately expressed in mesodermal lineages," Mech. Dev., 1999, 87:45-56.
Mukhopadhyay et al, "Dkk2 plays an essential role in the corneal fate of the ocular surface epithelium," Development, 2006, 133:2149-2154.
Nakayama et al, "Impaired degradation of inhibitory subunit of NF-B (I B) and -catenin as a result of targeted disruption of the β-TrCP1 gene," Proc. Natl. Acad. Sci. USA, 2003, 100:8752-8757.
Nicolaou et al, "Calicheamicin θ: A Rationally Designed Molecule with Extremely Potent and Selective DNA Cleaving Properties and Apoptosis Inducing Activity," Angew. Chem. Intl. Ed. Engl., 1994, 33:183-186.
Niehrs, "Function and biological roles of the Dickkopf family of Wnt modulators," Oncogene, 2006, 25:7469-7481.
PCT International Preliminary Report on Patentability in International Appln. No. PCT/US2016/057491, dated Mar. 27, 2017, 8 pages.
PCT International Search Report and Written Opinion in International Appln. No. PCT/US2016/057491, dated Mar. 27, 2017, 12 pages.
Roman-Gomez et al, "Transcriptional silencing of the Dickkopfs-3 (Dkk-3) gene by CpG hypermethylation in acute lymphoblastic leukaemia," Br J Cancer, 2004, 91:4:707-713.
Sato et al, "Frequent epigenetic inactivation of DICKKOPF family genes in human gastrointestinal tumors ," Carcinogenesis, 2007, 28:2459-2466.
Schwarze et al, "In Vivo Protein Transduction: Delivery of a Biologically Active Protein into the Mouse," Science, 1999, 285(5433):1569-1572.
Selib et al, "Loss of Dickkopf-1 Restores Neurogenesis in Old Age and Counteracts Cognitive Decline," Cell stem cell, 2013, 12:204-214.
Sieber et al, "Myh Deficiency Enhances Intestinal Tumorigenesis in Multiple Intestinal Neoplasia (ApcMin/ ) Mice," Cancer Res, 2004, 64:8876-8881.
Stachelek et al, "Myosin V Plays an Essential Role in the Thyroid Hormone-dependent Endocytosis of Type II Iodothyronine 5*'-Deiodinase," 2000, J. Biol. Chem., 275:31701-31707.
Stachelek et al, "Real-time Visualization of Processive Myosin 5a-mediated Vesicle Movement in Living Astrocytes," J. Biol. Chem., 2001, 276:35652-35659.
Tsuji et al, "A REIC Gene Shows Down-Regulation in Human Immortalized Cells and Human Tumor-Derived Cell Lines," Biochem. Biophys. Res. Commun., 2000, 268:20-24.
Veeck & Dahl, "Targeting the Wnt pathway in cancer: The emerging role of Dickkopf-3," Biochim. Biophys. Acta., 2011, 1825:18-28.
Wu et al, "Mutual antagonism between dickkopf1 and dickkopf2 regulates Wnt/β-catenin signalling," Current Biology, 2000, 10:24:1611-1614.
Xiang et al, "Epigenetic silencing of the WNT antagonist Dickkopf 3 disrupts normal Wnt/b-catenin signalling and apoptosis regulation in breast cancer cells," Journal of Cellular and Molecular Medicine, 2013, 17:1236-1246.
Xie et al, "Generation of Axin1 Conditional Mutant Mice," Genesis, 2011, 49:98-102.
Yue et al, "Downregulation of Dkk3 activates β-catenin/TCF-4 signaling in lung cancer," Carcinogenesis, 2008, 29:84-92.
Zorn, "Wnt signaling: Antagonistic Dickkopfs," Current Biology, 2001, R592-595.
JP Japanese Office Action in Japanese Appln. No. 2018-539251, dated Mar. 9, 2021, 5 pages (with English translation).
Abarzua et al., "N-terminal 78 amino acid truncation of REIC/Dkk-3 effectively induces apoptosis," Biochemical and Biophysical Research Communications, Oct. 31, 2008, 375(4):614-8.
CN Office Action in Chinese Appln. No. 201680074116.7, dated May 7, 2021, 16 pages (with English translation).

* cited by examiner

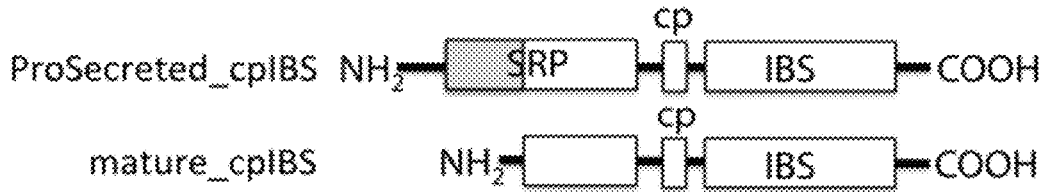

FIG. 1. Organization of functional domains of the secreted, cell penetrating IBS molecules. The ProSecreted_cpIBS is the pro form of the translation product prior to proteolytic cleavage of the membrane spanning residues recognized by the SRP (shown in grey). The mature _cpIBS is composed of the variable residues retained after release of the membrane spanning SRP residues, the cell penetrating domain (cp) and variable domains of IBS.

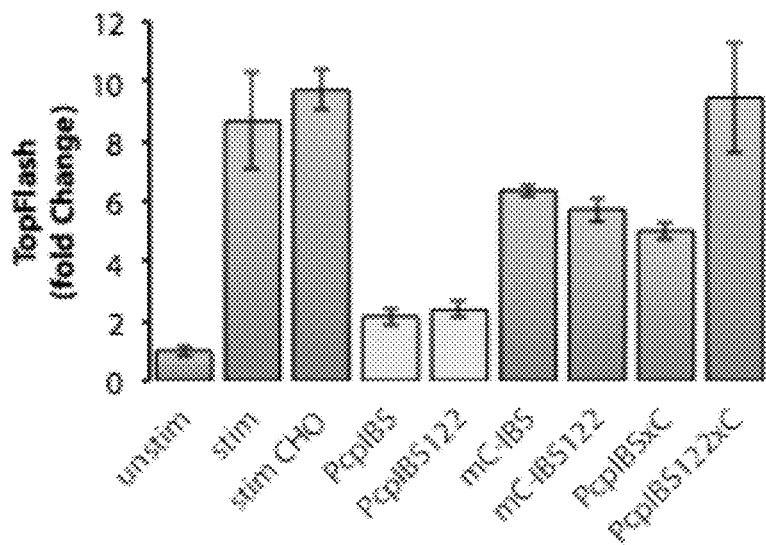

FIG. 2. β-catenin Signaling in presence of different spent media from CHO cells harboring different PTEN_cp_IBS variants. Data are the means +/- SE of triplicate wells.

FIG. 3. Schematic map of secreted ScpIBS mutants. SRP, signal recognition particle domain; cp, cell penetrating domain; N-1, required N-terminal amino acids 1-10; C-1, cysteine rich domain 1; C-2, cysteine rich domain 2; Ct, required C-terminus amino acids 270-280.

FIG. 4. Schematic of functional domains of the bacterial expressed unfolded, cell penetrating IBS molecules. The cpIBS is a fusion protein of an 11 residue long synthetic cp domain to the coding sequence of human IBS. The cpIBS$^{122}$ is composed of residues 1-122 of IBS with residues 270-280 appended to the C-terminus.

FIG. 5. Schematic map of secreted ScpIBS mutants. cp, cell penetrating domain; *N-1*, required N-terminal amino acids 1-10; C-1, cysteine rich domain 1; C-2, cysteine rich domain 2; *Ct*, required C-terminus amino acids 270-280.

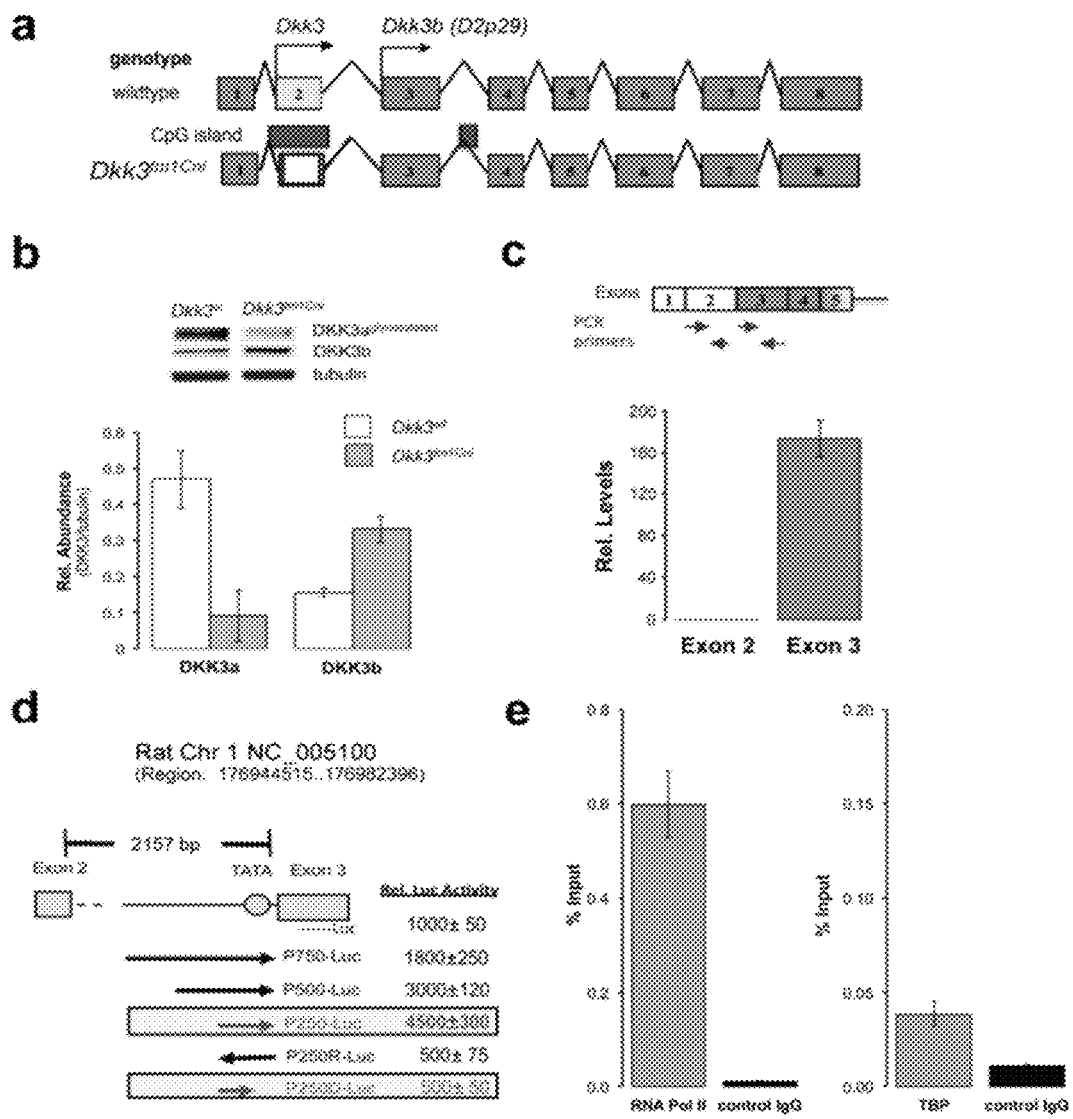

FIG. 6. Identification of multiple transcripts originating for the *Dkk3* gene locus. a. Schematic diagram of the *Dkk3* gene (NC_000073.6) in the wild type and *Dkk3$^{tm1Cni}$* mutant mouse. Initiator methionine for *Dkk3* (NM_0154814) and *D2p29* (AF245040) indicated by arrows. b. Immunoblot analysis of DKK3 isoforms in the brain of *Dkk3$^{+/+}$* and *Dkk3$^{tm1Cni}$* mouse. c. Quantitative PCR analysis *Dkk3* containing exon2 and exon 3 transcripts in total brain RNA in wild type and *Dkk3$^{tm1Cni}$*. Arrows indicate PCR primer sites (Error bars represent SE of three individuals). d. Schematic diagram of rat *Dkk3* intron 2:luciferase constructs used for promoter localization. Arrows show the orientation and location of intron 2 segments upstream of exon 3 (Error bars represent SE of three independent experiments). e. Chromatin immunoprecipitation of RNA pol 2 and TBP bound to the ~130 nt of intron 2 adjacent to exon 3 in the rat astrocyte *Dkk3* gene (Error bars represent the SE of three independent experiments).

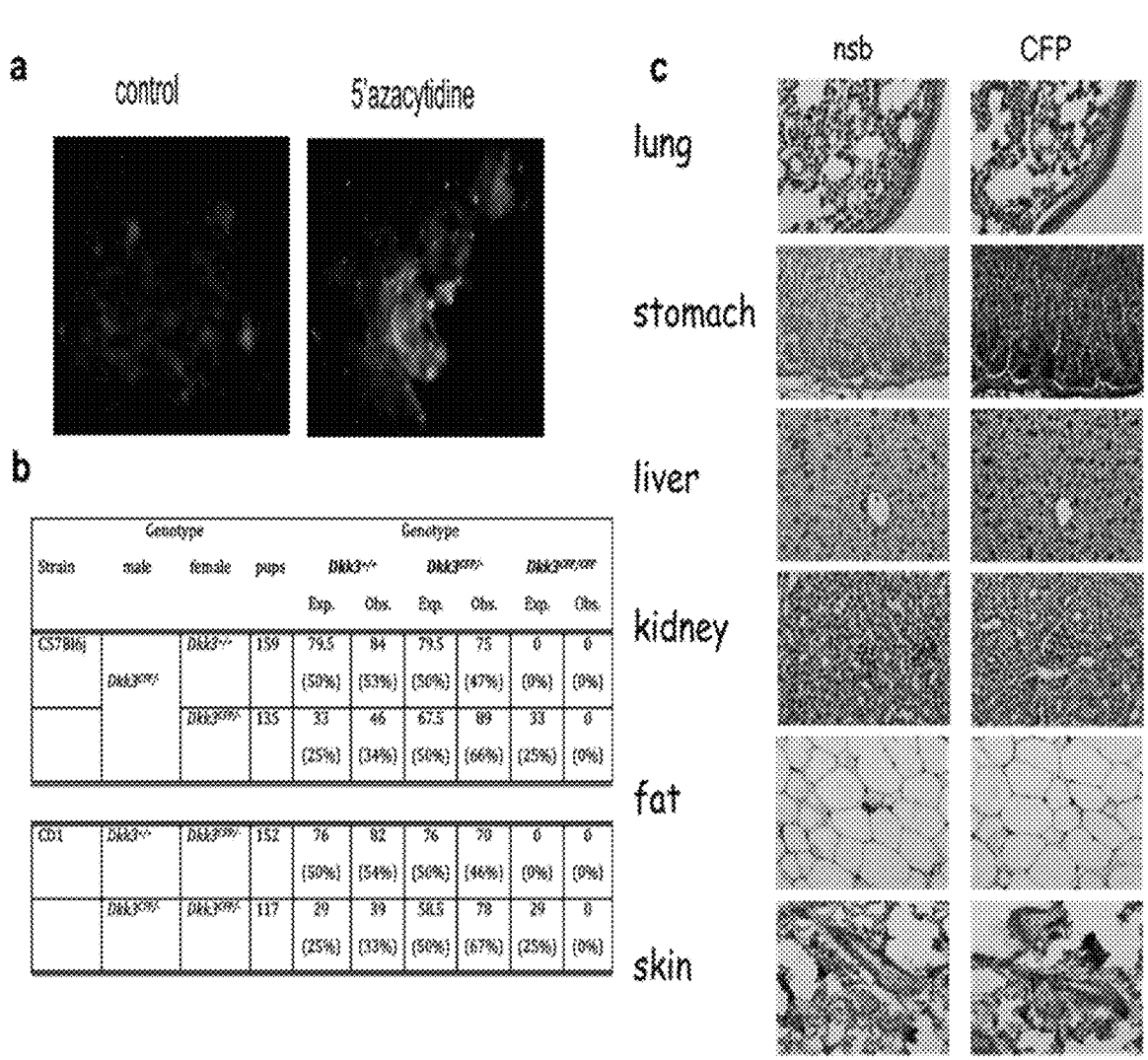
FIG. 7. Analysis of the biology of the TSS2 in the *Dkk3* gene of the ZFN gene-edited *Dkk3*$^{CFP/+}$ mouse. a. DNA methyltransferase inhibition increases TSS2-driven CFP in gene-edited cells. b. Phenotype ratios for the *Dkk3*$^{CFP}$ allele in C57Bl6j and out-bred CD1 mice. c. TSS2-driven CFP expression in representative tissues of the *Dkk3*$^{CFP/+}$ mouse.

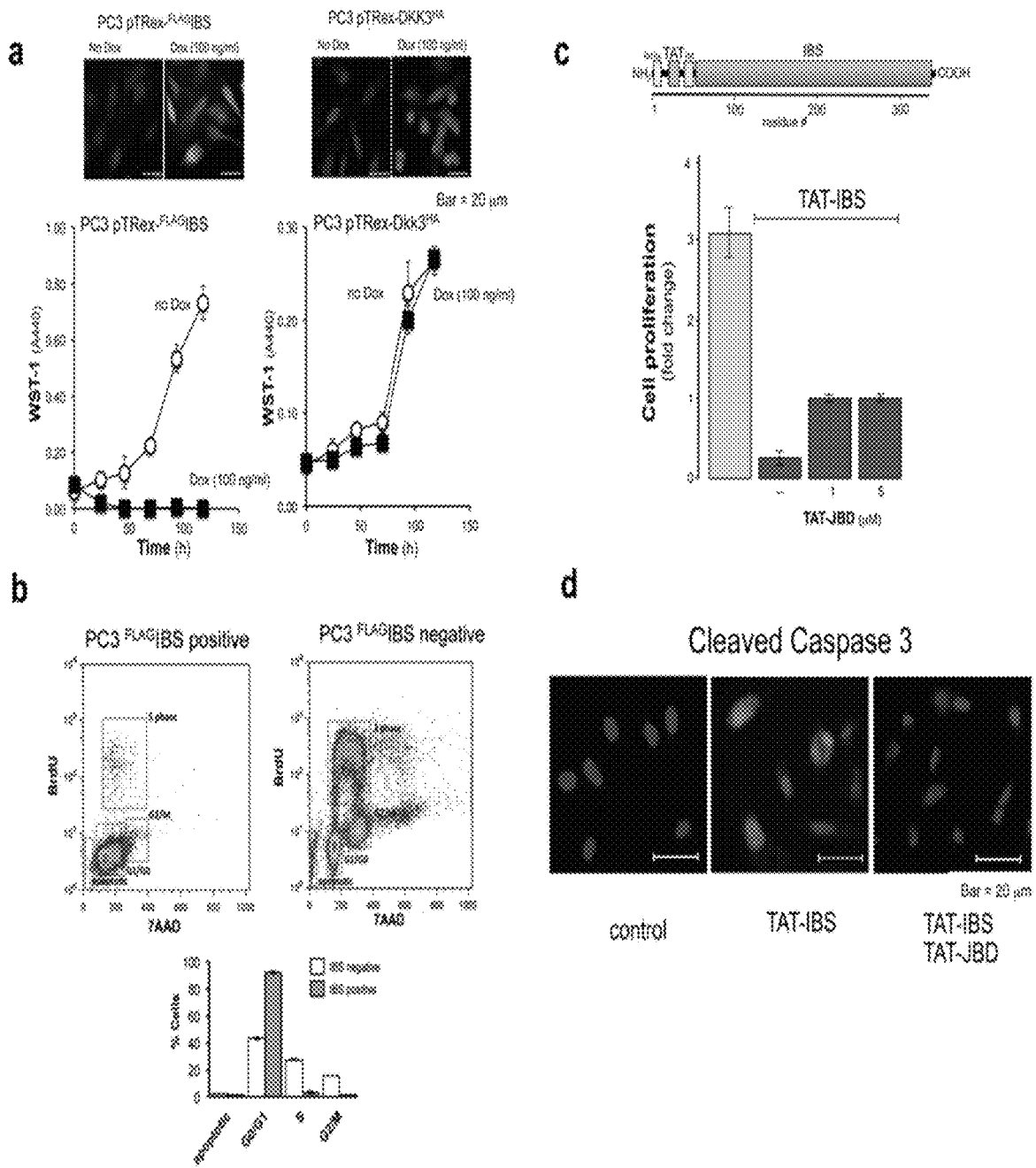

FIG. 8. IBS regulation of cell proliferation and apoptosis. a. Comparison of the effects of IBS and DKK3 on PC3 cell proliferation (Error bars represent the SE of three independent experiments). b. IBS arrests cell proliferation at the G0/G1 phase of the cell cycle (Error bars represent the SE of three independent experiments). c. Cell permeant IBS (TAT-IBS) initiated cell loss is blocked by inhibition of JNK activity and is independent of cell cycle arrest (Error bars represent the SE of three independent experiments). d. TAT-IBS induced pro-apoptotic Cleaved Caspase 3 by activation of the JNK pathway in PC3 cells.

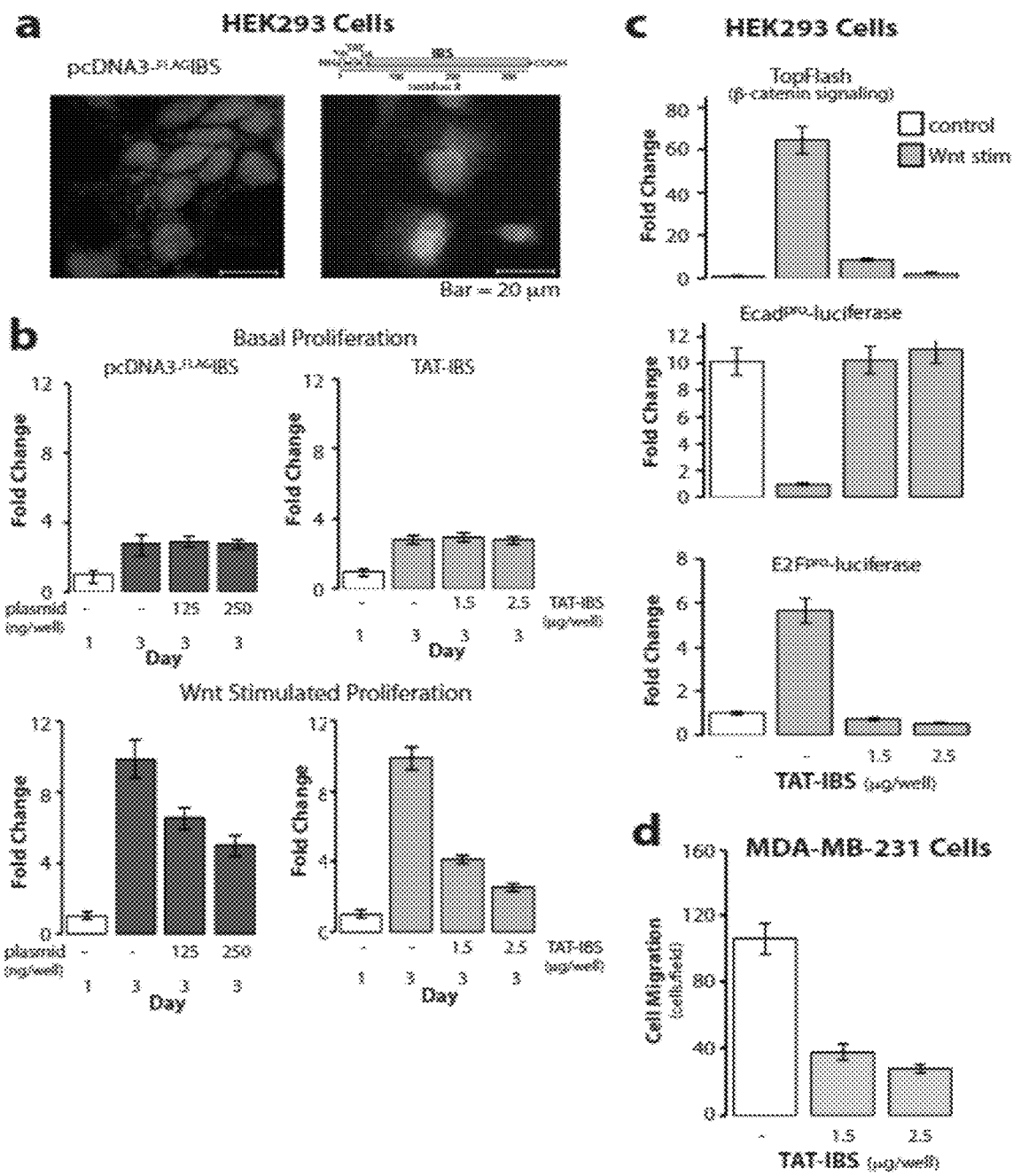

FIG. 9. IBS and β-catenin signaling. a. Comparison of the cellular distribution of TAT-IBS and transfected Flag-IBS in HEK293 cells. b. IBS blocks Wnt/β-catenin stimulated cell proliferation without altering basal cell proliferation (Data represent the means of four closely agreeing (±10%) independent experiments) Open bar – day 0; colored bars – day 3. c. TAT-IBS antagonizes primary and secondary β-catenin dependent gene expression (Error bars represent the SE of three independent experiments). d. TAT-IBS inhibits β-catenin dependent malignant cell migration (Error bars represent the SE of three independent experiments).

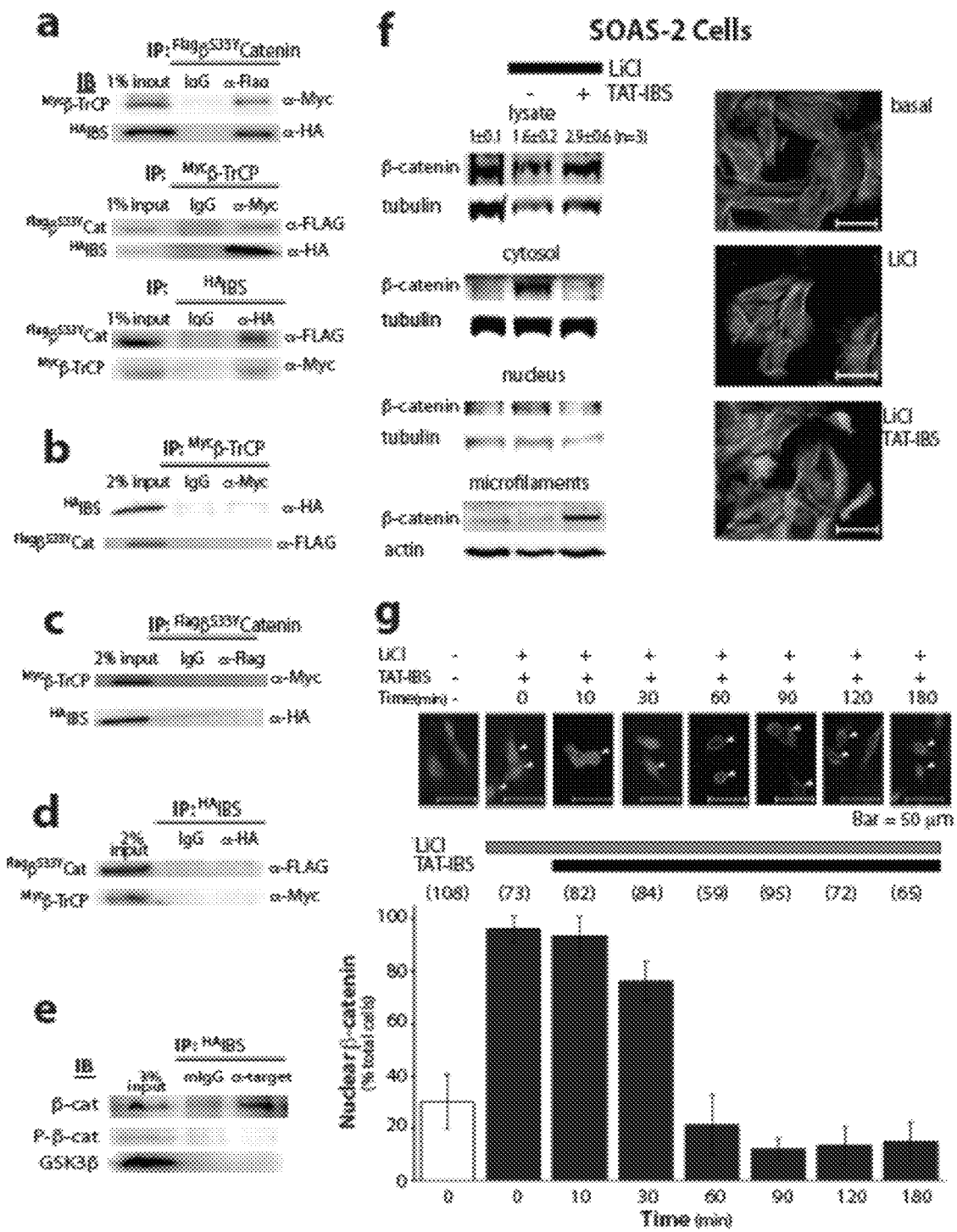

FIG. 10. Characterization of the molecular interactions between IBS, βTrCP and the β-catenin signaling pathway. a. Co-immunoprecipitation of IBS interacting βTrCP and β-catenin. Individual epitope tagged targets were immune precipitated and analyzed by immunoblot with epitope specific antibodies b-d. Co-immunoprecipitation of HEK293 cells expressing only two of the three interacting IBS, βTrCP and β-catenin. e. IBS interacts with native transcriptionally active β-catenin, but not with phospho-β-catenin or GSK3□. f. IBS blocks the cytoplasmic increase and nuclear import and increases microfilament bound β-catenin while stabilizing the total cell content (Data are the means ± SE of three independent experiments). The actin cytoskeleton was visualized using AlexaFluor[488]-phalloidin g. Rapid clearance of nuclear associated β-catenin by TAT-IBS. (Error bars represent the SE of three independent experiments). Numbers in parentheses indicate cell counts at each time point.

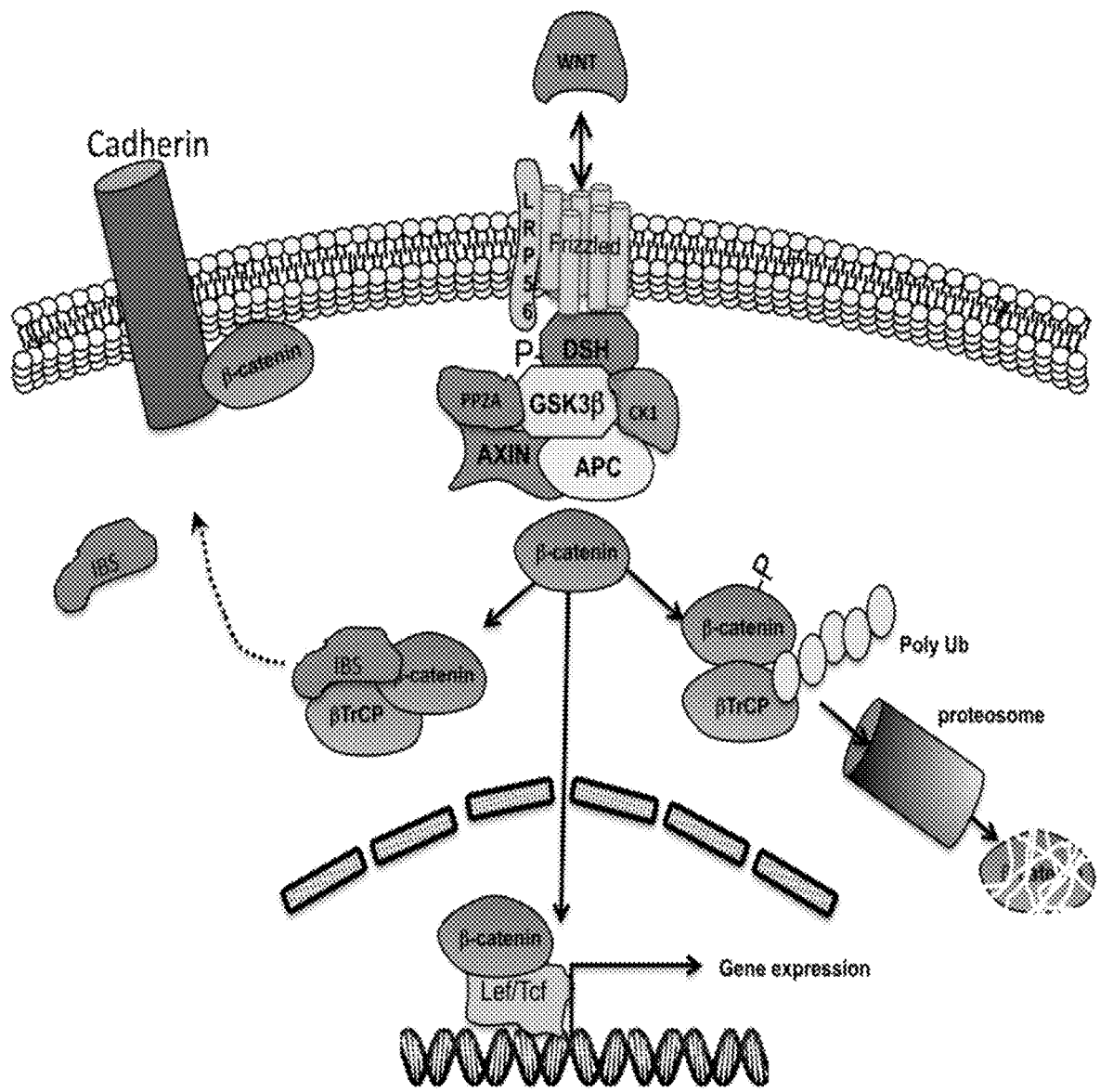

FIG. 11. Schematic diagram of the novel regulatory role of IBS in the Wnt/β-catenin signaling pathway. DSH, Disheveled; GSK3β, Glycogen synthase kinase 3 beta; CK1, Casein kinase 1; PP2A, Protein Phosphatase 2A; APC, Adenomatous Polyposis Coli; βTrCP, Transducin Repeat-Containing Protein.

Table 1. Primers used in this study.

| Primer | use | sequence | |
|---|---|---|---|
| 3HR7351F | 3 HR arm | 5'-AGAAGAGAAGACTAAGCTACTGGC | SEQ ID NO: 5 |
| 3HR8275R | 3 HR arm | 5'-GATCTGAACGGATAACTTCCTATAAGTATCTATACAAGTTATCGTTACAGTCAGTCAGAAAAG | SEQ ID NO: 6 |
| 3HR8276LAF | 3 HR arm | 5'-CCTGACTTAAGTAACTTCGTATAGCATACATTATATGAAGTTATAAAGAAACCGTTTGTCTTGTTGATTG | SEQ ID NO: 7 |
| 3HR9050 | 3 HR arm | 5'-GATCTGACTTAGTCAAGTCATTCAGGCTGCTG | SEQ ID NO: 8 |
| LF | Dkk3 locus | 5'-AAGAGCCTGCTTGGCCACTGG | SEQ ID NO: 9 |
| LR | Dkk3 locus | 5'-ACGCCATGGAGAGCTGTACC | SEQ ID NO: 10 |
| RF | Dkk3 locus | 5'-GCTGTACCGTAAAGCGGCCGC | SEQ ID NO: 11 |
| RR | Dkk3 locus | 5'-CTCACCCAGCTCCTGATTC | SEQ ID NO: 12 |
| DPF1 | genotyping | 5'-TTTGCTTGCTGCTAAGAT | SEQ ID NO: 13 |
| DPR2 | genotyping | 5'-GAGGCTGGTCACCAGGGT | SEQ ID NO: 14 |
| DCF3 | genotyping | 5'-CGTCACAACATCGAGC | SEQ ID NO: 15 |
| DCF4 | genotyping | 5'-ACCATGCAGCTCTGTCAACC | SEQ ID NO: 16 |
| Dkk3F | Off-target PCR | 5'-TGTGCAGCGGCCCTTACCTT | SEQ ID NO: 17 |
| Dkk3R | Off-target PCR | 5'-GGCTAAGATAACCCTCTGAGGTC | SEQ ID NO: 18 |
| Dlx3F | Off-target PCR | 5'-GCAGAGGAAGTCAAGTTAAGCTAGATC | SEQ ID NO: 19 |
| Dlx3R | Off-target PCR | 5'-CAGGCATTCTAGGAACCTGATCAAG | SEQ ID NO: 20 |
| Rnx6F | Off-target PCR | 5'-AAACTGGCTCGTGGGGT | SEQ ID NO: 21 |
| Rnx6R | Off-target PCR | 5'-CACAGGTGGAGTGTGGTGG | SEQ ID NO: 22 |
| Tcf7l2F | Off-target PCR | 5'-AGTCAGCCACAGTGAGCAGAG | SEQ ID NO: 23 |
| Tcf7l2R | Off-target PCR | 5'-CTTCCTGGAAATTGCAACTTG | SEQ ID NO: 24 |
| Akap9F | Off-target PCR | 5'-CCTACGGATCCGTTAGGGTACAG | SEQ ID NO: 25 |
| Akap9R | Off-target PCR | 5'-CTCAGAGGGAGTCGTCAAGTG | SEQ ID NO: 26 |
| Drh1F | Off-target PCR | 5'-CTCACTGTTTCTAGGAACCTGGTTCTGTC | SEQ ID NO: 27 |
| Drh1R | Off-target PCR | 5'-GAACAGGAAAGAAATCTGAACTCAGTCC | SEQ ID NO: 28 |
| Aldoart1F | Off-target PCR | 5'-GCAGTGGCTATAGCAGAGAGAAGAA | SEQ ID NO: 29 |
| Aldoart1R | Off-target PCR | 5'-TGCCAATGTCAAATGTAGCATGCCACTGTC | SEQ ID NO: 30 |
| Fam168bF | Off-target PCR | 5'-GCATCTGCTCAGACCGCATTG | SEQ ID NO: 31 |
| Fam168bR | Off-target PCR | 5'-GCAGTTGCAATACTGCGGGG | SEQ ID NO: 32 |
| Mett21aF | Off-target PCR | 5'-GAGAGAGAGAGAGAGAGAGAGAA | SEQ ID NO: 33 |
| Mett21aR | Off-target PCR | 5'-CAGACTTAGCTTTCTCTAGGTCCACC | SEQ ID NO: 34 |
| Rps6ka3F | Off-target PCR | 5'-GAGCGCATCAGAAACTTCAC | SEQ ID NO: 35 |
| Rps6ka3R | Off-target PCR | 5'-CCTGAAAGCTACTAGGTGCTC | SEQ ID NO: 36 |
| Arhgef2F | Off-target PCR | 5'-AGAGAGAGAGAGAGAGAGAG | SEQ ID NO: 37 |
| Arhgef2R | Off-target PCR | 5'-GGTTCAAGACCAGATGTCT | SEQ ID NO: 38 |
| TSS2F | ChIP | 5'-AGATGCCCTTTTTCTGAC | SEQ ID NO: 39 |
| TSS2R | ChIP | 5'-TGCTCCGTTGGGTACTTGG | SEQ ID NO: 40 |
| EXF2 | qPCR | 5'-CGAGCTCTAACTACCGGTAA | SEQ ID NO: 41 |
| EXR2 | qPCR | 5'-CATGAGCTCCTGTACCTCTGG | SEQ ID NO: 42 |
| EXF3 | qPCR | 5'-GGTTCCTAAACGTCCTCTG | SEQ ID NO: 43 |
| EXR3 | qPCR | 5'-GTCTGGTGTGTCCTTCTT | SEQ ID NO: 44 |
| RActF | qPCR | 5'-CTAAGGCCAACCGTGAAAG | SEQ ID NO: 45 |
| RActR | qPCR | 5'-GGTACGTTGAAGGTCTCAAA | SEQ ID NO: 46 |
| GAPDHF | qPCR | 5'-TGCCACTCAGAAGACTGTGG | SEQ ID NO: 47 |
| GAPDHR | qPCR | 5'-GGATGCAGGGATGATGTTCT | SEQ ID NO: 48 |
| DK5F | loxP scar | 5'-GAGAAGCAGCCCCTTTTCT | SEQ ID NO: 49 |
| DK5R | loxP scar | 5'-CTTCCTCGCTCACTGACTCGAATC | SEQ ID NO: 50 |

FIG. 12.

Table 2. Off-target analysis of ZFN gene edited $Dkk3^{CFP}$ mouse (Founder #19). Mouse C57bl6 genome GRCm38.

| Gene | Chr. | strand | spacer (nt) | location (nt) | Target sequence Left nuclease　　Right nuclease | # clones wt | indels | |
|---|---|---|---|---|---|---|---|---|
| Dkk3 | 7 | - | 7 | 111898811-112187861 | 5'-gaagg CAGCCCCTTTTC ttcact CAGTTGTAACTG aauga-3' | 4 | 6 | SEQ ID NO: 51 |
| Dlx1 | 12 | + | 7 | 85127751-85127781 | 5'-gccc CAGCCCCTTAGC actggt CAGCTTTAACTG tatcc-3' | 12 | 0 | SEQ ID NO: 52 |
| Rnu6 | 19 | + | 7 | 18882236-18882266 | 5'-aagtc CAGCCCCTTTC tcatctc CAGTTGTACCTG tgacg-3' | 10 | 0 | SEQ ID NO: 53 |
| Tcf7l2 | 19 | + | 7 | 55705675-55705705 | 5'-actga CACCCCCTTTC caaatga AAGTTGTAACTG gcctt-3' | 10 | 0 | SEQ ID NO: 54 |
| Akap9 | 5 | + | 7 | 3954075-3954105 | 5'-ccact CACCCCCTTTT tctgtga CAGTTGTAACAG agtgc-3' | 10 | 0 | SEQ ID NO: 55 |
| Dcbl1 | 2 | + | 7 | 166829356-166829386 | 5'-gttg CAGCCCTTTTG tagaacc CAGTTGTAAAG taact-3' | 12 | 0 | SEQ ID NO: 56 |
| Aldoart1 | 4 | + | 7 | 72528356-72528386 | 5'-gaaat CACCCCTTTTC tttgatc CATTTGAACTG actaa-3' | 10 | 0 | SEQ ID NO: 57 |
| Fam166b | 1 | - | 6 | 36835646-36835676 | 5'-ctctc CAGCCCCTTTC ttaatg CAGTTGTAAATG gagag-3' | 10 | 0 | SEQ ID NO: 58 |
| Mcm2l | 1 | + | 6 | 44981891-44981921 | 5'-gcaaa CAGTCCCTTTTA tactgt CAGTGTACCTG actgt-3' | 8 | 0 | SEQ ID NO: 59 |
| Rps6kb3 | 12 | + | 5 | 108823556-108823586 | 5'-tcact GAGCCATTTTC tggct CAGTTGTAACTG ttta-3' | 10 | 0 | SEQ ID NO: 60 |
| Itgb2 | 3 | - | 5 | 100785756-100785786 | 5'-agtga CAGCCCCTTTC agaaa CCGTTGTACTG cctgg-3' | 10 | 0 | SEQ ID NO: 61 |

FIG. 13

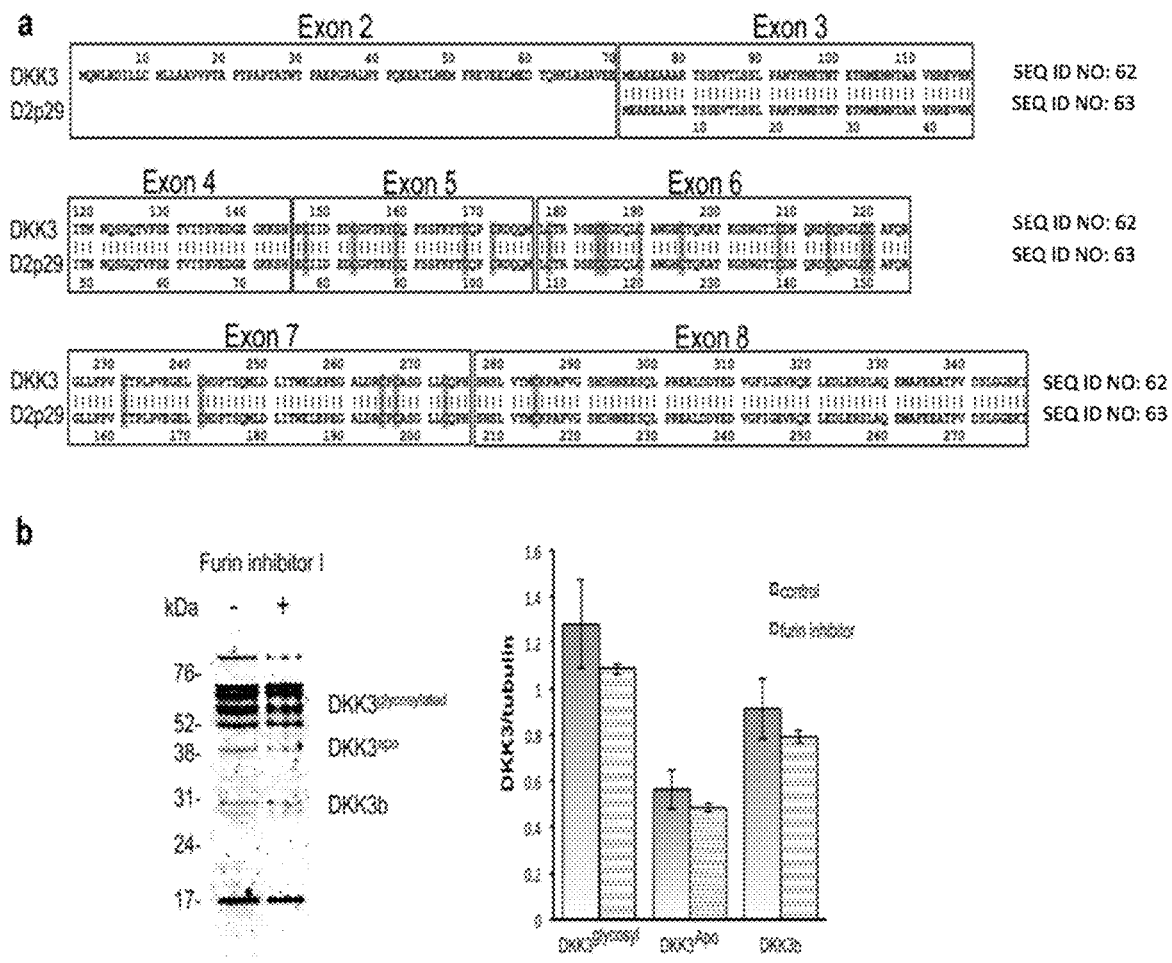
FIG. 14. Comparison of *Dkk3* isoforms in mouse astrocytes. a. Alignment of the amino acid sequences of DKK3 and D2p29. b. Effects of Furin proteolysis on DKK3 isoforms in astrocytes. Image analysis software (Odyssey, LI-COR) was used to measure individual DKK3 bands and the data normalized to tubulin. Data represent 3 independent cell preparations/furin digests.

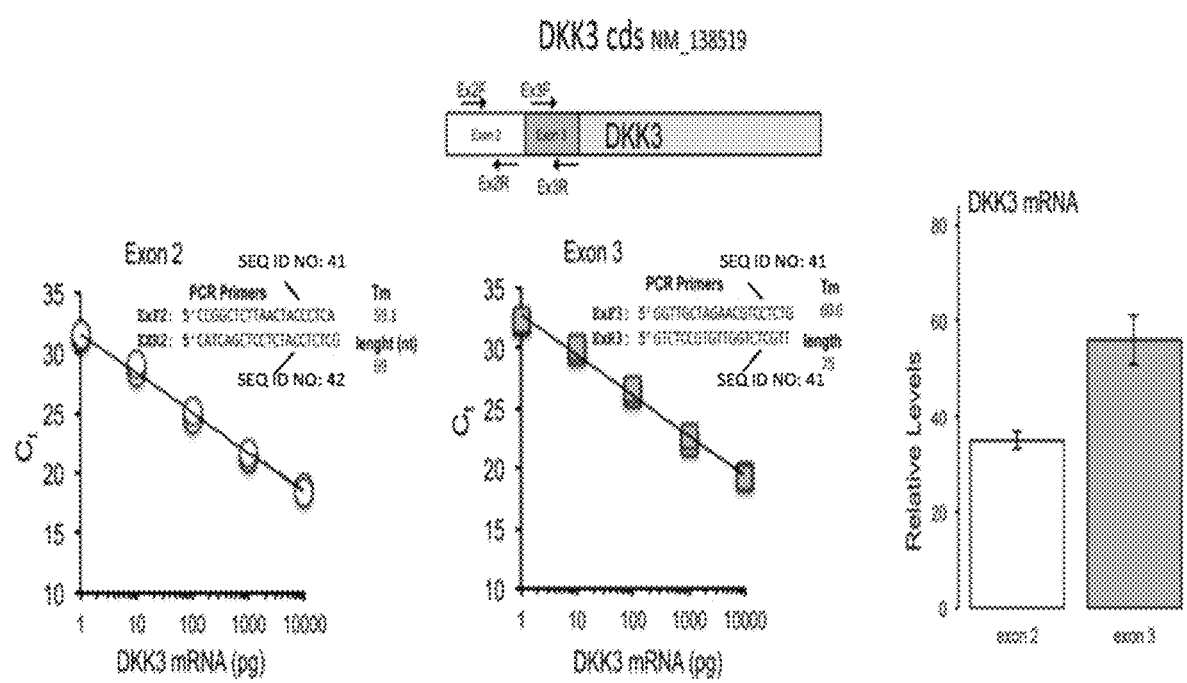
FIG. 15. Exon specific qPCR analysis of *Dkk3* transcripts in rat astrocytes. Validation of the *Dkk3* exon 2 and exon 3 primer sets. *Dkk3* mRNA levels were normalized to GAPDH mRNA. Data (mean ± SE) from 3 independent experiments.

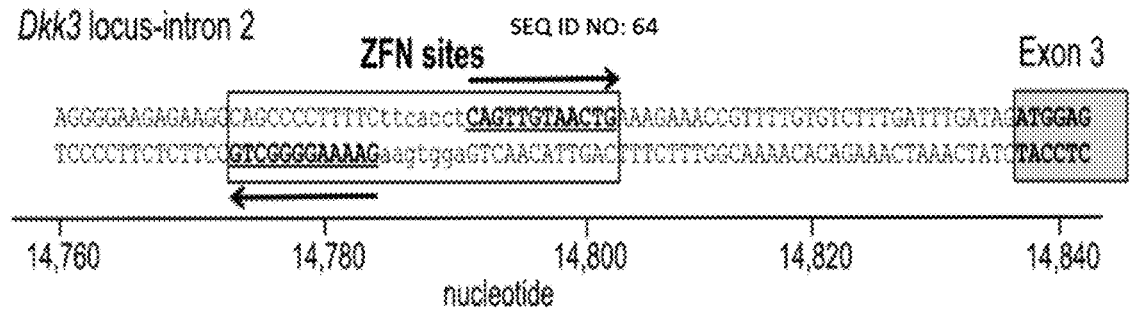
FIG. 16. ZFN target in intron 2 of the *Dkk3* gene. a. Sequence and location of the target sequence relative to exon 3. b. Complete amino acid sequences of the epitope tagged ZFNs.

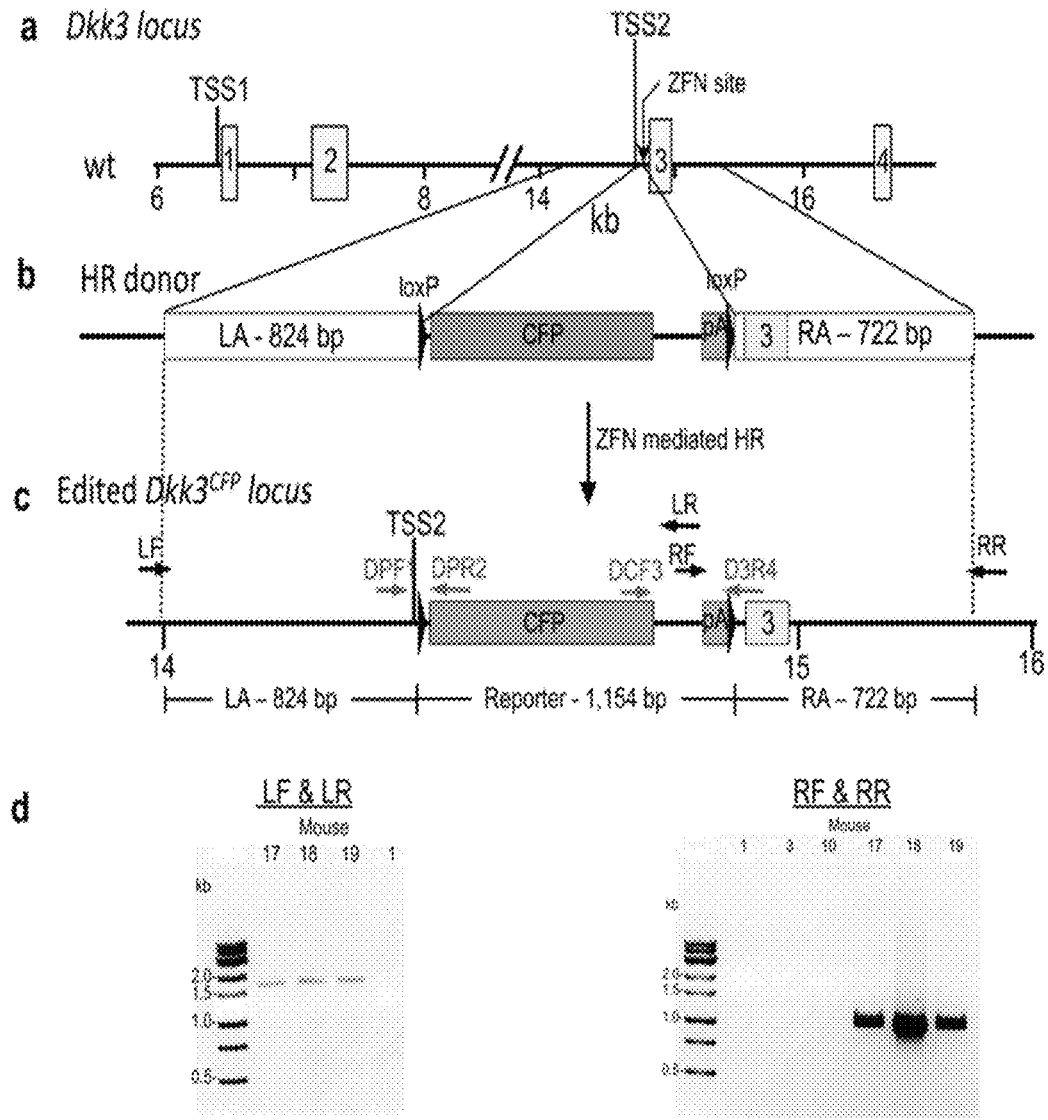

FIG. 17. Schematic Diagram of the ZFN mediated gene editing of the mouse *Dkk3* gene. a. Organization of the first 4 exons of the wild type *Dkk3* locus. TSS1, transcriptional start site 1; TSS2, transcriptional start site 2. b. Schematic diagram of the HR donor. c. Schematic diagram of the gene edited *Dkk3*$^{CFP}$ locus. Genotyping PCR primers indicated by arrows (Table 1). Agarose gel confirmation of CFP insertion at the ZFN target locus in the *Dkk3*$^{CFP}$ mouse.

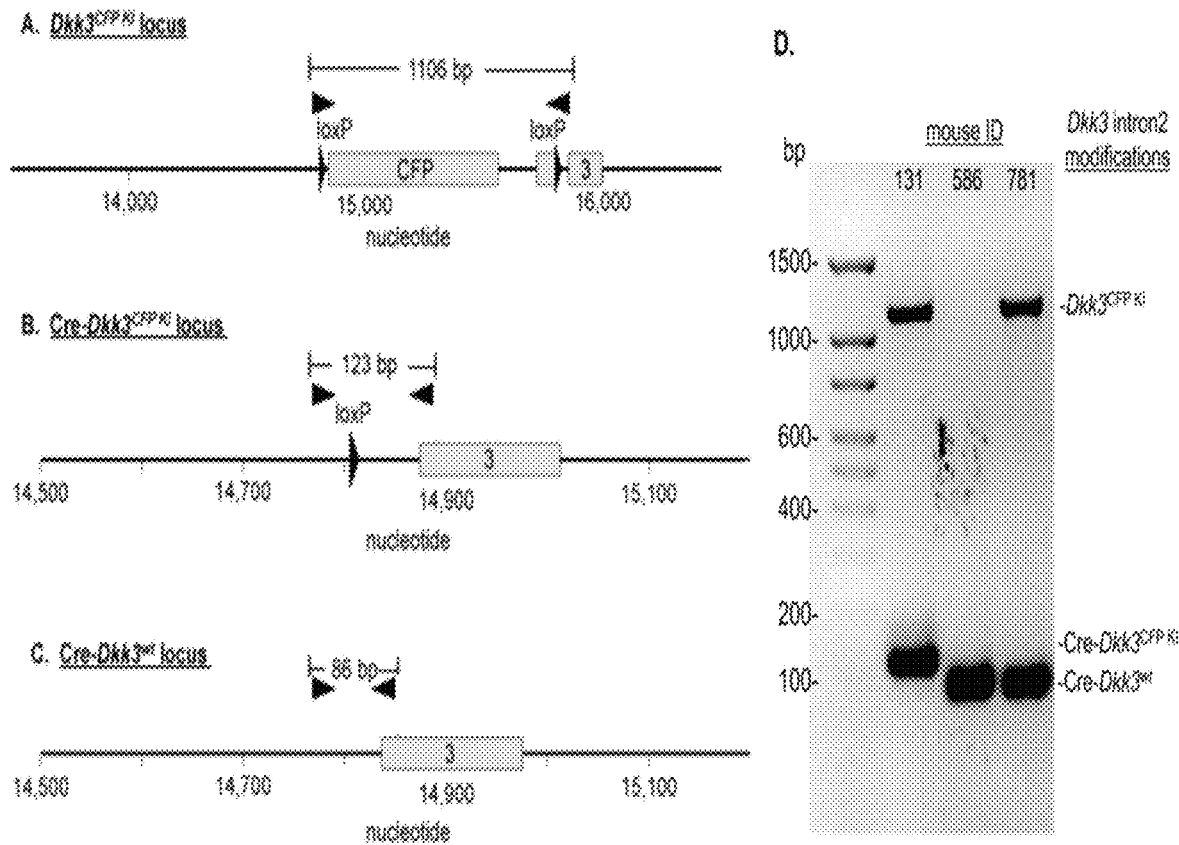

FIG. 18. Sox2 promoter-Cre Rescue of the Lethal Phenotype of the $Dkk3^{CFP}$ mouse. a. Schematic diagram of the $Dkk3^{CFP}$ locus. Arrow heads indicate the location of PCR primers DKSF and DKSR. b. Schematic diagram of $Dkk3^{CFP}$ locus after Cre recombination. c. Schematic diagram of the $Dkk3^{wt}$ locus. d. Agarose gel analysis of PCR products produced from 6 week old mouse DNA of a representative homozygote gene edited (#131), a wild type (#586), and a heterozygote gene edited (#781).

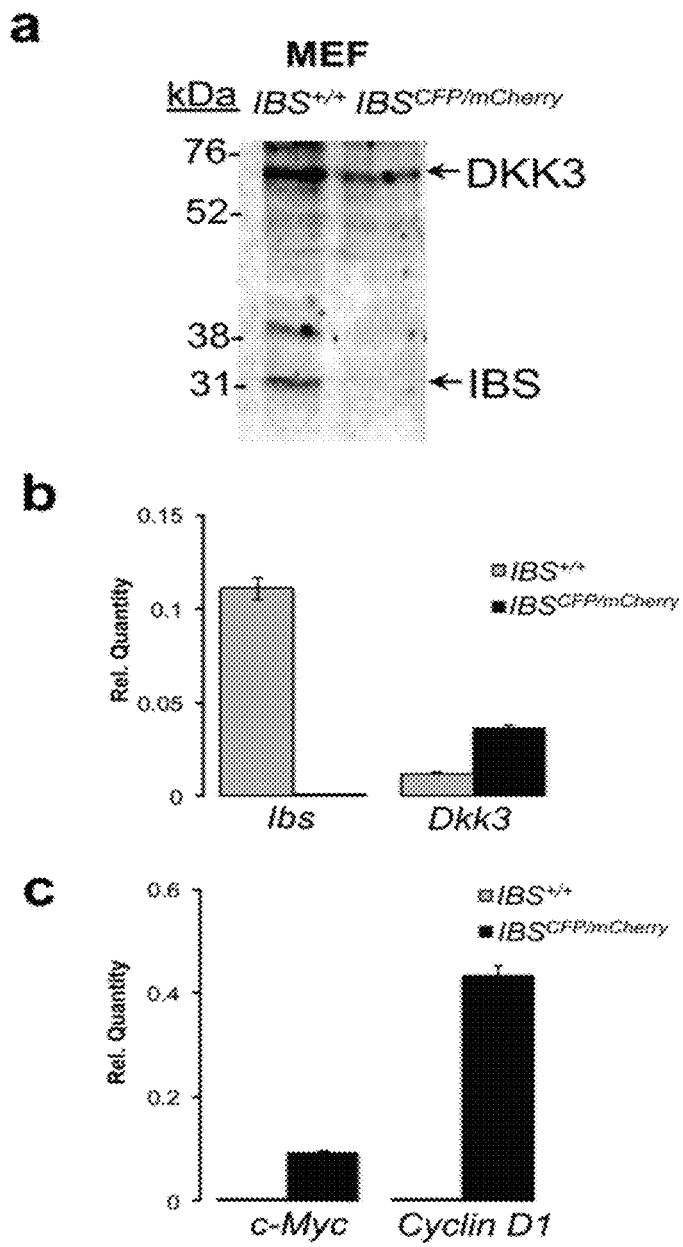

FIG. 19. Effects of loss of IBS by bi-allelic insertion diversion the *Dkk3* TSS2 in MEFs. a. MEFs were prepared from 16 d old heterozygous $Dkk3^{CFP/+}$ embryos and the wild type *Dkk3* allele was re-edited with ZFNs and a mCherry HR donor. Bi-allelic gene-edited, IBS knockout, $Dkk3^{CFP/mCherry}$ cells that express both CFP and mCherry were isolated by FACS. Immunoblot analysis of the DKK3 isoforms present in the homozygous $Dkk3^{CFP/mCherry}$ cells. b. qPCR analysis of *Dkk3* transcripts present in wild-type and IBS knockout MEFS. Transcript abundance measured by the □□CT method using GAPDH as the control. Data represent the means ± se of triplicate dishes. c. qPCR analysis of *c-Myc* and *Cyclin D1* transcripts present in wild-type and IBS knockout MEFS. Transcript abundance measured by the □□CT method using GAPDH as the control. Data represent the means ± se of triplicate dishes.

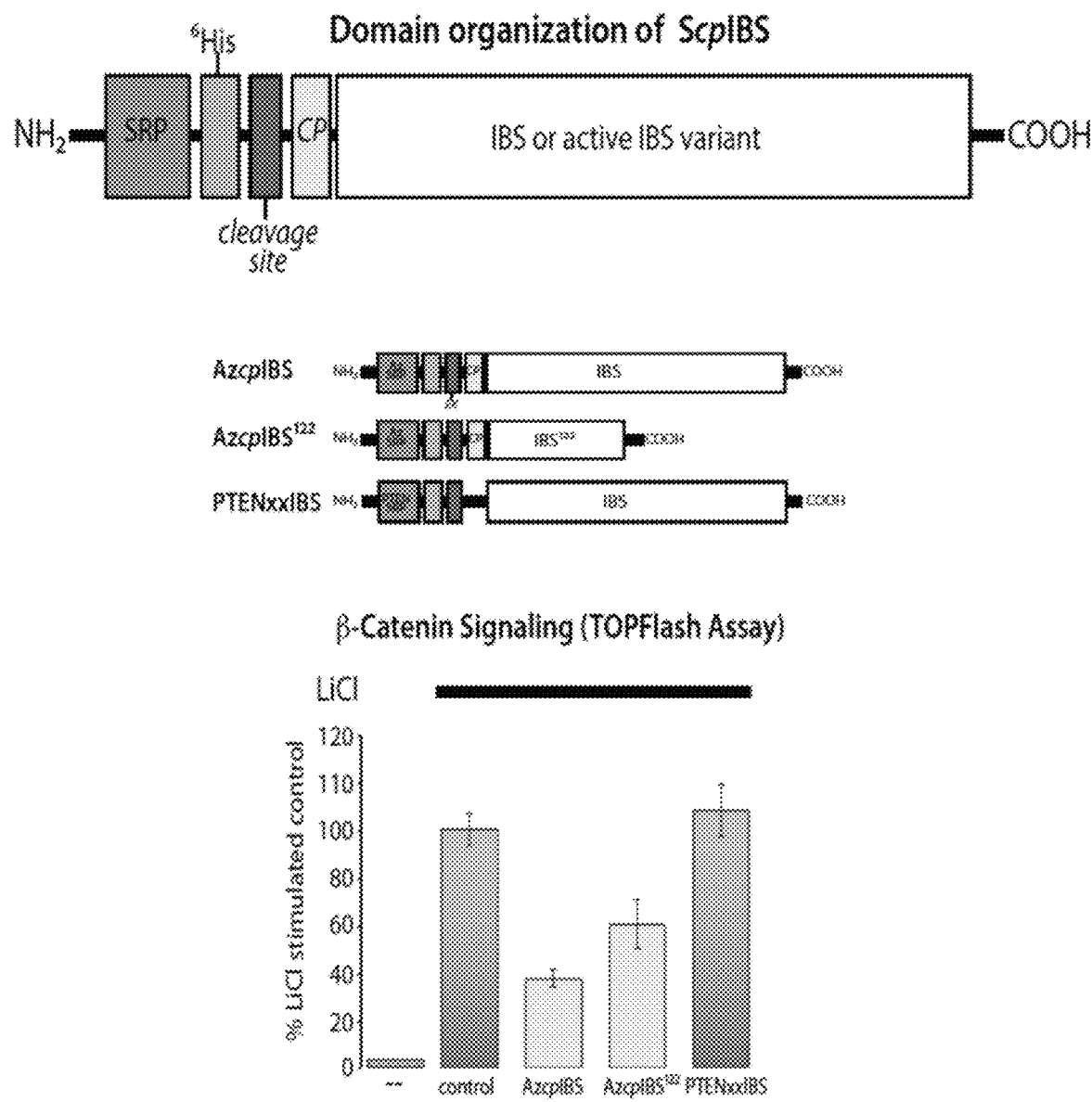
FIG. 20. Domain organization of ScpIBS and β-catenin signaling.

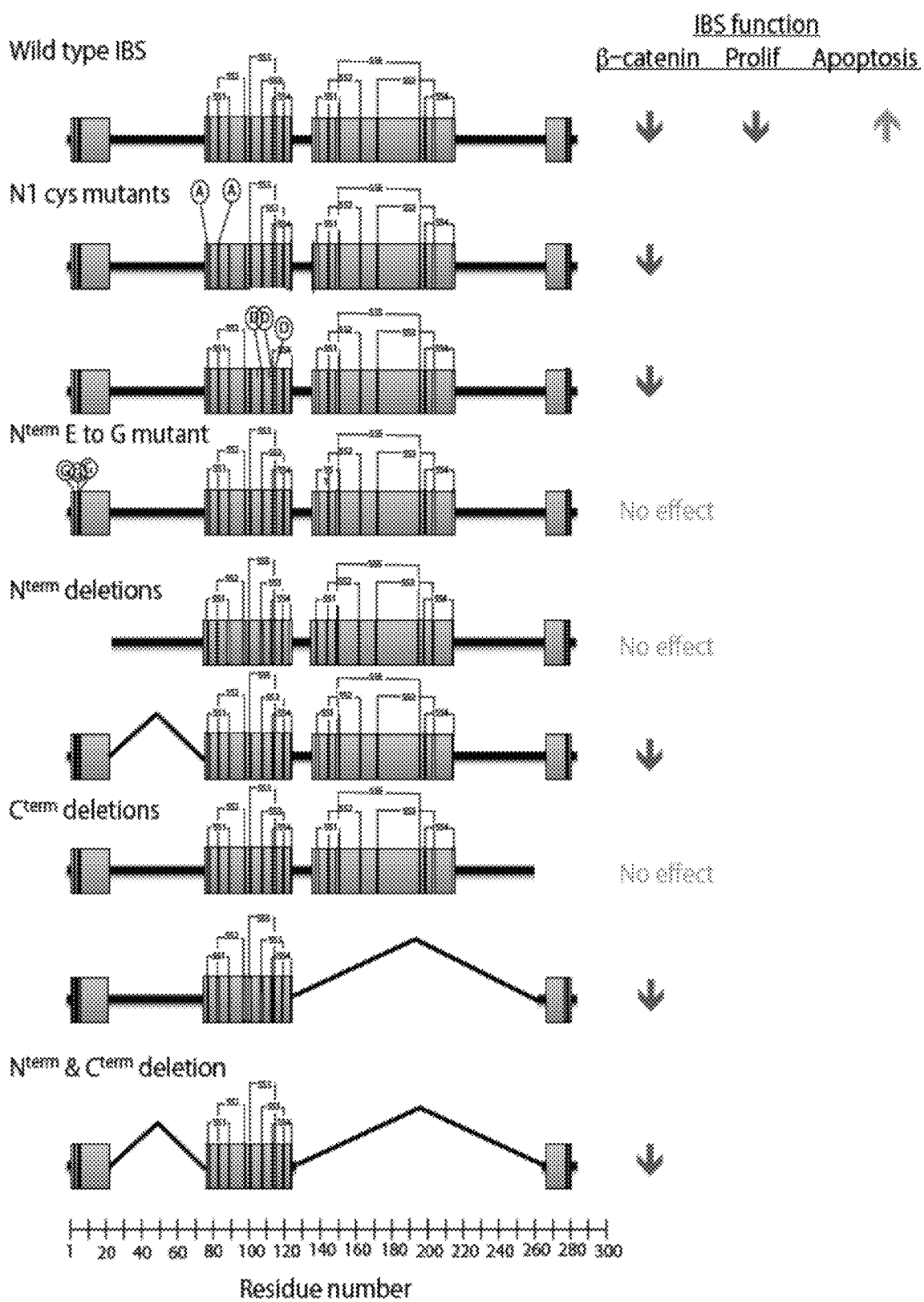
FIG. 21. Accumulated mutation/deletion/truncation evaluation of the essential domains of the IBS protein.

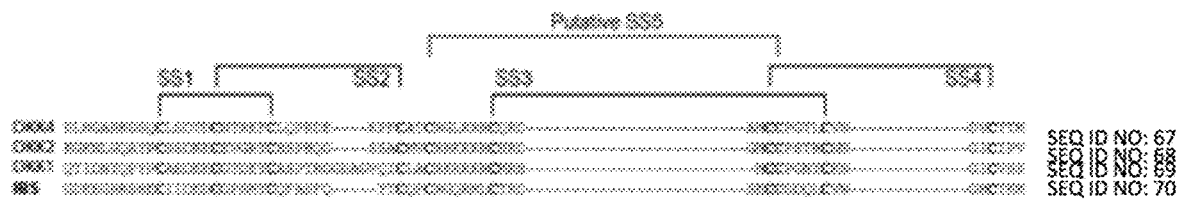
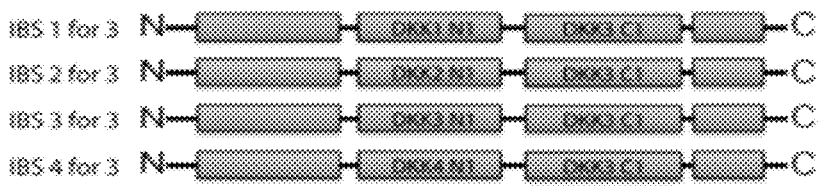
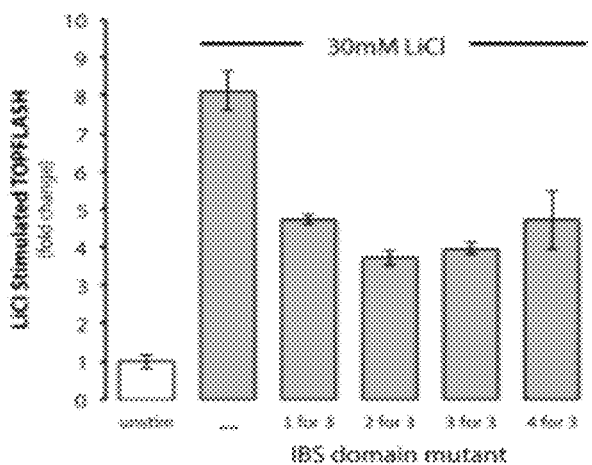
FIG. 22. Effects of the N-1 domain of the DKK family on β-catenin signaling.

A.

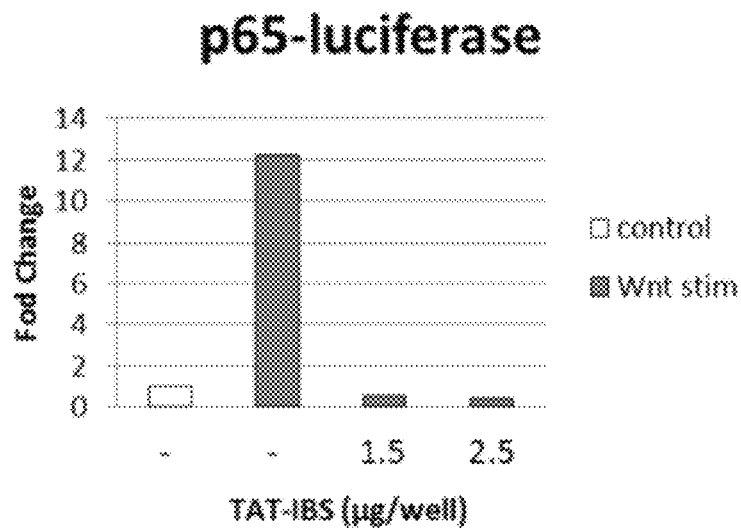

B.

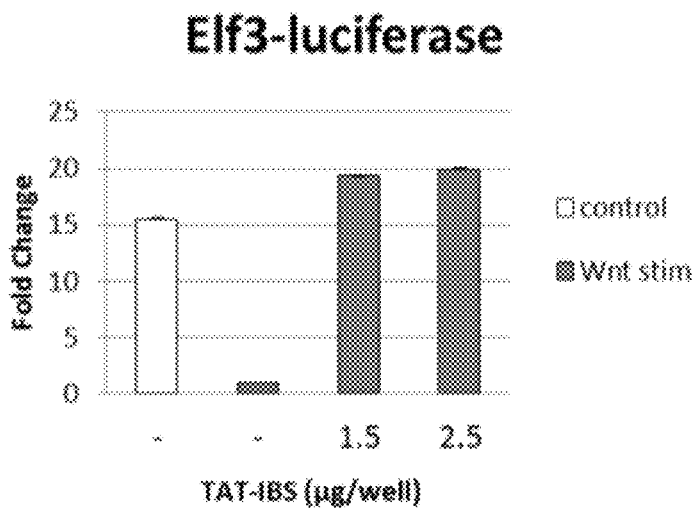

FIG. 23. TAT-IBS antagonizes primary and secondary β-catenin and NF-κB-dependent gene expression. A) TAT-IBS blocks an NF-κB (p65) –responsive promoter driving luciferase reporter in HEK293 cells that was stimulated by Wnt-1 transfection (shaded bars). B) TAT-IBS restores transcriptional activity of Elf3-luciferase, a reporter of epithelial differentiation that is suppressed by Wnt-1 stimulation. C) (Data previously disclosed in UMMC 12-40PR2). TAT-IBS restores *E-Cadherin* (*CDH1*)-promoter activity in Wnt-1 stimulated cells (middle chart). TopFlash and E2F-luciferase reporters are dependent on β-TrCP substrates, β-catenin and E2F, respectively (top and bottom charts). TAT-IBS blocks transcriptional activation by Wnt-1 stimulation of both reporters.

C.

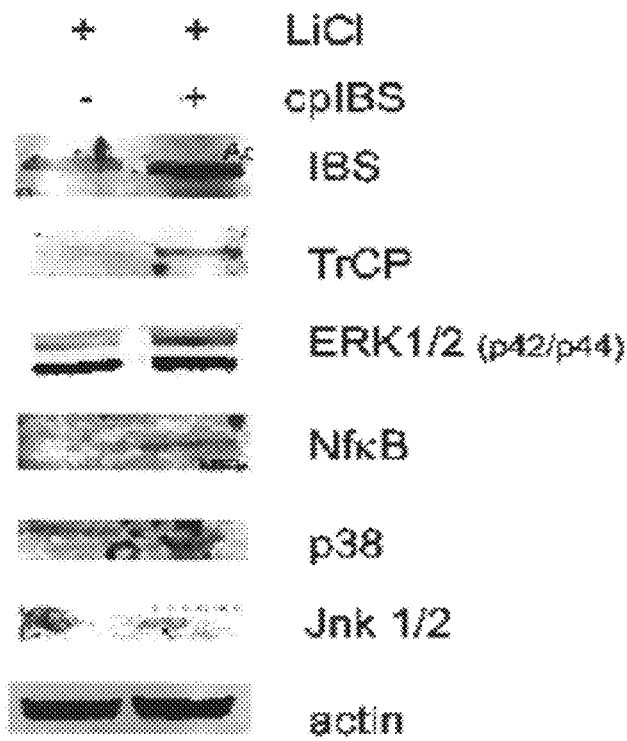

FIG. 24. IBS increases microfilament-bound β-TRCP substrates. SOAS-2 cells were stimulated with the GSK3 inhibitor, LiCl, to stabilize β-catenin and mimic Wnt-1 pathway activation. Untreated and IBS-treated microfilament fractions of cell lysates show that short-term (90 min.) IBS replacement resulted in β-TrCP, Erk1/2, NF-κB, and p38 proteins complexes bound to microfilaments. Thus, the inhibitory complex formed between IBS, β-TrCP and β-TrCP target substrates interrupts the nuclear import and defines the molecular basis for the silencing of β-TrCP substrate signaling by IBS.

SEQUENCE LISTING

```
<160> NUMBER OF SEQ ID NOS: 72

<210> SEQ ID NO 1
<211> LENGTH: 61
<212> TYPE: PRT
<213> ORGANISM: Homo sapiens

<400> SEQUENCE: 1

Met Leu Glu Arg Gly Gly Glu Ala Ala Ala Ala Ala Ala Ala Ala
1               5                   10                  15
```

Ala Ala Pro Gly Arg Gly Ser Glu Ser Pro Val Thr Ile Ser Arg Ala
            20                  25                  30

Gly Asn Ala Gly Glu Leu Val Ser Pro Leu Leu Leu Pro Pro Thr Arg
        35                  40                  45

Arg Arg Arg Arg Arg His Ile Gln Gly Pro Gly Pro Val
    50                  55                  60

<210> SEQ ID NO 2
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Ala Ala Ala Leu Leu Gly Gly Glu Glu Ile
1               5                   10

<210> SEQ ID NO 3
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 3

His His His His His His
1               5

<210> SEQ ID NO 4
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Tyr Ala Arg Ala Ala Ala Arg Gln Ala Arg Ala Gly
1               5                   10

<210> SEQ ID NO 5
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
agagagagag agactaaggt actggc                                              26

<210> SEQ ID NO 6
<211> LENGTH: 74
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gatcctgaac cggtataact tcgtataatg tatgctatac gaagttatca gttacaactg         60
aggtgaagaa aagg                                                           74

<210> SEQ ID NO 7
<211> LENGTH: 73
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
cctgacttaa gataacttcg tatagcatac attatacgaa gttataaaga aaccgttttg    60
tgtctttgat ttg                                                       73

<210> SEQ ID NO 8
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
gatcctgact taagtcaagt cattcaggct ggttg                               35

<210> SEQ ID NO 9
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
aaggaccctg ccttggccac ttgg                                           24

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
acggcatgga cgagctgtac c                                              21

<210> SEQ ID NO 11
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gctgtaccgc taaagcggcc gc                                             22

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
ctccacccag ctcctgattc                                                20

```
<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
tttggcttgc tggctaagat                                              20

<210> SEQ ID NO 14
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
gagggtggtc accagggt                                                18

<210> SEQ ID NO 15
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
cgccacaaca tcgagg                                                  16

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
accatgaggt ctcgtcaacc                                              20

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
tgtgccacgg cccttacctt                                              20

<210> SEQ ID NO 18
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
ggctaagata acccttctga ggtc                                         24
```

<210> SEQ ID NO 19
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
gcagaggaag tgcaagttta aggctagatc                                    30

<210> SEQ ID NO 20
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
cagccattct agaaaccctg atcaag                                        26

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
aaactggctc tcgtgggggt                                               20

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
cacaggtgac agtgtggtgg                                               20

<210> SEQ ID NO 23
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
atgtcagccc acagtgatga gag                                           23

<210> SEQ ID NO 24
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
ctccctggaa attggcagct tg                                            22

<210> SEQ ID NO 25
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 25
cctacagatc cgttaagggt acag                                          24

<210> SEQ ID NO 26
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 26
ctcagaggag gagtcatcaa gtg                                           23

<210> SEQ ID NO 27
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 27
ctcactgttt ctaggaacct tggttctgtc                                    30

<210> SEQ ID NO 28
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 28
gaacagagaa agaaagtctg agctcagtcc                                    30

<210> SEQ ID NO 29
<211> LENGTH: 26
<212> TYPE: DNA
<213> ORGANISM: Artificial Sequence
<220> FEATURE:
<223> OTHER INFORMATION: Description of Artificial Sequence: Synthetic primer

<400> SEQUENCE: 29
gcagtggcta tagcagagag gaagaa                                        26

<210> SEQ ID NO 30
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 30
tgccgatgtc aaatgtagca tggcactatc                                    30

<210> SEQ ID NO 31

```
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
gcatctgtct gcagaccaca tttg                                              24

<210> SEQ ID NO 32
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
gcacgttcac aatactgtgg gg                                                22

<210> SEQ ID NO 33
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
gagagagaga gagagagaga gagagaagaa                                        30

<210> SEQ ID NO 34
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
cagagttagc atttcttcta ggctccacc                                         29

<210> SEQ ID NO 35
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
gaggcgcatg cagaaacttc ac                                                22

<210> SEQ ID NO 36
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
cctgaaaagc ctactaggtc tctc                                              24

<210> SEQ ID NO 37
<211> LENGTH: 24
```

<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
agagagagag agagagagag agag                                          24

<210> SEQ ID NO 38
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
ggtggcaaga accagatgtg ct                                            22

<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
agatggcccc ttttcttcac                                               20

<210> SEQ ID NO 40
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
tggtctcgtt gtggtagttg g                                             21

<210> SEQ ID NO 41
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
ccggctctta actaccctca                                               20

<210> SEQ ID NO 42
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
catcagctcc tctacctctc g                                             21

<210> SEQ ID NO 43
<211> LENGTH: 20
<212> TYPE: DNA

```
<213> ORGANISM: Artificial Sequence
<220> FEATURE:
<223> OTHER INFORMATION: Description of Artificial Sequence: Synthetic
      primer

<400> SEQUENCE: 43
ggttgctaga acgtcctctg                                                 20

<210> SEQ ID NO 44
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
gtctccgtgt tggtctcgtt                                                 20

<210> SEQ ID NO 45
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
ctaaggccaa ccgtgaaaag                                                 20

<210> SEQ ID NO 46
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
ggggtgttga aggtctcaaa                                                 20

<210> SEQ ID NO 47
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
tgccactcag aagactgtgg                                                 20

<210> SEQ ID NO 48
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
ggatgcaggg atgatgttct                                                 20

<210> SEQ ID NO 49
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 49
gagaaggcag cccctttct                                                    20

<210> SEQ ID NO 50
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
cttcttccgc ctccatctat caaatc                                            26

<210> SEQ ID NO 51
<211> LENGTH: 41
<212> TYPE: DNA
<213> ORGANISM: Mus sp.

<400> SEQUENCE: 51
gaaggcagcc ccttttcttc acctcagttg taactgaaag a                            41

<210> SEQ ID NO 52
<211> LENGTH: 41
<212> TYPE: DNA
<213> ORGANISM: Mus sp.

<400> SEQUENCE: 52
gcccccagcc ccttagcact ggctcagctt taactgtatc c                            41

<210> SEQ ID NO 53
<211> LENGTH: 41
<212> TYPE: DNA
<213> ORGANISM: Mus sp.

<400> SEQUENCE: 53
aagtccaacc ccttttctca tctccagttg gccctgtggc g                            41

<210> SEQ ID NO 54
<211> LENGTH: 41
<212> TYPE: DNA
<213> ORGANISM: Mus sp.

<400> SEQUENCE: 54
actgacaccc cctttccaa atgaatgttg taactggcct t                             41

<210> SEQ ID NO 55
<211> LENGTH: 41
<212> TYPE: DNA
<213> ORGANISM: Mus sp.

<400> SEQUENCE: 55
ccactcatcc ccttttttct gtgacagttg taacagagtg c                            41

<210> SEQ ID NO 56
<211> LENGTH: 41
<212> TYPE: DNA
<213> ORGANISM: Mus sp.

<400> SEQUENCE: 56
```

-continued

```
gtttgcagcc cttttgtag aacccagttg taaaagtaac t                41
```

<210> SEQ ID NO 57
<211> LENGTH: 41
<212> TYPE: DNA
<213> ORGANISM: Mus sp.

<400> SEQUENCE: 57

```
gaaatcacct cctttctt gatccatttg aaactgacta a                 41
```

<210> SEQ ID NO 58
<211> LENGTH: 40
<212> TYPE: DNA
<213> ORGANISM: Mus sp.

<400> SEQUENCE: 58

```
ctctccagcc ccctttctta atgcagttgt aaatggagag                  40
```

<210> SEQ ID NO 59
<211> LENGTH: 40
<212> TYPE: DNA
<213> ORGANISM: Mus sp.

<400> SEQUENCE: 59

```
gcaaacagtc cctttatac tgtcaggtgt acctgactgt                   40
```

<210> SEQ ID NO 60
<211> LENGTH: 39
<212> TYPE: DNA
<213> ORGANISM: Mus sp.

<400> SEQUENCE: 60

```
tcactgagcc aattttctgg cccagttgta actgttta                    39
```

<210> SEQ ID NO 61
<211> LENGTH: 39
<212> TYPE: DNA
<213> ORGANISM: Mus sp.

<400> SEQUENCE: 61

```
agtgacagcc cctttcaga aaccgtggtc actgcctgg                    39
```

<210> SEQ ID NO 62
<211> LENGTH: 348
<212> TYPE: PRT
<213> ORGANISM: Unknown
<220> FEATURE:
<223> OTHER INFORMATION: Description of Unknown:
      DKK3 sequence

<400> SEQUENCE: 62

```
Met Gln Trp Leu Arg Asp Ile Leu Leu Cys Met Leu Leu Ala Ala Val
1               5                   10                  15

Val Pro Thr Ala Pro Thr Pro Ala Pro Thr Ala Trp Thr Pro Ala
            20                  25                  30

Glu Pro Gly Pro Ala Leu Asn Tyr Pro Gln Glu Glu Ala Thr Leu Asn
        35                  40                  45

Glu Met Phe Arg Glu Val Glu Glu Leu Met Glu Asp Thr Gln His Lys
    50                  55                  60

Leu Arg Ser Ala Val Glu Glu Met Glu Ala Glu Glu Ala Ala Ala Arg
65                  70                  75                  80

Thr Ser Ser Glu Val Thr Leu Ser Ser Leu Pro Ala Asn Tyr His Asn
```

```
                        85                  90                  95

Glu Thr Asn Thr Glu Thr Arg Met Glu Asn Asn Thr Ala His Val His
                100                 105                 110

Arg Glu Val His Lys Ile Thr Asn Asn Gln Ser Gly Gln Thr Val Phe
                115                 120                 125

Ser Glu Thr Val Ile Thr Ser Val Glu Asp Gly Glu Gly Lys Lys Ser
            130                 135                 140

His Glu Cys Ile Ile Asp Glu Asp Cys Gly Pro Thr Arg Tyr Cys Gln
145                 150                 155                 160

Phe Ser Ser Phe Lys Tyr Thr Cys Gln Pro Cys Arg Asp Gln Gln Met
                165                 170                 175

Leu Cys Thr Arg Asp Ser Glu Cys Cys Gly Asp Gln Leu Cys Ala Trp
                180                 185                 190

Gly His Cys Thr Gln Lys Ala Thr Lys Gly Ser Asn Gly Thr Ile Cys
            195                 200                 205

Asp Asn Gln Arg Asp Cys Gln Pro Gly Leu Cys Cys Ala Phe Gln Arg
        210                 215                 220

Gly Leu Leu Phe Pro Val Cys Thr Pro Leu Pro Val Glu Gly Glu Leu
225                 230                 235                 240

Cys His Asp Pro Thr Ser Gln Met Leu Asp Leu Ile Thr Trp Glu Leu
                245                 250                 255

Glu Pro Glu Gly Ala Leu Asp Arg Cys Pro Cys Ala Ser Gly Leu Leu
            260                 265                 270

Cys Gln Pro His Ser His Ser Leu Val Tyr Met Cys Lys Pro Ala Phe
        275                 280                 285

Val Gly Ser His Asp His Asn Glu Glu Ser Gln Leu Pro Arg Glu Ala
    290                 295                 300

Leu Asp Asp Tyr Glu Asp Val Gly Phe Ile Gly Glu Val Arg Gln Glu
305                 310                 315                 320

Leu Glu Asp Leu Glu Arg Ser Leu Ala Gln Glu Met Ala Phe Glu Glu
                325                 330                 335

Ala Thr Pro Val Asp Ser Leu Gly Gly Glu Lys Ile
                340                 345

<210> SEQ ID NO 63
<211> LENGTH: 277
<212> TYPE: PRT
<213> ORGANISM: Unknown
<220> FEATURE:
<223> OTHER INFORMATION: Description of Unknown:
      D2p29 sequence

<400> SEQUENCE: 63

Met Glu Ala Glu Ala Ala Arg Thr Ser Ser Glu Val Thr Leu
1               5                   10                  15

Ser Ser Leu Pro Ala Asn Tyr His Asn Glu Thr Asn Thr Glu Thr Arg
                20                  25                  30

Met Glu Asn Asn Thr Ala His Val His Arg Glu Val His Lys Ile Thr
            35                  40                  45

Asn Asn Gln Ser Gly Gln Thr Val Phe Ser Glu Thr Val Ile Thr Ser
        50                  55                  60

Val Glu Asp Gly Glu Gly Lys Lys Ser His Glu Cys Ile Ile Asp Glu
65                  70                  75                  80

Asp Cys Gly Pro Thr Arg Tyr Cys Gln Phe Ser Ser Phe Lys Tyr Thr
                85                  90                  95
```

```
Cys Gln Pro Cys Arg Asp Gln Gln Met Leu Cys Thr Arg Asp Ser Glu
                100                 105                 110

Cys Cys Gly Asp Gln Leu Cys Ala Trp Gly His Cys Thr Gln Lys Ala
        115                 120                 125

Thr Lys Gly Ser Asn Gly Thr Ile Cys Asp Asn Gln Arg Asp Cys Gln
    130                 135                 140

Pro Gly Leu Cys Cys Ala Phe Gln Arg Gly Leu Leu Phe Pro Val Cys
145                 150                 155                 160

Thr Pro Leu Pro Val Glu Gly Glu Leu Cys His Asp Pro Thr Ser Gln
                165                 170                 175

Met Leu Asp Leu Ile Thr Trp Glu Leu Glu Pro Glu Gly Ala Leu Asp
            180                 185                 190

Arg Cys Pro Cys Ala Ser Gly Leu Leu Cys Gln Pro His Ser His Ser
        195                 200                 205

Leu Val Tyr Met Cys Lys Pro Ala Phe Val Gly Ser His Asp His Asn
    210                 215                 220

Glu Glu Ser Gln Leu Pro Arg Glu Ala Leu Asp Asp Tyr Glu Asp Val
225                 230                 235                 240

Gly Phe Ile Gly Glu Val Arg Gln Glu Leu Glu Asp Leu Glu Arg Ser
                245                 250                 255

Leu Ala Gln Glu Met Ala Phe Glu Glu Ala Thr Pro Val Asp Ser Leu
            260                 265                 270

Gly Gly Glu Lys Ile
        275

<210> SEQ ID NO 64
<211> LENGTH: 83
<212> TYPE: DNA
<213> ORGANISM: Unknown
<220> FEATURE:
<223> OTHER INFORMATION: Description of Unknown:
      DKK3 sequence

<400> SEQUENCE: 64 agggggaagag aaggcagccc cttttcttca cctcagttgt aactgaaaga aaccgttttg      60
tgtctttgat ttgatagatg gag                                              83

<210> SEQ ID NO 65
<211> LENGTH: 322
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

Tyr Pro Tyr Asp Val Pro Asp Tyr Ala Thr Glu Arg Pro Tyr Lys Cys
1               5                   10                  15

Pro Glu Cys Gly Lys Ser Phe Ser Arg Ser Asp Thr Leu Lys Glu His
            20                  25                  30

Gln Arg Thr His Thr Gly Glu Lys Pro Tyr Ala Cys Pro Val Glu Ser
        35                  40                  45

Cys Asp Arg Arg Phe Ser Arg Ser Ser His Leu Thr Arg His Ile Arg
    50                  55                  60

Ile His Thr Gly Gln Lys Pro Phe Gln Cys Arg Ile Cys Met Arg Asn
65                  70                  75                  80

Phe Ser Arg Ser Asp His Leu Thr Gln His Ile Arg Thr His Thr Gly
                85                  90                  95
```

```
Glu Lys Pro Phe Ala Cys Asp Ile Cys Gly Arg Lys Phe Ala Gln Arg
            100                 105                 110

Gly Asn Leu Thr Arg His Thr Lys Ile His Thr Gly Gly Ser Gln Leu
        115                 120                 125

Val Lys Ser Glu Leu Glu Glu Lys Ser Glu Leu Arg His Lys Leu
130                 135                 140

Lys Tyr Val Pro His Glu Tyr Ile Glu Leu Ile Glu Ile Ala Arg Asn
145                 150                 155                 160

Ser Thr Gln Asp Arg Ile Leu Glu Met Lys Val Met Glu Phe Phe Met
                165                 170                 175

Lys Val Tyr Gly Tyr Arg Gly Lys His Leu Gly Gly Ser Arg Lys Pro
            180                 185                 190

Asp Gly Ala Ile Tyr Thr Val Gly Ser Pro Ile Asp Tyr Gly Val Ile
        195                 200                 205

Val Asp Thr Lys Ala Tyr Ser Gly Gly Tyr Asn Leu Pro Ile Gly Gln
210                 215                 220

Ala Asp Glu Met Gln Asp Tyr Val Glu Glu Asn Gln Thr Arg Asn Lys
225                 230                 235                 240

His Ile Asn Pro Asn Glu Trp Trp Lys Val Tyr Pro Ser Ser Val Thr
                245                 250                 255

Glu Phe Lys Phe Leu Phe Val Ser Gly His Phe Lys Gly Asn Tyr Lys
            260                 265                 270

Ala Gln Leu Thr Arg Leu Asn His Ile Thr Asn Cys Asn Gly Ala Val
        275                 280                 285

Leu Ser Val Glu Glu Leu Leu Ile Gly Gly Glu Met Ile Lys Ala Gly
290                 295                 300

Thr Leu Thr Leu Glu Glu Val Arg Arg Lys Phe Asn Asn Gly Glu Ile
305                 310                 315                 320

Asn Phe

<210> SEQ ID NO 66
<211> LENGTH: 320
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

Asp Tyr Lys Asp Asp Asp Lys Thr Glu Arg Pro Tyr Lys Cys Pro Glu
1               5                   10                  15

Cys Gly Lys Ser Phe Ser Arg Ser Asp Thr Leu Val Glu His Gln Arg
            20                  25                  30

Thr His Thr Gly Glu Lys Pro Tyr Ala Cys Pro Val Glu Ser Cys Asp
        35                  40                  45

Arg Arg Phe Ser Gln Arg Gly Asn Leu Thr Thr His Ile Arg Ile His
    50                  55                  60

Thr Gly Gln Lys Pro Phe Gln Cys Arg Ile Cys Met Arg Asn Phe Ser
65                  70                  75                  80

Arg Ser Asp Ala Leu Arg Ser His Ile Arg Thr His Thr Gly Glu Lys
                85                  90                  95

Pro Phe Ala Cys Asp Ile Cys Gly Arg Lys Phe Ala Arg Ser Asp Asn
            100                 105                 110

Leu Ser Glu His Thr Lys Ile His Thr Gly Gly Ser Gln Leu Val Lys
        115                 120                 125
```

Ser Glu Leu Glu Glu Lys Lys Ser Glu Leu Arg His Lys Leu Lys Tyr
130                 135                 140

Val Pro His Glu Tyr Ile Glu Leu Ile Glu Ile Ala Arg Asn Ser Thr
145                 150                 155                 160

Gln Asp Arg Ile Leu Glu Met Lys Val Met Glu Phe Phe Met Lys Val
                165                 170                 175

Tyr Gly Tyr Arg Gly Lys His Leu Gly Gly Ser Arg Lys Pro Asp Gly
                180                 185                 190

Ala Ile Tyr Thr Val Gly Ser Pro Ile Asp Tyr Gly Val Ile Val Asp
                195                 200                 205

Thr Lys Ala Tyr Ser Gly Gly Tyr Asn Leu Pro Ile Gly Gln Ala Arg
210                 215                 220

Glu Met Gln Arg Tyr Val Glu Glu Asn Gln Thr Arg Asn Lys His Ile
225                 230                 235                 240

Asn Pro Asn Glu Trp Trp Lys Val Tyr Pro Ser Ser Val Thr Glu Phe
                245                 250                 255

Lys Phe Leu Phe Val Ser Gly His Phe Lys Gly Asn Tyr Lys Ala Gln
                260                 265                 270

Leu Thr Arg Leu Asn His Ile Thr Asn Cys Asn Gly Ala Val Leu Ser
            275                 280                 285

Val Glu Glu Leu Leu Ile Gly Gly Glu Met Ile Lys Ala Gly Thr Leu
290                 295                 300

Thr Leu Glu Glu Val Arg Arg Lys Phe Asn Asn Gly Glu Ile Asn Phe
305                 310                 315                 320

<210> SEQ ID NO 67
<211> LENGTH: 63
<212> TYPE: PRT
<213> ORGANISM: Unknown
<220> FEATURE:
<223> OTHER INFORMATION: Description of Unknown:
      DKK4 sequence

<400> SEQUENCE: 67

Asp Leu His Gly Ala Arg Lys Gly Ser Gln Cys Leu Ser Asp Thr Asp
1               5                   10                  15

Cys Asn Thr Arg Lys Phe Cys Leu Gln Pro Arg Asp Glu Lys Pro Phe
            20                  25                  30

Cys Ala Thr Cys Arg Gly Leu Arg Arg Arg Cys Gln Arg Asp Ala Met
        35                  40                  45

Cys Cys Pro Gly Thr Leu Cys Val Asn Asp Val Cys Thr Thr Met
    50                  55                  60

<210> SEQ ID NO 68
<211> LENGTH: 63
<212> TYPE: PRT
<213> ORGANISM: Unknown
<220> FEATURE:
<223> OTHER INFORMATION: Description of Unknown:
      DKK2 sequence

<400> SEQUENCE: 68

Lys Gly Lys Asn Leu Gly Gln Ala Tyr Pro Cys Ser Ser Asp Lys Glu
1               5                   10                  15

Cys Glu Val Gly Arg Tyr Cys His Ser Pro His Gln Gly Ser Ser Ala
            20                  25                  30

Cys Met Val Cys Arg Arg Lys Lys Lys Arg Cys His Arg Asp Gly Met
        35                  40                  45

```
Cys Cys Pro Ser Thr Arg Cys Asn Asn Gly Ile Cys Ile Pro Val
        50                  55                  60

<210> SEQ ID NO 69
<211> LENGTH: 66
<212> TYPE: PRT
<213> ORGANISM: Unknown
<220> FEATURE:
<223> OTHER INFORMATION: Description of Unknown:
      DKK1 sequence

<400> SEQUENCE: 69

Gln Thr Ile Asp Asn Tyr Gln Pro Tyr Cys Ala Glu Asp Glu Glu
1               5                   10                  15

Cys Gly Thr Asp Glu Tyr Cys Ala Ser Pro Thr Arg Gly Gly Asp Ala
                20                  25                  30

Gly Val Gln Ile Cys Leu Ala Cys Arg Lys Arg Arg Lys Arg Cys Met
            35                  40                  45

Arg His Met Cys Cys Pro Gly Asn Tyr Cys Lys Asn Gly Ile Cys Val
        50                  55                  60

Ser Ser
65

<210> SEQ ID NO 70
<211> LENGTH: 62
<212> TYPE: PRT
<213> ORGANISM: Unknown
<220> FEATURE:
<223> OTHER INFORMATION: Description of Unknown:
      IBS sequence

<400> SEQUENCE: 70

Gly Asp Glu Glu Gly Arg Arg Ser His Glu Cys Ile Ile Asp Glu Asp
1               5                   10                  15

Cys Gly Pro Ser Met Tyr Cys Gln Phe Ala Ser Phe Gln Tyr Thr Cys
                20                  25                  30

Gln Pro Cys Arg Gly Gln Arg Met Leu Cys Thr Arg Asp Ser Glu Cys
            35                  40                  45

Cys Gly Asp Gln Leu Cys Val Trp Gly His Cys Thr Lys Met
        50                  55                  60

<210> SEQ ID NO 71
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 71
gaaaggggct g                                                         11

<210> SEQ ID NO 72
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 72
cagttgtaac tg                                                        12
```

ANTI-CANCER AND ANTI-INFLAMMATORY THERAPEUTICS AND METHODS THEREOF

PRIORITY CLAIMS AND RELATED PATENT APPLICATIONS

This application claims the benefit of priority from U.S. Provisional Application Ser. No. 62/243,612, filed on Oct. 19, 2015, 62/281,702, filed on Jan. 21, 2016, and 62/380,525, filed Aug. 29, 2016, the entire content of each of which is incorporated herein by reference in its entirety for all purposes.

STATEMENT REGARDING FEDERALLY FUNDED RESEARCH OR DEVELOPMENT

This invention was made with government support under Grant Nos. DK038772 and DK060051 awarded by the National Institutes of Health. The Government has certain rights in the invention.

SEQUENCE LISTING

The instant application contains a Sequence Listing which has been submitted electronically in ASCII format and is hereby incorporated by reference in its entirety. Said ASCII copy, created on Jun. 22, 2018, is named UMMC12-40US2 SL.txt and is 28,489 bytes in size.

TECHNICAL FIELD OF THE INVENTION

The invention generally relates to anti-tumor and anti-inflammatory therapeutics and methods. More particularly, the invention relates to novel therapeutics based on DKK3b regulation of β-TrCP E3 Ubiquitin activity and on newly identified component of the Wnt pathway that regulates trafficking of β-catenin to the cell nucleus. The invention also relates to pharmaceutical compositions and methods of use based thereon for treating cancers and tumors and for treating inflammatory diseases and conditions.

BACKGROUND OF THE INVENTION

Suppressed Dickkopf-3 (DKK3) expression is a hallmark of many human cancers and expression levels are inversely related to tumor virulence (e.g., in prostate cancer and ovarian cancer). The Dickkopf family of secreted glycoproteins is composed of four members that first appeared in early metazoans as key regulators of the Wnt/β-Catenin signaling pathway. (Kawano et al. 2003 *Journal of Cell Science* 116, 2627-2634; Guder et al. 2006 *Development* 133, 901-911; Monaghan et al. 1999 *Mech Dev* 87, 45-56; Niehrs 2006 *Oncogene* 25, 7469-7481.) Three family members DKK1, DKK2 and DKK4 block Wnt signaling by binding to the LRP5/6 subunit of the Wnt receptor, Frizzled. (Zorn 2001 *Current Biology: CB* 11, R592-595; Ahn et at 2011 *Developmental Cell* 21, 862-873; Cheng et al. 2011 *Nature Structural & Molecular Biology* 18, 1204-1210.) The remaining family member, DKK3, evolved separately, retains two cysteine rich domains found in other family members, but does not modulate Wnt receptor activation. (Guder et al. 2006 *Development* 133, 901-911; Fedders et al. 2004 *Development Genes and Evolution* 214, 72-80; Krupnik et al 1999 *Gene* 238, 301-313; Mao et al. 2003 *Gene* 302, 179-183; Wu et al. 2000 *Current Biology: CB* 10, 1611-1614.)

The tumor suppressor gene, DKK3, is silenced, in most cancers by hypermethylation of CpG islands located in exon 2 and the degree of loss of DKK3 is directly related to tumor aggression. DKK3 is the best-known tumor suppressor in the family despite its structural inability to block Wnt binding. (Veeck et al. 2012 *Biochim Biophys Acta* 1825, 18-28; Fujii et al. 2014 *Acta Med Okayama* 68, 63-78.) Ectopic over-expression of DKK3 slows β-catenin driven cancer cell proliferation, although the mechanism of DKK3 action remains unknown. Surprisingly, targeted deletion of the mouse Dkk3 gene, which disrupts the well-established secreted DKK3 isoform, failed to provide a direct link between DKK3 and the Wnt/β-catenin signaling pathway. The $Dkk^{tm1Cni}$ mutant mouse is viable, fertile, shows no increase in cancer susceptibility and no β-catenin signaling defects. (Gotze et al. 2010 *Int J Cancer* 126, 2584-2593; Veeck et al 2004 *Br J Cancer* 91, 707-713; Gu et al. 2011 *World J Gastroenterol* 17, 3810-3817; Lee et al. 2009 *Int J Cancer* 124, 287-297; Yue et al. 2008 *Carcinogenesis* 29, 84-92; Hsieh et al. 2004 *Oncogene* 23, 9183-9189; Idel et al. 2006 *Mol Cell Biol* 26, 2317-2326.) This Dkk3 gene mutant also fails to phenocopy other Dickkopf deletion mutants or mutants of the Wnt/β-catenin pathway. (Lewis et at 2008 *Development* 135, 1791-1801; Pietila et al. 2013 *Cell stem cell* 12, 204-214; Mukhopadhyay et al 2006 *Development* 133, 2149-2154; Li et al 2005 *Nature Genetics* 37, 945-952; Kerkela et al. 2008 *The Journal of Clinical Investigation* 118, 3609-3618; Xie et al. 2011 *Genesis* 49, 98-102; Sieber et al. 2004 *Cancer Res* 64, 8876-8881; Chia et al. 2009 *Genetics* 181, 1359-1368; Guardavaccaro et al. 2003 *Developmental Cell* 4, 799-812; Nakayama et al. 2003 *Proc Natl Acad Sci USA* 100, 8752-8757.)

β-transducin repeat-containing protein (β-TrCP) is a key regulatory molecule of the ubiquitin-proteasome system (UPS) with roles in cellular processes that are intimately related to tumorigenesis, including proliferation, differentiation, and apoptosis. Cancers associated with β-TrCP dysregulation and the aberrant proteolysis of its substrates are found in the breast, colon, liver, pancreatic, melanoma, stomach and prostate. (Frescas, et al. 2008 *Nature Reviews Cancer* 8, 438-449; Miyamoto, et al. 2015 *Science* 349 (6254): 1351-6; Fong, et al. 2015 *Nature* 525(7570): 538-42.)

β-TrCP is a key player in the S and G2 DNA-damage response checkpoint, the main function of which is to mediate cell cycle arrest allowing time to repair DNA lesions. In addition, the mammalian protein β-TrCP and its *Drosophila* homolog Slimb have been implicated in three crucial signal transduction pathways, NF-κB, Wnt, and Hedgehog. (Maniatis 1999 *Genes & Development* 13:505-510.)

β-TrCP is one of the best-characterized mammalian F-box proteins. The F-box proteins provide a mechanism for specificity of SCF ligase complexes (Skp, Cdc53/Cull, F-box). F-box proteins recruit target substrates to the complex, which allows an E2 enzyme to transfer a ubiquitin from a ubiquitin-E1 complex to the target substrate protein. β-TrCP functions in diverse pathways by targeting hundreds of potential substrates. (Low 2014 *Sci Signal.* 16:7(356).) Notable examples include: (1) β-TrCP mediates degradation of CD4 via its interaction with HIV-1 factor, Vpu; (2) βTrCP targets phosphorylated IκBα for degradation, thereby activating NF-κB; (3) β-TrCP modulates Wnt signal transduction by targeted degradation of phosphorylated β-catenin; (4) β-TrCP regulates DNA-damage response checkpoint by targeting the Cdc25 dual-specificity phosphatases, and subsequently claspin and WEE1.

There remains an urgent need for novel therapeutics and methods of treatment for cancers and inflammatory diseases and conditions.

SUMMARY OF THE INVENTION

The invention is based on the unexpected discovery of novel therapeutics based on DKK3b regulation of β-TrCP E3 Ubiquitin activity and on newly identified component of the Wnt pathway that regulates trafficking of β-catenin to the cell nucleus. The invention also relates to pharmaceutical compositions and methods of use based thereon for treating cancers and tumors and for treating inflammatory diseases and conditions.

Members of the Dickkopf (Dkk) family of Wnt antagonists participate in axial patterning and cell fate determination by interrupting Wnt-induced receptor assembly. Epigenetic silencing of Dkk3, the one family member that does not block Wnt receptor activation, is linked to cancer, and its ectopic expression halts cancer growth. Disclosed herein is a previously unknown, essential component of the Wnt/β-catenin signaling pathway that governs the quantity of β-catenin delivered to the cell nucleus. This intracellular inhibitor of β-catenin signaling (IBS) is transcribed from a second transcriptional start site adjacent to exon 3 of the Dkk3 gene and is required for early mouse development.

IBS captures β-catenin destined for the nucleus in a complex with β-TrCP that is bound to the actin cytoskeleton and unavailable for nuclear translocation. This adds a new dimension of regulation to one of the most studied signal transduction pathways in the cell. The present invention provides a novel, completely untapped therapeutic target for arresting the dysregulated β-catenin signaling that drives cell proliferation in many cancers.

In one aspect, the invention generally relates to an isolated recombinant human inhibitor of β-catenin signaling protein, or a variant thereof.

In another aspect, the invention generally relates to a fusion protein comprising inhibitor of β-catenin signaling protein, or a variant thereof.

In yet another aspect, the invention generally relates to a host cell transformed with an isolated recombinant human inhibitor of β-catenin signaling protein, or a variant or a fusion protein thereof.

In yet another aspect, the invention generally relates to an isolated nucleic acid molecule comprising a polynucleotide sequence that encodes inhibitor of β-catenin signaling protein, or a variant thereof.

In yet another aspect, the invention generally relates to a recombinant virus genetically modified to express human inhibitor of β-catenin signaling protein, or a variant thereof.

In yet another aspect, the invention generally relates to a recombinant transgene comprising a polynucleotide that encodes human inhibitor of β-catenin signaling protein, or a variant thereof.

In yet another aspect, the invention generally relates to a pharmaceutical composition comprising a recombinant virus genetically modified to express human inhibitor of β-catenin signaling protein, or a variant thereof, and a pharmaceutically acceptable carrier.

In yet another aspect, the invention generally relates to a method for treating cancer or inhibiting tumor progression in a subject in need thereof, comprising administering to the subject a pharmaceutical composition comprising a recombinant virus genetically modified to express human inhibitor of β-catenin signaling protein, or a variant thereof, and a pharmaceutically acceptable carrier.

In yet another aspect, the invention generally relates to a pharmaceutical composition comprising human inhibitor of β-catenin signaling, or a variant or a fusion protein thereof, and a pharmaceutically acceptable carrier.

In yet another aspect, the invention generally relates to a method for treating cancer or inhibiting tumor progression in a subject in need thereof, comprising administering to the subject a pharmaceutical composition comprising inhibitor of β-catenin signaling protein, or a variant or a fusion protein thereof.

In yet another aspect, the invention generally relates to a method for inducing a tumor-suppression effect in a subject in need thereof, comprising administering to the subject a pharmaceutical composition comprising inhibitor of β-catenin signaling protein, or a variant or a fusion protein thereof.

In yet another aspect, the invention generally relates to a method for establishing susceptibility of a cancer patient to tumor-suppression treatment by inhibitor of β-catenin signaling protein, or a variant or a fusion protein thereof.

In yet another aspect, the invention generally relates to a method for inducing a tumor-suppression effect in a subject in need thereof, comprising administering to the subject a pharmaceutical composition comprising a messenger RNA (mRNA) encoding the human inhibitor of β-catenin signaling protein, or a variant thereof, and a pharmaceutically acceptable carrier.

In yet another aspect, the invention generally relates to a method for treating cancer or inhibiting tumor progression in a subject in need thereof, comprising administering to the subject a pharmaceutical composition comprising a recombinant virus genetically modified to express human DKK3b protein and a pharmaceutically acceptable carrier. Exemplary cancer or tumor that may be treated include: carcinoma, lymphoma, blastoma, sarcoma, liposarcoma, neuroendocrine tumor, mesothelioma, schwanoma, meningioma, adenocarcinoma, melanoma, leukemia, lymphoid malignancy, squamous cell cancer, epithelial squamous cell cancer, lung cancer, small-cell lung cancer, non-small cell lung cancer, adenocarcinoma of the lung, squamous carcinoma of the lung, cancer of the peritoneum, hepatocellular cancer, gastric or stomach cancer, gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, testicular cancer, esophageal cancer, a tumor of the biliary tract, and head and neck cancer.

In certain preferred embodiments, the method disclosed herein for treating cancer further includes administering to the subject a pharmaceutical composition comprising a second active anti-tumor agent. The second active anti-tumor agent may be a small molecule, a chemotherapeutic agent, a peptide, a polypeptide or protein, an antibody, an antibody-drug conjugate, an aptamer or nucleic acid molecule.

In yet another aspect, the invention generally relates to a method for treating inflammatory diseases or inhibiting inflammatory diseases in a subject in need thereof, comprising administering to the subject a pharmaceutical composition comprising a recombinant virus genetically modified to express human inhibitor of β-catenin signaling protein, or a variant thereof, and a pharmaceutically acceptable carrier.

In yet another aspect, the invention generally relates to a method for treating an inflammatory disease or condition in a subject in need thereof, comprising administering to the subject a pharmaceutical composition comprising a recombinant virus genetically modified to express human DKK3b protein or a variant or a fusion protein thereof and a pharmaceutically acceptable carrier.

Exemplary inflammatory diseases or conditions include any disease or condition characterized by an inflammatory or allergic process as is known in the art, such as inflammation, acute inflammation, chronic inflammation, respiratory disease, atherosclerosis, psoriasis, dermatitis, restenosis, asthma, allergic rhinitis, atopic dermatitis, septic shock, rheumatoid arthritis, inflammatory bowel disease, inflammatory pelvic disease, pain, ocular inflammatory disease, celiac disease, Leigh syndrome, glycerol kinase deficiency, familial eosinophilia, autosomal recessive spastic ataxia, laryngeal inflammatory disease; tuberculosis, chronic cholecystitis, bronchiectasis, silicosis and other pneumoconioses.

In certain preferred embodiments, the method disclosed herein for treating an inflammatory disease or condition further includes administering to the subject a pharmaceutical composition comprising a second active anti-inflammatory agent. The second active anti-inflammatory agent may be a small molecule, a peptide, a polypeptide or protein, an antibody, an antibody-drug conjugate, an aptamer or nucleic acid molecule.

In yet another aspect, the invention generally relates to a pharmaceutical composition suitable for use in for treating cancer or inhibiting tumor progression, comprising human DKK3b protein or a variant or a fusion protein thereof and a pharmaceutically acceptable carrier.

In yet another aspect, the invention generally relates to a pharmaceutical composition comprising a messenger RNA (mRNA) encoding the human inhibitor of β-catenin signaling protein, or a variant thereof, and a pharmaceutically acceptable carrier.

In yet another aspect, the invention generally relates to a pharmaceutical composition suitable for use in for treating inflammatory disease or condition, comprising human DKK3b protein or a variant or a fusion protein thereof and a pharmaceutically acceptable carrier.

BRIEF DESCRIPTION OF THE DRAWINGS

FIG. 1. Organization of functional domains of the secreted, cell penetrating IBS molecules. The ProSecreted_cpIBS is the pro form of the translation product prior to proteolytic cleavage of the membrane spanning residues recognized by the SRP (shown in grey). The mature _cpIBS is composed of the variable residues retained after release of the membrane spanning SRP residues, the cell-penetrating domain (cp) and variable domains of IBS.

FIG. 2. β-catenin Signaling in presence of different spent media from CHO cells harboring different PTEN_cp_IBS variants. Data are the means+/− SE of triplicate wells.

FIG. 3. Schematic map of secreted ScpIBS mutants. SRP, signal recognition particle domain; cp, cell penetrating domain; N-1, required N-terminal amino acids 1-10; C-1, cysteine rich domain 1; C-2, cysteine rich domain 2; Ct, required C-terminus amino acids 270-280.

FIG. 4. Schematic of functional domains of the bacterial expressed unfolded, cell penetrating (cp) IBS molecules. The cpIBS is a fusion protein of an 11-residue long synthetic cp domain to the coding sequence of human IBS. The cpIBS$^{122}$ is composed of residues 1-122 of IBS with residues 270-280 appended to the C-terminus.

FIG. 5. Schematic map of secreted ScpIBS mutants. cp, cell penetrating domain; N-1, required N-terminal amino acids 1-10; C-1, cysteine rich domain 1; C-2, cysteine rich domain 2; Ct, required C-terminus amino acids 270-280.

FIG. 6. Identification of multiple transcripts originating for the Dkk3 gene locus. a. Schematic diagram of the Dkk3 gene (NC_000073.6) in the wild type and Dkk3$^{tm1Cni}$ mutant mouse. Initiator methionine for Dkk3 (NM_0154814) and D2p29 (AF245040) indicated by arrows. b. Immunoblot analysis of DKK3 isoforms in the brain of Dkk3$^{+/+}$ and Dkk3$^{tm1Cni}$ mouse. c. Quantitative PCR analysis Dkk3 containing exon2 and exon 3 transcripts in total brain RNA in wild type and Dkk3$^{tm1Cni}$. Arrows indicate PCR primer sites (Error bars represent SE of three individuals). d. Schematic diagram of rat Dkk3 intron 2:luciferase constructs used for promoter localization. Arrows show the orientation and location of intron 2 segments upstream of exon 3 (Error bars represent SE of three independent experiments). e. Chromatin immunoprecipitation of RNA pol 2 and TBP bound to the ~130 nt of intron 2 adjacent to exon 3 in the rat astrocyte Dkk3 gene (Error bars represent the SE of three independent experiments).

FIG. 7. Analysis of the biology of the TSS2 in the Dkk3 gene of the ZFN gene-edited Dkk3$^{CFP/+}$ mouse. a. DNA methyltransferase inhibition increases TSS2-driven CFP in gene-edited cells. b. Phenotype ratios for the Dkk3$^{CFP}$ allele in C57B16j and out-bred CD1 mice. c. TSS2-driven CFP expression in representative tissues of the Dkk3$^{CFP/+}$ mouse.

FIG. 8. IBS regulation of cell proliferation and apoptosis. a. Comparison of the effects of IBS and DKK3 on PC3 cell proliferation (Error bars represent the SE of three independent experiments). b. IBS arrests cell proliferation at the G0/G1 phase of the cell cycle (Error bars represent the SE of three independent experiments). c. Cell permeant IBS (TAT-IBS) initiated cell loss is blocked by inhibition of JNK activity and is independent of cell cycle arrest (Error bars represent the SE of three independent experiments). d. TAT-IBS induced pro-apoptotic Cleaved Caspase 3 by activation of the JNK pathway in PC3 cells.

FIG. 9. IBS and β-catenin signaling. a. Comparison of the cellular distribution of TAT-IBS and transfected Flag-IBS in HEK293 cells. b. IBS blocks Wnt/β-catenin stimulated cell proliferation without altering basal cell proliferation (Data represent the means of four closely agreeing (±10%) independent experiments) Open bar—day 0; colored bars—day 3. c. TAT-IBS antagonizes primary and secondary β-catenin dependent gene expression (Error bars represent the SE of three independent experiments). d. TAT-IBS inhibits β-catenin dependent malignant cell migration (Error bars represent the SE of three independent experiments).

FIG. 10. Characterization of the molecular interactions between IBS, βTrCP and the β-catenin signaling pathway. a. Expression levels of epitope tagged βTrCP, IBS and the constitutively active S33Y mutant β-catenin in HEK293 cells. b. Co-immunoprecipitation of IBS interacting βTrCP and β-catenin. Individual epitope tagged targets were immune precipitated and analyzed by immunoblot with epitope specific antibodies. c. IBS interacts with native transcriptionally active β-catenin, but not with phospho-β-catenin or GSK3β. d. IBS blocks the cytoplasmic increase and nuclear import and increases microfilament bound β-catenin while stabilizing the total cell content (Data are the means±SE of three independent experiments). The actin cytoskeleton was visualized using AlexaFluor$^{488}$-phalloidin e. Rapid clearance of nuclear associated β-catenin by TAT-IBS. (Error bars represent the SE of three independent experiments). Numbers in parentheses indicate cell counts at each time point.

FIG. 11. Schematic diagram of the novel regulatory role of IBS in the Wnt/β-catenin signaling pathway. DSH, Disheveled; GSK3β, Glycogen synthase kinase 3 beta; CK1, Casein kinase 1; PP2A, Protein Phosphatase 2A; APC, Adenomatous Polyposis Coli; βTrCP, β-Transducin Repeat-Containing Protein.

FIG. 12. Table 1. Primers used in this study (SEQ ID NOS 5-50, respectively, in order of appearance).

FIG. 13. Table 2. Off-target analysis of ZFN gene edited Dkk3$^{CFP}$ mouse (Founder #19). Mouse C57b16 genome GRCm38 (SEQ ID NOS 51-61, respectively, in order of appearance).

FIG. 14. Comparison of Dkk3 isoforms in mouse astrocytes. a. Alignment of the amino acid sequences of DKK3 (SEQ ID NO: 62) and D2p29 (SEQ ID NO: 63). b. Effects of Furin proteolysis on DKK3 isoforms in astrocytes. Image analysis software (Odyssey, LI-COR) was used to measure individual DKK3 bands and the data normalized to tubulin. Data represent 3 independent cell preparations/furin digests.

FIG. 15. Exon specific qPCR analysis of Dkk3 transcripts in rat astrocytes. Validation of the Dkk3 exon 2 (SEQ ID NOS 41-42, respectively, in order of appearance) and exon 3 (SEQ ID NOS 43-44, respectively, in order of appearance) primer sets. Dkk3 mRNA levels were normalized to GAPDH mRNA. Data (mean±SE) from 3 independent experiments.

FIG. 16. ZFN target in intron 2 of the Dkk3 gene. a. Sequence and location of the target sequence relative to exon 3 (SEQ ID NO: 64). b. Complete amino acid sequences of the epitope tagged ZFNs (SEQ ID NOS 71, 65, 72, and 66, respectively, in order of appearance).

FIG. 17. Schematic Diagram of the ZFN mediated gene editing of the mouse Dkk3 gene. a. Organization of the first 4 exons of the wild type Dkk3 locus. TSS1, transcriptional start site 1; TSS2, transcriptional start site 2. b. Schematic diagram of the HR donor. c. Schematic diagram of the gene edited Dkk3$^{CFP}$ locus. Genotyping PCR primers indicated by arrows (Table 1). Agarose gel confirmation of CFP insertion at the ZFN target locus in the Dkk3$^{CFP}$ mouse.

FIG. 18. Sox2 promoter-Cre Rescue of the Lethal Phenotype of the Dkk3$^{CFP}$ mouse. a. Schematic diagram of the Dkk3$^{CFP}$ locus. Arrow heads indicate the location of PCR primers DKSF and DKSR. b. Schematic diagram of Dkk3$^{CFP}$ locus after Cre recombination. c. Schematic diagram of the Dkk3' locus. d. Agarose gel analysis of PCR products produced from 6-week old mouse DNA of a representative homozygote gene edited (#131), a wild type (#586), and a heterozygote gene edited (#781).

FIG. 19. Effects of loss of IBS by bi-allelic insertion diversion the Dkk3 TSS2 in MEFs. a. MEFs were prepared from 16 d old heterozygous Dkk3$^{CFP/+}$ embryos and the wild type Dkk3 allele was re-edited with ZFNs and a mCherry HR donor. Bi-allelic gene-edited, IBS knockout, Dkk3$^{CFP/mCherry}$ cells that express both CFP and mCherry were isolated by FACS. Immunoblot analysis of the DKK3 isoforms present in the homozygous Dkk3$^{CFP/mCherry}$ cells. b. qPCR analysis of Dkk3 transcripts present in wild-type and IBS knockout MEFS. Transcript abundance measured by the DDCT method using GAPDH as the control. Data represent the means±se of triplicate dishes. c. qPCR analysis of c-Myc and Cyclin D1 transcripts present in wild-type and IBS knockout MEFS. Transcript abundance measured by the ΔΔCT method using GAPDH as the control. Data represent the means±se of triplicate dishes.

FIG. 20. Domain organization of ScpIBS and β-catenin signaling.

FIG. 21. Accumulated mutation/deletion/truncation evaluation of the essential domains of the IBS protein.

FIG. 22. Effects of the N-1 domain of the DKK family on β-catenin signaling (SEQ ID NOS 67-70, respectively, in order of appearance).

FIG. 24. IBS increases microfilament-bound β-TRCP substrates. SOAS-2 cells were stimulated with the GSK3 inhibitor, LiCl, to stabilize β-catenin and mimic Wnt-1 pathway activation. Untreated and IBS-treated microfilament fractions of cell lysates show that short-term (90 min.) IBS replacement resulted in β-TrCP, Erk1/2, NF-κB, and p38 proteins complexes bound to microfilaments. Thus, the inhibitory complex formed between IBS, β-TrCP and β-TrCP target substrates interrupts the nuclear import and defines the molecular basis for the silencing of β-TrCP substrate signaling by IBS.

DEFINITIONS

Figure 23:
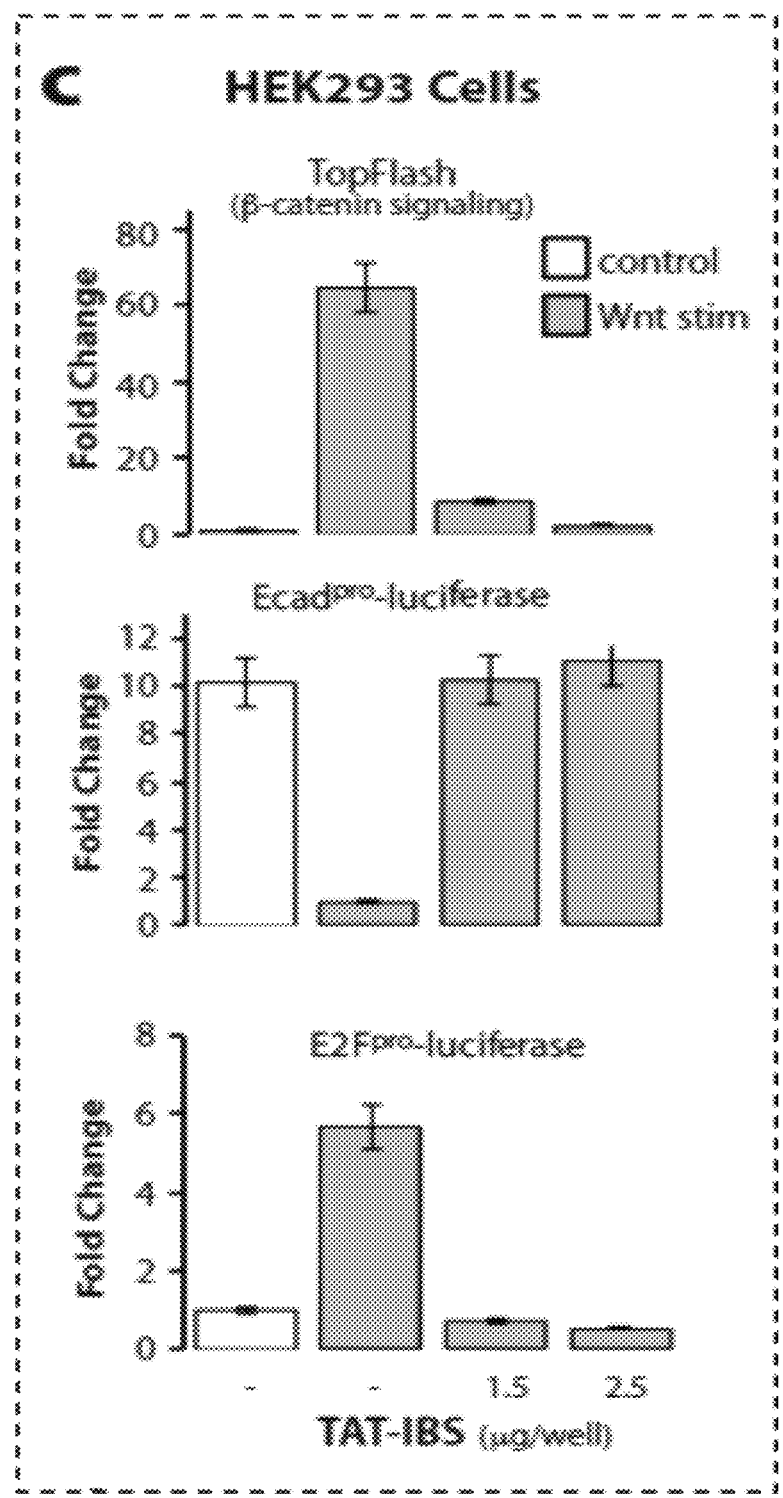
FIG. 23. TAT-IBS antagonizes primary and secondary β-catenin and NF-κB-dependent gene expression. A) TAT-IBS blocks an NF-κB (p65)-responsive promoter driving luciferase reporter in HEK293 cells that was stimulated by Wnt-1 transfection (shaded bars). B) TAT-IBS restores transcriptional activity of Elf3-luciferase, a reporter of epithelial differentiation that is suppressed by Wnt-1 stimulation. C) (Data previously disclosed in UMMC 12-40PR2). TAT-IBS restores E-Cadherin (CDH1)-promoter activity in Wnt-1 stimulated cells (middle chart). TopFlash and E2F-luciferase reporters are dependent on β-TrCP substrates, β-catenin and E2F, respectively (top and bottom charts). TAT-IBS blocks transcriptional activation by Wnt-1 stimulation of both reporters.

The definitions below are provided as summaries of concepts that are commonly understood by one of ordinary skill in the relevant art and are provided for the purposes of understanding of the subject matter disclosed herein. The definitions are not meant to be limitations of the invention or claims herein.

As used herein, the term "antibody" refers to molecules that are capable of binding an epitope or antigenic determinant. The term is meant to include whole antibodies and antigen-binding fragments thereof, including single-chain antibodies. The antibodies can be from any animal origin. Preferably, the antibodies are mammalian, e.g., human, murine, rabbit, goat, guinea pig, camel, horse and the like, or other suitable animals. Antibodies may recognize polypeptide or polynucleotide antigens. The term includes active fragments, including for example, an antigen binding fragment of an immunoglobulin, a variable and/or constant region of a heavy chain, a variable and/or constant region of a light chain, a complementarity determining region (cdr), and a framework region. The terms include polyclonal and monoclonal antibody preparations, as well as preparations including hybrid antibodies, altered antibodies, chimeric antibodies, hybrid antibody molecules, F(ab)$_2$ and F(ab) fragments; Fv molecules (for example, noncovalent heterodimers), dimeric and trimeric antibody fragment constructs; minibodies, humanized antibody molecules, and any functional fragments obtained from such molecules, wherein such fragments retain specific binding.

As used herein, the term "humanized" antibodies refer to a molecule having an antigen binding site that is substantially derived from an immunoglobulin from a non-human species and the remaining immunoglobulin structure of the molecule based upon the structure and/or sequence of a human immunoglobulin. The antigen binding site may comprise either complete variable domains fused onto constant domains or only the complementarity determining regions (CDRs) grafted onto appropriate framework regions in the variable domains. Antigen binding sites may be wild type or modified by one or more amino acid substitutions, e.g., modified to resemble human immunoglobulin more closely. Some forms of humanized antibodies preserve all CDR sequences (e.g., a humanized mouse antibody which contains all six CDRs from the mouse antibodies). Other forms of humanized antibodies have one or more CDRs (one, two, three, four, five, six) that are altered with respect to the original antibody.

The term "binds specifically," in the context of antibody binding, refers to high avidity and/or high affinity binding of an antibody to a specific epitope. Hence, an antibody that binds specifically to one epitope (a "first epitope") and not to another (a "second epitope") is a "specific antibody." An antibody specific to a first epitope may cross react with and bind to a second epitope if the two epitopes share homology or other similarity. The term "binds specifically," in the context of a polynucleotide, refers to hybridization under stringent conditions. Conditions that increase stringency of both DNA/DNA and DNA/RNA hybridization reactions are widely known and published in the art (Curr. Prot. Molec. Biol., John Wiley & Sons (2001)).

As used herein, the term "antigen" refers to a molecule capable of being bound by an antibody. An antigen is additionally capable of being recognized by the immune system and/or being capable of inducing a humoral immune response and/or cellular immune response leading to the activation of B- and/or T-lymphocytes. This may, however, require that, at least in certain cases, the antigen contains or is linked to a Th cell epitope and is given in adjuvant. An antigen can have one or more epitopes (B- and/or T-cell epitopes). The specific reaction referred to above is meant to indicate that the antigen will preferably react, typically in a highly selective manner, with its corresponding antibody or TCR and not with the multitude of other antibodies or TCRs which may be evoked by other antigens. Antigens as used herein may also be mixtures of several individual antigens.

As used herein, the term "epitope" refers to basic element or smallest unit of recognition by an individual antibody or T-cell receptor, and thus the particular domain, region or molecular structure to which said antibody or T-cell receptor binds. An antigen may consist of numerous epitopes while a hapten, typically, may possess few epitopes.

As used herein, the term "nucleic acid molecule," "nucleotide," "oligonucleotide," "polynucleotide," and "nucleic acid" are used interchangeably herein to refer to polymeric forms of nucleotides of any length. They can include both double- and single-stranded sequences and include, but are not limited to, cDNA from viral, prokaryotic, and eukaryotic sources; mRNA; genomic DNA sequences from viral (e.g., DNA viruses and retroviruses) or prokaryotic sources; RNAi; cRNA; antisense molecules; ribozymes; and synthetic DNA sequences. The term also captures sequences that include any of the known base analogs of DNA and RNA.

As used herein, the term "promoter" refers to a DNA regulatory region capable of binding RNA polymerase in a mammalian cell and initiating transcription of a downstream (3' direction) coding sequence operably linked thereto. For purposes of the present invention, a promoter sequence includes the minimum number of bases or elements necessary to initiate transcription of a gene of interest at levels detectable above background. Within the promoter sequence may be a transcription initiation site, as well as protein binding domains (consensus sequences) responsible for the binding of RNA polymerase. Eukaryotic promoters will often, but not always, contain "TATA" boxes and "CAT" boxes. Promoters include those that are naturally contiguous to a nucleic acid molecule and those that are not naturally contiguous to a nucleic acid molecule. Additionally, the term "promoter" includes inducible promoters, conditionally active promoters such as a cre-lox promoter, constitutive promoters, and tissue specific promoters.

As used herein, the term "transfected" means possessing introduced DNA or RNA, with or without the use of any accompanying facilitating agents such as lipofectamine. Methods for transfection that are known in the art include calcium phosphate transfection, DEAE dextran transfection, protoplast fusion, electroporation, and lipofection.

As used herein, the term "expression of a nucleic acid molecule" refers to the conversion of the information contained in the nucleic acid molecule into a gene product. The gene product can be the direct transcriptional product of a gene (e.g., mRNA, tRNA, rRNA, antisense RNA, ribozyme, structural RNA, or any other type of RNA) or a peptide or polypeptide produced by translation of an mRNA. Gene products also include RNAs that are modified by processes such as capping, polyadenylation, methylation, and editing; and proteins modified by, for example, methylation, acetylation, phosphorylation, ubiquitination, ADP-ribosylation, myristilation, and glycosylation.

As used herein, the term "host cell" refers to an individual cell or a cell culture that can be or has been a recipient of any recombinant vector(s) or isolated polynucleotide(s). Host cells include progeny of a single host cell, and the progeny may not necessarily be completely identical (in morphology or in total DNA complement) to the original parent cell due to natural, accidental, or deliberate mutation and/or change. A host cell includes cells transfected or infected in vivo or in vitro with a recombinant vector or a polynucleotide of the invention. A host cell that comprises a recombinant vector of the invention may be called a "recombinant host cell."

As used herein, the term "biologically active" entity, or an entity having "biological activity," is one having structural, regulatory, or biochemical functions of a naturally occurring molecule or any function related to or associated with a metabolic or physiological process. Biologically active polynucleotide fragments are those exhibiting activity similar, but not necessarily identical, to an activity of a polynucleotide of the present invention. The biological activity can include an improved desired activity, or a decreased undesirable activity. For example, an entity demonstrates biological activity when it participates in a molecular interaction with another molecule, such as hybridization, when it has therapeutic value in alleviating a disease condition, when it has prophylactic value in inducing an immune response, when it has diagnostic and/or prognostic value in determining the presence of a molecule, such as a biologically active fragment of a polynucleotide that can, for example, be detected as unique for the polynucleotide molecule, or that can be used as a primer in a polymerase chain reaction. A biologically active polypeptide or fragment thereof includes one that can participate in a biological reaction.

As used herein, the term "inflammatory condition(s)" refers to the group of conditions including, rheumatoid arthritis, osteoarthritis, juvenile idiopathic arthritis, psoriasis, allergic airway disease (e.g., asthma, rhinitis), inflammatory bowel diseases (e.g., Crohn's disease, colitis), endotoxin-driven disease states (e.g., complications after bypass surgery or chronic endotoxin states contributing to e.g.

chronic cardiac failure), and related diseases involving cartilage, such as that of the joints. Particularly the term refers to rheumatoid arthritis, osteoarthritis, allergic airway disease (e.g., asthma) and inflammatory bowel diseases.

As used herein, the term "cancer" refers to or describes the physiological condition in mammals that is typically characterized by unregulated cell growth. Examples of cancer include but are not limited to, carcinoma, lymphoma, sarcoma, blastoma and leukemia. More particular examples of such cancers include squamous cell carcinoma, lung cancer, pancreatic cancer, cervical cancer, bladder cancer, hepatoma, breast cancer, colon carcinoma, and head and neck cancer.

As used herein, the term "tumor" refers to any malignant or neoplastic cell.

As used herein, the terms "polypeptide" and "protein" are used interchangeably to refer to a polymer of amino acid residues, and are not limited to a minimum length. Thus, peptides, oligopeptides, dimers, multimers, and the like, are included within the definition. Both full-length proteins and fragments thereof are encompassed by the definition. The terms also include post-expression modifications of the polypeptide, for example, glycosylation, acetylation, phosphorylation, and the like. Furthermore, a "polypeptide" may refer to a protein which includes modifications, such as deletions, additions, and substitutions (generally conservative in nature), to the native sequence, as long as the protein maintains the desired activity. These modifications may be deliberate or may be accidental.

As used herein, the term "receptor" refers to proteins or glycoproteins or fragments thereof capable of interacting with another molecule, called the ligand. The ligand may belong to any class of biochemical or chemical compounds. The ligand is usually an extracellular molecule which, upon binding to the receptor, usually initiates a cellular response, such as initiation of a signal transduction pathway. The receptor need not necessarily be a membrane-bound protein.

As used herein, the term "recombinant," with respect to a nucleic acid molecule, means a polynucleotide of genomic, cDNA, viral, semisynthetic, and/or synthetic origin which, by virtue of its origin or manipulation, is not associated with all or a portion of the polynucleotide with which it is associated in nature. The term "recombinant", as used with respect to a protein or polypeptide, means a polypeptide produced by expression of a recombinant polynucleotide. The term "recombinant" as used with respect to a host cell means a host cell into which a recombinant polynucleotide has been introduced.

As used herein, the phrase "recombinant virus" refers to a virus that is genetically modified by the hand of man. The phrase covers any virus known in the art.

As used herein, the term "vector" refers to an agent (e.g., a plasmid or virus) used to transmit genetic material to a host cell or organism. A vector may be composed of either DNA or RNA.

As used herein, the term "interfering RNA" or "RNAi" or "interfering RNA sequence" refers to double-stranded RNA (i.e., duplex RNA) that is capable of reducing or inhibiting expression of a target gene (i.e., by mediating the degradation of mRNAs which are complementary to the sequence of the interfering RNA) when the interfering RNA is in the same cell as the target gene. Interfering RNA thus refers to the double-stranded RNA formed by two complementary strands or by a single, self-complementary strand. Interfering RNA may have substantial or complete identity to the target gene or may comprise a region of mismatch (i.e., a mismatch motif). The sequence of the interfering RNA can correspond to the full length target gene, or a subsequence thereof. Interfering RNA includes "small-interfering RNA" or "siRNA," e.g., interfering RNA of about 15-60, 15-50, or 15-40 (duplex) nucleotides in length, more typically about 15-30, 15-25, or 19-25 (duplex) nucleotides in length).

As used herein, the term "sample" refers to a sample from a human, animal, or to a research sample, e.g., a cell, tissue, organ, fluid, gas, aerosol, slurry, colloid, or coagulated material. The "sample" may be tested in vivo, e.g., without removal from the human or animal, or it may be tested in vitro. The sample may be tested after processing, e.g., by histological methods. "Sample" also refers, e.g., to a cell comprising a fluid or tissue sample or a cell separated from a fluid or tissue sample. "Sample" may also refer to a cell, tissue, organ, or fluid that is freshly taken from a human or animal, or to a cell, tissue, organ, or fluid that is processed or stored.

As used herein, the term an "isolated" or "substantially isolated" molecule (such as a polypeptide or polynucleotide) is one that has been manipulated to exist in a higher concentration than in nature or has been removed from its native environment. For example, a subject antibody is isolated, purified, substantially isolated, or substantially purified when at least 10%, or 20%, or 40%, or 50%, or 70%, or 90% of non-subject-antibody materials with which it is associated in nature have been removed. For example, a polynucleotide or a polypeptide naturally present in a living animal is not "isolated," but the same polynucleotide or polypeptide separated from the coexisting materials of its natural state is "isolated." Further, recombinant DNA molecules contained in a vector are considered isolated for the purposes of the present invention. Isolated RNA molecules include in vivo or in vitro RNA replication products of DNA and RNA molecules. Isolated nucleic acid molecules further include synthetically produced molecules. Additionally, vector molecules contained in recombinant host cells are also isolated. Thus, not all "isolated" molecules need be "purified."

As used herein, the term "purified" when used in reference to a molecule, it means that the concentration of the molecule being purified has been increased relative to molecules associated with it in its natural environment, or environment in which it was produced, found or synthesized. Naturally associated molecules include proteins, nucleic acids, lipids and sugars but generally do not include water, buffers, and reagents added to maintain the integrity or facilitate the purification of the molecule being purified. According to this definition, a substance may be 5% or more, 10% or more, 20% or more, 30% or more, 40% or more, 50% or more, 60% or more, 70% or more, 80% or more, 90% or more, 95% or more, 98% or more, 99% or more, or 100% pure when considered relative to its contaminants.

As used herein, "administration" of a disclosed compound encompasses the delivery to a subject of a compound as described herein, or a prodrug or other pharmaceutically acceptable derivative thereof, using any suitable formulation or route of administration, as discussed herein.

As used herein, the terms "effective amount" or "therapeutically effective amount" refer to that amount of a compound or pharmaceutical composition described herein that is sufficient to effect the intended application including, but not limited to, disease treatment, as illustrated below. In some embodiments, the amount is that effective for detectable killing or inhibition of the growth or spread of cancer cells; the size or number of tumors; or other measure of the level, stage, progression or severity of the cancer. In some embodiments, the amount is that effective for alleviating, reducing or eliminating an inflammatory condition.

The therapeutically effective amount can vary depending upon the intended application, or the subject and disease condition being treated, e.g., the desired biological endpoint, the pharmacokinetics of the compound, the disease being treated, the mode of administration, and the weight and age of the patient, which can readily be determined by one of ordinary skill in the art. The term also applies to a dose that will induce a particular response in target cells, e.g., reduction of cell migration. The specific dose will vary depending on, for example, the particular compounds chosen, the species of subject and their age/existing health conditions or risk for health conditions, the dosing regimen to be followed, the severity of the disease, whether it is administered in combination with other agents, timing of administration, the tissue to which it is administered, and the physical delivery system in which it is carried.

As used herein, the terms "treatment" or "treating" a disease or disorder refers to a method of reducing, delaying or ameliorating such a condition before or after it has occurred. Treatment may be directed at one or more effects or symptoms of a disease and/or the underlying pathology. Treatment is aimed to obtain beneficial or desired results including, but not limited to, therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient can still be afflicted with the underlying disorder. For prophylactic benefit, the pharmaceutical compounds and/or compositions can be administered to a patient at risk of developing a particular disease, or to a patient reporting one or more of the physiological symptoms of a disease, even though a diagnosis of this disease may not have been made. The treatment can be any reduction and can be, but is not limited to, the complete ablation of the disease or the symptoms of the disease. As compared with an equivalent untreated control, such reduction or degree of prevention is at least 5%, 10%, 20%, 40%, 50%, 60%, 80%, 90%, 95%, or 100% as measured by any standard technique.

As used herein, the term "therapeutic effect" refers to a therapeutic benefit and/or a prophylactic benefit as described herein. A prophylactic effect includes delaying or eliminating the appearance of a disease or condition, delaying or eliminating the onset of symptoms of a disease or condition, slowing, halting, or reversing the progression of a disease or condition, or any combination thereof.

As used herein, a "pharmaceutically acceptable form" of a disclosed compound includes, but is not limited to, pharmaceutically acceptable salts, hydrates, solvates, isomers, prodrugs, and isotopically labeled derivatives of disclosed compounds. In one embodiment, a "pharmaceutically acceptable form" includes, but is not limited to, pharmaceutically acceptable salts, isomers, prodrugs and isotopically labeled derivatives of disclosed compounds. In some embodiments, a "pharmaceutically acceptable form" includes, but is not limited to, pharmaceutically acceptable salts, stereoisomers, prodrugs and isotopically labeled derivatives of disclosed compounds.

As used herein, the term "pharmaceutically acceptable" excipient, carrier, or diluent refers to a pharmaceutically acceptable material, composition or vehicle, such as a liquid or solid filler, diluent, excipient, solvent or encapsulating material, involved in carrying or transporting the subject pharmaceutical agent from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations. Wetting agents, emulsifiers and lubricants, such as sodium lauryl sulfate, magnesium stearate, and polyethylene oxide-polypropylene oxide copolymer as well as coloring agents, release agents, coating agents, sweetening, flavoring and perfuming agents, preservatives and antioxidants can also be present in the compositions.

As used herein, the term "subject" refers to any animal (e.g., a mammal), including, but not limited to humans, non-human primates, rodents, and the like, which is to be the recipient of a particular treatment. Typically, the terms "subject" and "patient" are used interchangeably herein in reference to a human subject.

DETAILED DESCRIPTION OF THE INVENTION

The invention is based on the unexpected discovery that DKK3b, a cytoplasmic protein encoded by the Dkk3 gene locus, regulates the trafficking of β-TrCP substrates. The invention also relates to the discovery of intracellular inhibitor of β-catenin signaling, a vital new component of the Wnt pathway that regulates trafficking of β-catenin to the cell nucleus and novel therapeutic approaches to cancer treatment. The invention further relates to novel cancer therapeutics and methods of treatment based thereon. The invention also relates to biomarkers or companion diagnostics that indicate the activities of β-TrCP substrates.

Normal β-catenin signaling in the Dkk3 knockout mouse ($Dkk3^{tm1Cni}$) led us to re-examine the biological relevance of a ~30 kDa DKK3 isoform (D2p29) that shows dynamic, microfilament based intracellular trafficking in rat astrocytes. (Idel et al. 2006 *Mol Cell Biol* 26, 2317-2326; Leonard et al. 2000 *J Biol Chem* 275, 25194-25201; Stachelek et al. 2001 *J Biol Chem* 276, 35652-35659.) Amino acid sequence alignment revealed that secreted DKK3 and D2p29 (designated hereafter Dkk3b) differ at the N-terminus by the 71 amino acids that comprise the signal peptide sequence and N-glycosylation sites (FIG. 14a). Prior studies on other family members implied that furin-dependent proteolytic processing in the secretory vesicle was responsible for the multiple DKK3 species observed in the cell. (Niehrs 2006 *Oncogene* 25, 7469-7481.) However, direct analysis of furin-dependent proteolysis in astrocytes revealed that the ~30 kDa isoform was not a proteolytic by-product of a larger DKK3 protein (FIG. 14b).

As disclosed herein, the Dkk3 locus encodes a second vital intracellular protein that directly inhibits β-catenin nuclear translocation down-stream of the Wnt-regulated destruction complex.

The newly discovered Dkk3 gene product is an obligatory element in the Wnt/β-catenin signaling axis that adds a new dimension of regulation to one of the most studied signal transduction pathways in the cell. As a gatekeeper for β-catenin nuclear entry, IBS is an attractive target for the creation of new therapeutic modalities that impact Wnt/β-catenin signaling at a proximal node in the signaling cascade, and expands the therapeutic landscape for intervention in this key pathway in cancer.

DKK3 is the misunderstood member of an ancient family of secreted glycoproteins that regulate the Wnt/β-catenin pathway by interrupting the assembly of a functional Wnt liganded receptor. (Niehrs 2006 Oncogene 25, 7469-7481; Veeck et al. 2012 Biochim Biophys Acta 1825, 18-28.) It is the only family member that is an unambiguous tumor suppressor and a rich and diverse literature link DKK3, the β-catenin pathway, and tumor suppression. (Veeck et al. 2012 Biochim Biophys Acta 1825, 18-28.) However, the inability of DKK3 to block Wnt receptor assembly presents a conundrum in the understanding of the biology of this tumor suppressor. (Niehrs 2006 Oncogene 25, 7469-7481; Fujii et al. 2014 Acta Med Okayama 68, 63-78.) The discovery that the Dkk3 gene locus encodes a second gene product, IBS, a vital intracellular protein that directly regulates β-catenin trafficking resolves the longstanding confusion about the molecular function of this important component of the β-catenin signaling pathway. IBS provides a new level of regulation in the β-catenin signaling pathway that is independent of the Wnt ligand (FIG. 11) and is essential for embryogenesis. IBS is located downstream of the Wnt regulated degradation complex where it regulates β-catenin trafficking to the nucleus and has the capacity to protect β-catenin from proteolysis by redirecting it to the actin cytoskeleton. IBS rapidly shuttles between the perinuclear space and the cytoplasmic surface of the plasma membrane of astrocytes using myosin motors and actin fibers. (Stachelek et al. 2001 J Biol Chem 276, 35652-35659; Stachelek et al. 2000 J Biol Chem 275, 31701-31707.) This intracellular cycling of IBS may provide a functional shuttling service capable of relocating β-catenin from the vicinity of the nucleus back to its plasma membrane reservoir, closing a previously unrecognized arm of the regulatory loop. This novel and essential component of the Wnt/β-catenin pathway directly antagonizes the pro-proliferative β-catenin signaling molecule providing an important new point of control that impacts the regulatory pathways responsible for differentiation, lineage specification, pluripotency and oncogenesis.

As disclosed herein, DKK3b acts more broadly to regulate other β-TrCP target substrates in addition to β-catenin, including NF-κB, p38, and Erk1/2 (FIG. 23 and FIG. 24). This adds a new dimension of regulation to one of the most studied ubiquitin-proteasome systems (UPS) in the cell. The present invention provides a novel therapeutic intervention for arresting cellular processes that are intimately related to tumorigenesis, including proliferation, differentiation, inflammation and apoptosis pathways. As a modulator of β-TrCP substrate degradation and nuclear entry, DKK3b is an attractive target for the creation of new drugs for intervention in key cancer.

DKK3b fused to an N-terminal cell penetrating peptide, a protein construct we refer to as TAT-IBS (a.k.a. cpIBS), regulates the activity of promoter elements that depend upon the nuclear translocation of β-TrCP target substrates (FIG. 23) as determined by promoter-luciferase reporter assays. Wnt-1 stimulates transcription regulated by NF-κB (FIG. 23A), β-catenin, and E2F (FIG. 23 C) transcription factor proteins. TAT-IBS treatment blocks this Wnt-1-induced stimulation. In contrast, Wnt-1 down-regulates transcription from promoter elements of two biomarkers of epithelial cellular differentiation, E-cadherin (FIG. 23C) and Elf3 (FIG. 23B). TAT-IBS treatment blocks Wnt-1-induced repression of these two epithelial gene transcripts.

TAT-IBS inhibits the nuclear translocation of βTrCP target substrates, at least in part, by mediating sequestration at cytoplasmic microfilaments. We showed previously (UMMC 12-40PR2) that IBS blocks the nuclear import and increases microfilament bound β-catenin while stabilizing the total cell content. Disclosed herein is that NF-κB, p38, and Erk1/2 proteins are also bound to cytoplasmic microfilaments in an IBS-dependent complex (FIG. 2). This sequestration prevents the nuclear translocation of these of β-TrCP target substrates, and thus defines the molecular basis for the silencing of β-TrCP target substrate signaling by IBS.

TrCP inhibitors are likely to prove more efficacious while reducing toxicities compared to proteasome inhibitors like bortezomib (Velcade). (Frescas, et al. 2008 Nature Reviews Cancer 8, 438-449.) The proteasome inhibitor bortezomib is clinically effective for the treatment of multiple myeloma; however, toxic side effects limit bortezomib's widespread use for other cancer indications. Since drugs like bortezomib stabilize large, nonspecific pools of proteins degraded by the proteasome, there is an urgent need to identify inhibitors of specific proteins by particular ubiquitin ligases such as βTrCP to arrest the growth of various cancers.

The disclosed invention provides a unique therapeutic approach based on DKK3b regulation of β-TrCP E3 ubiquitin ligase, giving rise to novel therapeutics and treatment methods based thereon for treating tumors and inflammatory diseases and conditions. The activities of a variety of β-TrCP substrates can also be used as biomarkers or companion diagnostics for Dkk3b/IBS treatments. E.g. blood cells could be collected from patients pre- and post-IBS treatment. TNFa or phorbol ester (PBA), or lipopolysaccharide (LPS) could be used to stimulate NF-κB activity in the collected blood cells. The pre versus post-treatment ratio NF-κB dependent cell activity would indicate DKK3b/IBS activity.

Also disclosed herein are variants of both the cpIBS and a secreted-cpIBS that are (1) secreted as functional tumor suppressors or expressed as cell penetrating linear polypeptides; and/or (2) carry the minimal required domains for activity.

It was discovered that the DKK3 locus produces two proteins from two different transcripts originating from separate transcriptional start sites: DKK3-a secreted glycoprotein of unknown function, and IBS—the intracellular effector protein that regulates β-catenin driven cell proliferation. IBS is the functional gene product that silences β-catenin signaling by capturing β-catenin in an inhibitory complex composed of β-TRCP, IBS and β-catenin. This complex prevents nuclear translocation of the signaling molecule. Importantly, expression of the secreted DKK3 has no direct biological impact on cancer cell proliferation or β-catenin signaling. An IBS variant was generated for therapeutic delivery of this anti-cancer protein by fusing a cell-penetrating domain to the N-terminus of IBS and synthesizing the fusion protein in bacteria. Purification of the unfolded protein produces a linear polypeptide chain that when added to cells ex vivo or injected into tumor bearing mice in vivo, promptly and selectively arrests cancer cell proliferation and rapidly initiates tumor cell apoptosis (PCT/US2013/031118).

Delivery of this intracellular tumor suppressor to the cytoplasm of the cancer cell is essential to achieve the cancer cell growth arrest and apoptosis. First attempts were made by fusing a variant of the cell penetrating peptide-TAT. (Schwarze et al 1999 Science 285(5433):1569-72.) Delivery of the bacterially expressed, unfolded TAT-IBS (cpIBS) fusion protein arrested growth of human ovarian, pancreatic, and colon cancers in tumor bearing PDX-mice and led to tumor necrosis. Importantly, cpIBS had no effects on any biology in the mouse when given in excess for 35 days.

To optimize the IBS tumor suppressor for therapeutic use, functional domain analysis was done by domain deletion from the N- and C-termini of the full length IBS. This identified the N-terminal 122 amino acids and the last 10 residues at the C-terminus as essential for tumor suppressor function. Fusion of IBS122 to the last 10 residues of the C-terminus produced a fully functional tumor suppressor. Further analysis revealed that residues between aa12 to aa70 are also not required for tumor suppressor activity.

Also studied were other avenues for production of a membrane permeate IBS based on the recent identification of a secreted PTEN phosphatase capable of entering cells and regulating PTEN signaling. (Hopkins et al 2013 Science 341: 399-402). The N-terminal 62 residues of the secreted PTEN protein composed of the signal peptide sequence (recognized by the Signal Recognition Particle for ER translocation) and a cell penetrating poly-Arginine domain was fused to the N-terminus of IBS and expression of the secreted PTEN-cp-IBS fusion protein was done in CHO cells. Spent media from CHO cells harboring the PTEN-cp-IBS secreted from 100-200 pg/mL of the fusion IBS that full silenced β-catenin signaling in a standard TOPFLASH assay.

The use of adenovirus delivered DKK3 to treat prostate cancer relies on the ability of this secreted, over-expressed, exogenous protein to initiate an ER stress/UPR (unfolded protein response) response resulting in apoptosis of the virally infected cancer cells (U.S. Pat. No. 8,658,611 B2). The N-terminal 74 residues of the secreted DKK3 also elicit an identical ER stress/UPR response when over-expressed in cancer cells and this variant lacks any of the distinguishing features of the DKK3 family (U.S. Pat. No. 8,618,273 B2). ER stress/UPR response is one of the most common artifacts of over-expression of secreted proteins. The ability of a secretory signal derived from DKK3—but lacking any family characteristics—to phenocopy the full length secreted DKK3 renders indicates that none of the DKK3 domains are required for this indication. This is materially different from the biology of IBS silencing of β-catenin signaling. IBS silences dysregulated β-catenin signaling in cancer cells resulting in growth arrest and JNK mediated apoptosis. The molecular mechanism responsible for this biology is known; IBS directly prevents the nuclear translocation of the β-catenin signaling molecule. This is a qualifying significant improvement over the current art (U.S. Pat. Nos. 8,658,611 B2 and 8,618,273 B2). The described new IBS variants improve the unique qualities of IBS action by isolating two biologically essential domains required for silencing of β-catenin signaling, and provide a means to deliver the IBS therapeutic throughout the body.

The invention provides related families of either secreted, cell penetrating-IBS fusions (ScpIBS) or unfolded, linear, cell penetrating-IBS proteins (cpIBS). The two families differ by the N-terminal fusion component. The general organization of these secreted, folded proteins is shown in FIG. 1.

Initial fusion constructs were composed of the N-terminal 62 residues from the secreted human PTEN gene encoding the following secretion signal peptide and cell penetrating domain:

```
SRP/Cleaved in ER                                    cp
                                              (SEQ ID NO: 1)
NH2-MLERGGEAAAAAAAAAAAPGRGSESPVTISRAGNAGELVSPLLLPP

TRRRRRRHIQGPGPV
 1      10      20      30      40      50      60
```

Spacing between the SRP sequence and the cp domain was unaltered in this first pass.

Two PTEN_cp_IBS tumor suppressor constructs were synthesized in CHO cells.

Variant 1 consists of the full length 281 residue long polypeptide fused to the PTEN_cp domain and variant 2 is an IBS truncation mutant composed of residues 1-122 fused to the following C-terminal sequence required for function —AAALLGGEEIstop (SEQ ID NO: 2).

| Variant # | |
| --- | --- |
| 1 | PTEN_cp_IBS |
| 2 | PTEN_cp_IBS$^{122}$ |

The CHO cells were transfected with an expression plasmids harboring the (1) PTEN-cp_IBS (PcpIBS) and (2) PTEN-cp_IBS122 (PcpIBS122); two non secreted controls, (3) mCherry-T2A-IBS mC-IBS and 4) mCherry-T2A-IBS122; and two secreted by inactive C-terminus deletion mutants 5) PTEN-cp_IBSdeltaC-term and PTEN-cp_IBS122delta C-term. Constructs 1&2 secrete the presumed functional IBS molecules; constructs 3&4 produce intracellular functional IBS, but do not secrete the protein; and constructs 5&6 secrete IBS protein lacking the C-terminal 10 residues—these are required for function.

Stable transfections of the individual constructs in CHO cells were prepared by G418 selection and spent media from a 2 day growth period in the absence of G418 was collected.

Spent CHO media was added to the HEK293T reporter cell line harboring the (3-catenin signaling reporter TOPFLASH (Tcf-fLuc) and a control (Eflalpha-RLuc), and the cells stimulated with 15 mM LiCl for 16 h. A dual luciferase assay from Promega was used to evaluate the impact of IBS on β-catenin signaling. A commercial ELISA assay for DKK3 that recognizes epitopes between aa200-aa250 in the full length IBS revealed that 100-150 pg/ml PTEN-cp_IBS present in the spent CHO media. (FIG. 2)

Optimal distance between the (1) SRP, (2) the cp and IBS are determined using secretion yield determined by ELISA of spent media for CHO cells harboring the fusion construct(s) and TOPFLASH assays as the endpoints.

Further work shows that the first 10 residues of IBS are also required for function. Residues 11-60 are predicted to have a random coil:α-helix; β-pleated sheet configuration suggesting that they may be eliminated/replaced or shortened without altering the bioactivity of the mutant IBS. The family of N-domain mutants to be used is listed in FIG. 3.

Alternative SRP and cp domains can be used in place of the native PTEN elements. The SRP domain is common in all secretory proteins. Similarly, the poly arginine cp domain in PTEN can be exchanged for optimized synthetic cp elements as used in the cpIBS variants (see below).

The general organization of these secreted, folded proteins is shown in FIG. 4.

The cp_IBS tumor suppressor construct Variant 8 consists of the full length 281 residue long polypeptide fused to the a 55 residue long synthetic cp domain composed of a $^6$His epitope tag YARAAARQARAG- and variant 2 ("$^6$His" disclosed as SEQ ID NO: 3 and "YARAAARQARAG" disclosed as SEQ ID NO: 4) is an IBS truncation mutant composed of residues 1-122 fused to the following C-terminal sequence required for function—AAALLGGEEIstop (SEQ ID NO: 2). (FIG. 5)

In one aspect, the invention generally relates to an isolated recombinant human inhibitor of β-catenin signaling protein, or a variant thereof.

In another aspect, the invention generally relates to a fusion protein comprising inhibitor of β-catenin signaling protein, or a variant thereof.

In yet another aspect, the invention generally relates to a host cell transformed with an isolated recombinant human inhibitor of β-catenin signaling protein, or a variant or fusion protein thereof.

In yet another aspect, the invention generally relates to an isolated nucleic acid molecule comprising a polynucleotide sequence that encodes inhibitor of β-catenin signaling protein, or a variant thereof.

In yet another aspect, the invention generally relates to a recombinant virus genetically modified to express human inhibitor of β-catenin signaling protein, or a variant thereof.

In yet another aspect, the invention generally relates to a recombinant transgene comprising a polynucleotide that encodes human inhibitor of β-catenin signaling protein, or a variant thereof.

In yet another aspect, the invention generally relates to a pharmaceutical composition comprising a messenger RNA (mRNA) encoding the human inhibitor of β-catenin signaling protein, or a variant thereof, and a pharmaceutically acceptable carrier.

In yet another aspect, the invention generally relates to a pharmaceutical composition comprising a recombinant virus genetically modified to express human inhibitor of β-catenin signaling protein, or a variant thereof, and a pharmaceutically acceptable carrier.

In yet another aspect, the invention generally relates to a method for treating cancer or inhibiting tumor progression in a subject in need thereof, comprising administering to the subject a pharmaceutical composition comprising a recombinant virus genetically modified to express human inhibitor of β-catenin signaling protein, or a variant thereof, and a pharmaceutically acceptable carrier.

In yet another aspect, the invention generally relates to a pharmaceutical composition comprising human inhibitor of β-catenin signaling protein, or a variant or fusion protein thereof, and a pharmaceutically acceptable carrier.

In yet another aspect, the invention generally relates to a method for treating cancer or inhibiting tumor progression in a subject in need thereof, comprising administering to the subject a pharmaceutical composition comprising inhibitor of β-catenin signaling protein, or a variant or fusion protein thereof.

Cancers that may be treated by the method disclosed herein can be selected from the group consisting of carcinoma, lymphoma, blastoma, sarcoma, liposarcoma, neuroendocrine tumor, mesothelioma, schwanoma, meningioma, adenocarcinoma, melanoma, leukemia, lymphoid malignancy, squamous cell cancer, epithelial squamous cell cancer, lung cancer, small-cell lung cancer, non-small cell lung cancer, adenocarcinoma of the lung, squamous carcinoma of the lung, cancer of the peritoneum, hepatocellular cancer, gastric or stomach cancer, gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, testicular cancer, esophageal cancer, a tumor of the biliary tract, and head and neck cancer.

In certain preferred embodiments, the cancer or tumor being treated is that of ovary.

In certain preferred embodiments, the cancer or tumor being treated is that of pancreas.

In certain preferred embodiments, the method disclosed herein for treating cancer further includes administering to the subject a pharmaceutical composition comprising a second active anti-tumor agent.

The second active anti-tumor agent may be a small molecule, a chemotherapeutic agent, a peptide, a polypeptide or protein, an antibody, an antibody-drug conjugate, an aptamer or nucleic acid molecule.

In certain embodiments, the second active anti-tumor agent is a chimeric antigen receptor (CAR)-modified T cells-based therapy, T cells genetically modified to stably express a desired CAR. (See, e.g., WO2012079000 A1, US 20150283178 A1.)

In certain embodiments, the nucleic acid molecule is selected from single-stranded or double-stranded RNA or DNA, and derivatives or analogs thereof. In certain embodiments, the nucleic acid molecule is selected from dsRNA, siRNA, mRNA, ncRNA, microRNA, catalytic RNA, gRNA, aptamers, genes, plasmids, and derivatives or anologs thereof.

In certain embodiments, the second active anti-tumor agent is a messenger RNA (mRNA)-based therapy, e.g., mRNA made of nucleotide or its analogs to trigger the body's natural processes to produce proteins in the human cell. (See, e.g., US 20140147432A1, US 20140107189A1)

The term "chemotherapeutic agent" is a chemical compound useful in the treatment of cancer. Examples of chemotherapeutic agents include Erlotinib (TARCEVA®, Genentech/OSI Pharm.), Bortezomib (VELCADEER, Millennium Pharm.), Fulvestrant (FASLODEX®), AstraZeneca), Sutent (SU11248, Pfizer), Letrozole (FEMARA®, Novartis), Imatinib mesylate (GLEEVEC®, Novartis), PTK787/ZK 222584 (Novartis), Oxaliplatin (Eloxatin®, Sandi), 5-FU (5-fluorouracil), Leucovorin, Raparnycin (Sirolimus, RAPAMUNE®, Wyeth), Lapatinib (TYKERB®, GSK572016, Glaxo Smith Kline), Lonafarnib (SCH 66336), Sorafenib (BAY43-9006, Bayer Labs), and Gefitinib (IRESSA®, AstraZeneca), AG1478, AG1571 (SU 5271; Sugen), alkylating agents such as thiotepa and CYTOXAN® cyclophosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including the synthetic analog topotecan); bryostatin; callystatin; CC-1065 (including its adozelesin, carzelesin and bizelesin synthetic analogs); cryptophycins (particularly cryptophycin 1 and cryptophycin 8); dolastatin; duocarmycin (including the synthetic analogs, KW-2189 and CB1-TM1); eleutherobin; pancratistatin; a sarcodictyin; spongistatin; nitrogen mustards such as chlorambucil, chlomaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheatnicin, especially calicheamicin gammaII and calicheamicin omegaII. (Angew Chem. Intl. Ed. Engl. (1994) 33: 183-186); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® (doxorubicin), morpholino-doxorubicin, cyanomorpholino-doxorubicin, 2-pyrrolino-doxorubicin and deoxydoxorubicin), epirubicin, esonibicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6mercaptopurine, thiamniprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophospharnide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® (paclitaxel; Bristol-Myers Squibb Oncology, Princeton, N.J.), ABRAXANE® (Cremophor-free), albumin-engineered nanoparticle formulations of paclitaxel (American Pharmaceutical Partners, Schaumberg, 111.), and TAXOTERE® (doxetaxel; Rhone-Poulenc Rorer, Antony, France); chloranmbucil; GEMZAR® (gemcitabine); 6-thioguanine; mercaptopurine; methotrexate; platinum analogs such as cisplatin and carboplatin; vinblastine; etoposide (VP-16); ifosfamide; mitoxantrone; vincristine; NAVELBINE® (vinorelbine); novantrone; teniposide; edatrexate; daunomycin; aminopterin; capecitabine (XELODA®); ibandronate; CPT-11; topoisomerase inhibitor RFS 2000; difluoromethylomithine (DMFO); retinoids such as retinoic acid; and pharmaceutically acceptable salts, acids and derivatives of any of the above.

In certain embodiments, the second anti-tumor agent is an antibody, a single chain antibody, an antibody fragment that specifically binds to the target cell, a monoclonal antibody, a single chain monoclonal antibody, a monoclonal antibody fragment that specifically binds to a target cell, a chimeric antibody, a chimeric antibody fragment that specifically binds to the target cell, a domain antibody, a domain antibody fragment that specifically binds to the target cell, a lymphokine, a hormone, a vitamin, a growth factor, a colony stimulating factor, or a nutrient-transport molecule. Alternatively, the cell-binding agent is a monoclonal antibody, a single chain monoclonal antibody, or a monoclonal antibody fragment that specifically binds to a target cell.

In yet another aspect, the invention generally relates to a method for inducing a tumor-suppression effect in a subject in need thereof, comprising administering to the subject a pharmaceutical composition comprising inhibitor of β-catenin signaling protein, or a variant or fusion protein thereof.

In yet another aspect, the invention generally relates to a method for establishing susceptibility of a cancer patient to tumor-suppression treatment by inhibitor of β-catenin signaling protein, or a variant or fusion protein thereof.

In certain preferred embodiments, the cancer being evaluated for tumor-suppression treatment by inhibitor of β-catenin signaling or a fusion protein thereof is selected from the group consisting of carcinoma, lymphoma, blastoma, sarcoma, liposarcoma, neuroendocrine tumor, mesothelioma, schwanoma, meningioma, adenocarcinoma, melanoma, leukemia, lymphoid malignancy, squamous cell cancer, epithelial squamous cell cancer, lung cancer, small-cell lung cancer, non-small cell lung cancer, adenocarcinoma of the lung, squamous carcinoma of the lung, cancer of the peritoneum, hepatocellular cancer, gastric or stomach cancer, gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, testicular cancer, esophageal cancer, a tumor of the biliary tract, and head and neck cancer.

In yet another aspect, the invention generally relates to a method for treating cancer or inhibiting tumor progression in a subject in need thereof, comprising administering to the subject a pharmaceutical composition comprising a recombinant virus genetically modified to express human DKK3b protein and a pharmaceutically acceptable carrier. Exemplary cancer or tumor that may be treated include: carcinoma, lymphoma, blastoma, sarcoma, liposarcoma, neuroendocrine tumor, mesothelioma, schwanoma, meningioma, adenocarcinoma, melanoma, leukemia, lymphoid malignancy, squamous cell cancer, epithelial squamous cell cancer, lung cancer, small-cell lung cancer, non-small cell lung cancer, adenocarcinoma of the lung, squamous carcinoma of the lung, cancer of the peritoneum, hepatocellular cancer, gastric or stomach cancer, gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, testicular cancer, esophageal cancer, a tumor of the biliary tract, and head and neck cancer.

In yet another aspect, the invention generally relates to a method for treating an inflammatory disease or condition in a subject in need thereof, comprising administering to the subject a pharmaceutical composition comprising a recombinant virus genetically modified to express human DKK3b protein and a pharmaceutically acceptable carrier.

In yet another aspect, the invention generally relates to a pharmaceutical composition suitable for use in for treating cancer or inhibiting tumor progression, comprising human DKK3b protein and a pharmaceutically acceptable carrier.

In yet another aspect, the invention generally relates to a pharmaceutical composition suitable for use in for treating inflammatory disease or condition, comprising human DKK3b protein and a pharmaceutically acceptable carrier.

Inflammatory diseases or conditions that may be treated with the compositions and methods disclosed herein include any disease or condition characterized by an inflammatory or allergic process as is known in the art, such as inflammation, acute inflammation, chronic inflammation, respiratory disease, atherosclerosis, psoriasis, dermatitis, restenosis, asthma, allergic rhinitis, atopic dermatitis, septic shock, rheumatoid arthritis, inflammatory bowel disease, inflammatory pelvic disease, pain, ocular inflammatory disease, celiac disease, Leigh syndrome, glycerol kinase deficiency, familial eosinophilia, autosomal recessive spastic ataxia, laryngeal inflammatory disease; tuberculosis, chronic cholecystitis, bronchiectasis, silicosis and other pneumoconioses.

Listing of diseases and conditions that may be impacted by the methods or compositions disclosed herein are also provided in the Table 3.

TABLE 3

| | |
|---|---|
| Ageing | Chung et al, 2002; Adler et al, 2007; Csizar et al, 2008 |
| Allergies | Cousins et al, 2008 |
| Headaches | Reuter et al, 2003 |
| Pain | Tegeder et al, 2004; Niederberger & Geisslinger, 2008 |
| Complex Regional Pain Syndrome | Hettne et al, 2007 |
| Cardiac Hypertrophy | Purcell & Molkentin, 2003; Freund et al, 2005; Sen & Roy, 2005 |
| Muscular Dystrophy (type 2A) | Baghdiguian et al, 1999 |
| Muscle wasting | Hasselgren, 2007 |
| Catabolic disorders | Holmes-McNary, 2002 |
| Diabetes mellitus, Type 1 | Ho & Bray, 1999; Eldor et al, 2006 |
| Diabetes mellitus, Type 2 | Yuan et al, 2001; Lehrke et al, 2004; Chen, 2005 |
| Obesity | Gil et al, 2007 |
| Fetal Growth Retardation | Mammon et al, 2005 |
| Hypercholesterolemia | Wilson et al, 2000 |
| Atherosclerosis | Ross et al, 2001; Li & Gao, 2005 |
| Heart Disease | Valen et al, 2001 |
| Chronic Heart Failure | Frantz et al, 2003; Gong et al, 2007 |
| Ischemia/reperfusion | Toledo-Pereyra et al, 2004; Nichols, 2004; Ridder & Schwaninger, 2008 |
| Stroke | Herrmann et al, 2005 |
| Cerebral aneurysm | Aoki et al, 2007; 2009 |
| Angina Pectoris | Ritchie, 1998 |
| Pulmonary Disease | Christman et al, 2000 |
| Cystic Fibrosis | Pollard et al, 2005; Carrabino et al, 2006; Rottner et al, 2007 |
| Acid-induced Lung Injury | Madjdpour et al, 2003 |
| Pulmonary hypertension | Sawada et al, 2007 |
| Chronic Obstr. Pulmonary Disease (COPD) | Barnes, 2002; Rahman & Kilty, 2006 |
| Hyaline Membrane Disease | Cheah et al, 2005 |
| Kidney Disease | Guijarro & Egido, 2001; Camici, 2006; Guzik & Harrison, 2007 |
| Glomerular Disease | Zheng et al, 2005 |
| Alcoholic Liver Disease | Zima & Kalousova, 2005 |
| Leptospirosis renal disease | Yang et al, 2001 |
| Gut Diseases | Neurath et al, 1998 |
| Peritoneal endometriosis | Gonzalez-Ramos et al, 2007 |
| Skin Diseaes | Bell et al, 2003 |
| Nasal sinusitis | Xu et al, 2006 |
| Anhidrotic Ecodermal Dysplasia-ID | Puel et al, 2005 |
| Behcet's Disease | Todaro et al, 2005 |
| Incontinentia pigmenti | Courtois & Israel, 2000 |
| Tuberculosis | Zea et al, 2006 |
| Asthma | Pahl & Szelenyi, 2002 |
| Arthritis | Roshak et al, 2002; Roman-Blas & Jimenez, 2006; Aud & Peng, 2006; Okamoto, 2006 |
| Crohn's Disease | Pena & Penate, 2002 |
| Colitis (rat) | Chen et al, 2005 |
| Ocular Allergy | Bielory et al, 2002 |
| Glaucoma | Zhou et al, 2005 |
| Appendicitis | Pennington et al, 2000 |
| Paget's Disease | Lin et al, 2007 |
| Pancreatitis | Weber & Adler, 2001; Gray et al, 2006 |
| Periodonitis | Nichols et al, 2001; Ambili et al, 2005 |
| Endometriosis | Guo, 2006; Celik et al, 2008 |
| Inflammatory Bowel Disease | Dijkstra et al, 2002; Atreya et al, 2008 |
| Inflammatory Lung Disease | Park & Christman, 2006 |
| Sepsis | Wratten et al, 2001; Abraham, 2003 |
| Silica-induced | Chen & Shi, 2002 |
| Sleep apnoea | Lavie, 2003 |
| AIDS (HIV-1) | Hiscott et al., 2001 |

TABLE 3-continued

| | |
|---|---|
| Autoimmunity | Hayashi & Faustman, 2000; Bacher & Schmitz, 2004 |
| Antiphospholipid Syndrome | Lopez-Pedrera et al, 2005 |
| Lupus | Kammer & Tsokos, 2002; Okamoto, 2006; Oikonomidou et al, 2007 |
| Lupus nephritis | Zheng et al, 2006, 2008 |
| Chronic Disease Syndrome | Maes et al, 2007 |
| Familial Mediterranean Fever | Onen, 2005 |
| Hereditary Periodic Fever Syndrome | Jeru et al, 2008 |
| Psychosocial stress diseases | Bierhaus et al, 2004 |
| Neuropathological Diseases | Cechetto, 2001; Mattson & Camandola, 2001; Pizzi & Spano, 2006 |
| Familial amyloidotic polyneuropathy, inflamm neuropathy | Mazzeo et al, 2004 |
| Traumatic brain injury | Hang et al, 2005 |
| Spinal cord injury | Brambilla et al, 2005 |
| Parkinson Disease | Soos et al, 2004, Mogi et al, 2006 |
| Multiple Sclerosis | Satoh et al, 2007 |
| Rheumatic Disease | Okamoto, 2006; Greetham et al, 2007 |
| Alzheimers Disease | Mattson & Camandola, 2001; Collister & Albensi, 2005 |
| Amyotropic lateral sclerosis | Xu et al, 2006 |
| Huntington's Disease | Khoshnan et al, 2004 |
| Retinal Disease | Kitaoka et al, 2004 |
| Cataracts | Yang et al, 2006 |
| Hearing loss | Merchant et al, 2005; Lang et al, 2006 |
| Cancer | Gilmore et al, 2002; Karin et al, 2002: Lee et al, 2007 |

(See, www.bu.edu/nf-kb/physiological-mediators/diseases/)

Any appropriate route of administration can be employed, for example, parenteral, intravenous, subcutaneous, intramuscular, intraventricular, intracorporeal, intraperitoneal, rectal, or oral administration. Most suitable means of administration for a particular patient will depend on the nature and severity of the disease or condition being treated or the nature of the therapy being used and on the nature of the active compound.

Solid dosage forms for oral administration include capsules, tablets, pills, powders, and granules. In such solid dosage forms, the compounds described herein or derivatives thereof are admixed with at least one inert customary excipient (or carrier) such as sodium citrate or dicalcium phosphate or (i) fillers or extenders, as for example, starches, lactose, sucrose, glucose, mannitol, and silicic acid, (ii) binders, as for example, carboxymethylcellulose, alignates, gelatin, polyvinylpyrrolidone, sucrose, and acacia, (iii) humectants, as for example, glycerol, (iv) disintegrating agents, as for example, agar-agar, calcium carbonate, potato or tapioca starch, alginic acid, certain complex silicates, and sodium carbonate, (v) solution retarders, as for example, paraffin, (vi) absorption accelerators, as for example, quaternary ammonium compounds, (vii) wetting agents, as for example, cetyl alcohol, and glycerol monostearate, (viii) adsorbents, as for example, kaolin and bentonite, and (ix) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents. Solid compositions of a similar type may also be employed as fillers in soft and hard-filled gelatin capsules using such excipients as lactose or milk sugar as well as high molecular weight polyethyleneglycols, and the like. Solid dosage forms such as tablets, dragees, capsules, pills, and granules can be prepared with coatings and shells, such as enteric coatings and others known in the art.

Liquid dosage forms for oral administration include pharmaceutically acceptable emulsions, solutions, suspensions, syrups, and elixirs. In addition to the active compounds, the liquid dosage forms may contain inert diluents commonly used in the art, such as water or other solvents, solubilizing agents, and emulsifiers, such as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil, sesame oil, glycerol, tetrahydrofurfuryl alcohol, polyethyleneglycols, and fatty acid esters of sorbitan, or mixtures of these substances, and the like. Besides such inert diluents, the composition can also include additional agents, such as wetting, emulsifying, suspending, sweetening, flavoring, or perfuming agents.

Materials, compositions, and components disclosed herein can be used for, can be used in conjunction with, can be used in preparation for, or are products of the disclosed methods and compositions. It is understood that when combinations, subsets, interactions, groups, etc. of these materials are disclosed that while specific reference of each various individual and collective combinations and permutations of these compounds may not be explicitly disclosed, each is specifically contemplated and described herein. For example, if a method is disclosed and discussed and a number of modifications that can be made to a number of molecules including in the method are discussed, each and every combination and permutation of the method, and the modifications that are possible are specifically contemplated unless specifically indicated to the contrary. Likewise, any subset or combination of these is also specifically contemplated and disclosed. This concept applies to all aspects of this disclosure including, but not limited to, steps in methods using the disclosed compositions. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed.

EXAMPLES

The Dkk3$^{tm1Cni}$ mutant mouse was generated by disrupting exon 2 of the Dkk3 gene that harbors a biologically important CpG island and encodes the N-terminal 71 amino acids that comprise the signal peptide sequence and N-glycosylation sites of secreted DKK3 (FIG. 6a). (Kobayashi et al. 2002 Gene 282, 151-158; Lodygin et al. 2005 *Cancer Res* 65, 4218-4227; Sato et al. 2007 *Carcinogenesis* 28, 2459-2466.) Control wild type brain membranes had both DKK3 isoforms, glycosylated DKK3 was ~75% and DKK3b was ~25% of the total DKK3 present (FIG. 6b, FIG. 14b).

Brain membranes from the DKK3$^{tm1Cni}$ mouse showed the expected loss of the glycosylated DKK3 due to the targeted mutation of exon 2. However, DKK3b was not only present but increased ~2-fold (FIG. 6b), confirming that the smaller 30 kDa isoform was not a proteolytic fragment of the larger DKK3 and raised the possibility that epigenetic modification of the CpG island in exon 2 may impact DKK3b expression.

Transcript analysis confirmed that DKK3b is encoded by mRNA distinct from the longer DKK3 gene product and is driven by a promoter located within intron 2 of the Dkk3 gene. The initiator methionine of DKK3b is the first codon in exon 3 of the vertebrate Dkk3 gene from frogs to man and is separated from exon 2 by up to a 6 kb intron (FIG. 6a). Exon specific qPCR of rat astrocyte Dkk3 mRNA showed that all transcripts contained exon 3 codons but only ~60% of these transcripts had the exon 2 codon (FIG. 15). Total RNA from the Dkk3$^{tm1Cni}$ mouse brain showed readily detectible Dkk3 transcripts with exon 3 codons but lacked any Dkk3 transcripts with exon 2 codons (FIG. 6c).

The DkkP3$^{tm1Cni}$ mutant mouse retained all of intron 2 of the Dkk3 gene and potential transcriptional regulatory elements capable of initiating transcription from exon 3 were identified by luciferase reporter assays. Robust promoter activity was found in intron 2 and progressive deletion studies positioned a functional promoter (TSS2) in the 250 nucleotides adjacent to exon 3 (FIG. 6d). A TATA box required for promoter activity was located at −35 nucleotides 5' from exon 3 in the rat Dkk3 gene (FIG. 6d). In the mouse and human Dkk3 genes, a putative TATA box element is located at −90 nucleotides from the exon 3. Chromatin immunoprecipitation (ChIP) of rat astrocyte DNA showed that the TSS2 in the Dkk3 gene bound RNA Pol II (FIG. 6e) and TBP indicating the formation of a second transcriptional pre-initiation complex at TSS2 in astrocytes. This TSS2 initiates transcription of an mRNA where exon 3 is its first coding exon and the resulting transcript encodes a ~30 kDa intracellular protein (DKK3b) lacking domains required for ER internalization, glycosylation and secretion.

Dkk3b is Responsible for the Dkk3 Gene Functions In Vivo

The biological significance of DKK3b was evaluated in the mouse by targeted gene editing using artificial nucleases and homologous recombination. Zinc finger nucleases (ZFNs, FIG. 16a,b) were utilized to insert a floxed cyan fluorescent protein (CFP) reporter between TSS2 and exon 3 of the Dkk3 gene (HR, FIG. 17). (Gupta et al. 2012 Nature Methods 9, 588-590.) This disruption of intron 2 preserves TSS1-driven DKK3 expression but terminates TSS2-driven transcription following the CFP reporter, which should result in the selective functional deletion of DKK3b in homozygous animals. Prior to their application in mouse embryos, the efficiency of ZFN-mediated donor DNA insertion was validated in immortal C8D1A cells isolated from the C57Bl/6j mouse using Cel-I assays and single stranded oligonucleotide directed homology repair (data not shown). ZFN-mediated insertion of the CFP HR cassette resulted in weak expression of CFP in the immortalized C8D1A cell line, where Dkk3 expression is silenced by hyper-methylation of CpG island(s) at Dkk3 locus (FIG. 7a). (Kobayashi et al. 2002 Gene 282, 151-158; Tsuji et al. 2000 *Biochem Biophys Res Commun* 268, 20-24; Xiang et al. 2013 *Journal of Cellular and Molecular Medicine* 17, 1236-1246.) CFP expression increased >5 fold when DNA methyltransferase activity was inhibited in the gene edited C8D1A$^{cfp/+}$ reporter cell demonstrating that TSS2-driven CFP substitutes for Dkk3b expression (FIG. 7a).

ZFN$^{Dkk3b}$ mRNAs and a linear HR donor DNA were injected into C57B16 mouse zygotes to create the Dkk3b knock-in mouse. Thirty-five of 65 (54%) injected one cell embryos produced viable pups and DNA sequencing of the ~3.2 kb Dkk3 gene bracketing the HR repaired target locus confirmed that 3 founders (8.6%) had the floxed CFP reporter inserted 35 nucleotides upstream from exon 3 of the Dkk3 gene with preserved native splice junctions (FIG. 17b,c). F1 progeny from crosses of a wild type male to a Dkk3$^{CFP/+}$ female (founder #19) showed Mendelian inheritance patterns characteristic of a single segregating allele (FIG. 7b). No off-target mutations were found in founder #19 for the 10 highest predicted candidate target sites (FIG. 14, Table 2). (Fine et al. 2014 *Nucleic Acids Research* 42, e42.) The TSS2-driven CFP was expressed throughout the Dkk3$^{CFP/+}$ mouse (FIG. 7c) illustrating the ubiquitous nature of TSS2 activity of the Dkk3 gene.

DKK3b is essential for embryo survival as no viable homozygous Dkk3$^{CFP/CFP}$ offspring were produced. No homozygous Dkk3$^{CFP/CFP}$ embryos were found as early as embryonic day 4.5 (n=17 embryos) indicating that DKK3b expression is essential for survival before or near the time of embryo implantation. This outcome differs markedly from that of the Dkk3$^{tm1Cni}$ mouse and shows that at least one wild type Dkk3 allele that generates Dkk3b transcripts is required for survival (FIG. 7b). The penetrance of the lethal phenotype for the single segregating Dkk3$^{CFP}$ allele was confirmed in out-crosses on the CD1 background (FIG. 7b). The lethal phenotype of the Dkk3$^{CFP}$ mutation was rescued by a Sox2 promoter-driven Cre recombinase that excises the floxed CFP cassette in the unfertilized oocyte leaving a single 34 bp loxP recognition site remnant at the Dkk3 locus (FIG. 18). (Hayashi et al. 2002 Gene Expr Patterns 2, 93-97; Hayashi et al. 2003 Genesis 37, 51-53.) Bi-allelic, gene-edited Dkk3$^{deltaCFP/CFP}$ offspring were recovered by crossing Dkk3$^{deltaCFP/+}$ to a Dkk3$^{CFP/+}$ (FIG. 18) confirming that embryonic lethality resulted directly from the loss of DKK3b expression rather than by a tightly linked cis gene defect(s).

Ex vivo gene editing of Dkk3$^{CFP/+}$ mouse embryonic fibroblasts (MEFs) confirmed the selective disruption of Dkk3b expression. A second round of ZFN-initiated, HR repair introduced a mCherry reporter into the wild type Dkk3 allele of the Dkk3$^{CFP/+}$ MEF generating bi-allelic mutations at the TSS2 Dkk3 locus with cells expressing both CFP and mCherry. FACS isolated Dkk3$^{CFP/mcherry}$ MEFs expressed the ~65 kDa glycosylated DKK3 protein but lacked the 30 kDa DKK3B (FIG. 19a). Exon-specific qPCR confirmed expression of the secreted Dkk3 transcript and the selective loss of the Dkk3b transcript (FIG. 19b). Examination of β-catenin dependent c-Myc and cyclin D1 expression in the DKK3b deficient Dkk3$^{CFP/mCherry}$ cells showed a 88-fold increase in c-Myc mRNA and a 160 fold increase in CyclinD1 mRNA (FIG. 19c). These data confirm that the gene-editing strategy (i) selectively eliminated expression of the intracellular DKK3b; (ii) preserved expression of the secreted DKK3; and (iii) resulted in dramatic increases in β-catenin dependent gene expression. To distinguish this unique intracellular gene product of the Dkk3 locus from its secreted form (DKK3) and recognize its functional impact on the β-catenin pathway, this protein is given the name of Inhibitor of β-catenin Signaling (IBS).

IBS Modulates β-Catenin Signaling

The relationship between IBS and the Wnt/β-catenin signaling pathway was defined by cell proliferation, promoter-driven reporter assays, and cell migration analysis. Limited antibiotic induction of Tet-inducible IBS or DKK3 constructs was used to avoid the untoward effects of overexpression. IBS arrested PC3 cell proliferation (FIG. 8a) at the G0/G1 phase of the cell cycle (FIG. 8b) and led to the near complete loss of IBS expressing cells by 24-36 h of induction (FIG. 8a). Unlike prior over-expression studies, controlled DKK3 expression did not alter the rate of PC3 cell proliferation (FIG. 8a,b). (Veeck et al. 2012 Biochim Biophys Acta 1825, 18-28; Hsieh et al. 2004 Oncogene 23, 9183-9189; Abarzua et al 2005 Cancer Res 65, 9617-9622; Edamura et al. 2007 Cancer Gene Ther 14, 765-772.)

Over-expression of DKK3 in cancer cells initiates c-Jun Kinase (JNK) mediated apoptosis. (Abarzua et al. 2005 Cancer Res 65, 9617-9622; Kawasaki et al. 2009 Cancer Gene Ther 16, 65-72.) IBS and the JNK inhibitor, TAT-JBD were introduced into PC3 cells as TAT-fusion protein and peptide, respectively, and cell proliferation was measured after 3 days. (Pain et al. 2008 Toxicology 243, 124-137.) TAT-IBS arrested proliferation and resulted in the loss of >75% the initial cell population (FIG. 8c), whereas addition of the JNK inhibitor with TAT-IBS prevented cell loss without altering IBS-induced proliferation arrest (FIG. 8c). Pro-apoptotic levels of cleaved Caspase 3 increased in TAT-IBS treated cells and this increase was blocked by inhibition of JNK activity (FIG. 8d). These data demonstrate that IBS has the anti-proliferative and pro-apoptotic activities previously associated with the Dkk3 locus. (Veeck et al. 2012 Biochim Biophys Acta 1825, 18-28; Abarzua et al. 2005 Cancer Res 65, 9617-9622.)

The impact of IBS on basal and Wnt stimulated cell proliferation was then examined in immortalized HEK293 cells (FIG. 9a). Basal cell proliferation was unaffected by IBS, while Wnt-stimulated cell proliferation during the 3 day experimental period was slowed progressively in cells transiently transfected with increasing quantities of IBS (FIG. 9b). The more robust silencing by TAT-IBS is likely due to the universal delivery of this regulator to the cell monolayer. At the highest concentration tested, TAT-IBS completely eliminated Wnt-stimulated cell proliferation without altering basal cell proliferation (FIG. 9b).

Primary and downstream promoter-luciferase reporter assays were used to explore the interaction between IBS and β-catenin-driven gene expression. Cells were co-transfected with Wnt1 and promoter-driven luciferase constructs and treated with TAT-IBS for 24 h. Wnt stimulated a 65-fold increase in Tcf-luciferase levels and TAT-IBS completely arrested expression of this canonical β-catenin reporter (FIG. 9c). The ability of IBS to modulate two downstream β-catenin modulated pathways that reduce cell adhesion (ECad) and promote cell cycle progression (E2F) was also examined. Wnt silenced E-Cad promoter activity by 90% and IBS reversed Wnt-dependent silencing and restored promoter activity to basal levels (FIG. 9c). (Jamora et al. 2003 Nature 422, 317-322; Li et al. 2007 Oncogene 26, 6194-6202.) Similarly, Wnt increased E2F-promoter activity 6-fold and IBS reduced E2F-promoter to baseline (FIG. 9c). Motile MDA-MB-231 cells were used to examine the effect of IBS on β-catenin dependent cell migration. IBS slowed malignant cell migration by >60% (FIG. 9d). Taken together, these data show that IBS modulates multiple aspects of β-catenin signaling.

IBS Blocks Nuclear Translocation of β-Catenin

Ex vivo studies done with malignant cells provided key clues to the molecular mechanism of IBS action. Overexpression of DKK3 decreased nuclear associated β-catenin, and yeast two-hybrid screens found that DKK3 interacted with cytoplasmic βTrCP, the E3 ubiquitin-protein ligase subunit that binds β-catenin. (Lee et al. 2009 Int j Cancer 124, 287-297; Yue et al. 2008 Carcinogenesis 29, 84-92.) Prior to the discovery of intracellular IBS, DKK3 effectors capable of forming cytoplasmic complexes that affect β-catenin trafficking were unknown.

Co-precipitation studies were done using exogenous, epitope-tagged IBS, βTrCP and the constitutively active S33Y mutant of β-catenin (FIG. 10a). Both βTrCP and IBS co-precipitated with Flag-$^{S33Y}$β-catenin, while control IgG precipitates lacked the epitope tagged targets (FIG. 10b). Myc-βTrCP immune precipitates also contained $^{S33Y}$β-catenin and IBS, and HA-IBS immune precipitates contained $^{S33Y}$β-catenin, and βTrCP (FIG. 10a). When only two of the three partners were expressed in HEK293 cells, no interactions were observed (FIG. 10b-d). In HA-IBS expressing cells, anti-HA immune complexes precipitated native, unphosphorylated β-catenin, but not phosphorylated β-catenin or GSK3 indicating that IBS was not a component of the destruction complex (FIG. 10e) and that the β-catenin destined for nuclear import interacted with the IBS:βTrCP complex.

The biological consequence of the IBS:βTrCP:β-catenin complex on nuclear β-catenin levels was evaluated in SOAS-2 and HeLa cells lacking native IBS. (Niehrs 2006 Oncogene 25, 7469-7481; Sato et al. 2007 Carcinogenesis 28, 2459-2466.) Cells were stimulated with the GSK3 inhibitor, LiCl, and cell lysates separated into nuclear, cytosolic and microfilament fractions. LiCl stimulation led to the expected accumulation of β-catenin in the cytoplasm and the nucleus (FIG. 10f). Short-term IBS replacement resulted in a nearly 3-fold increase total cell content of β-catenin, reduced both the cytoplasmic and nuclear levels and redistributed β-catenin to the microfilaments (FIG. 10d). IBS has no impact on the organization of the actin cytoskeleton in SOAS-2 cells. IBS-dependent loss of nuclear β-catenin was rapid beginning within 30 min of IBS replacement, and reaching maximal suppression by 60 min. IBS-suppressed nuclear β-catenin levels remained at ~⅓ of that in untreated controls for 3 h (FIG. 10g). Thus, the inhibitory complex formed between IBS:βTrCP and unphosphorylated β-catenin interrupts the nuclear import and defines the molecular basis for the silencing of β-catenin signaling by IBS.

Generalization of the Secreted ScpIBS

Initial work was based on the use of the SRP-cp "borrowed" from the secreted PTEN protein. In the more general case, we realized that any Secretion Recognition Peptide domain that engages the SRP receptor (translocon) in the ER membrane required to move the growing polypeptide chain across the ER membrane for secretion. In addition, we recognized that a cell penetration domain—a polycationic α-helix—necessary to "attach" the fusion protein to the cell surface by electrostatic interactions could be generalized. In addition, we included a purification epitope tag—6 his (SEQ ID NO: 3)—and a FLAG epitope that doubles as an enzyme cleavage site to remove these purification aids. The general organization of the ScpIBS is graphically shown in FIG. 20.

Proof-of-principle was done using the the SRP from Azurocidin (a cationic antimicrobial protein CAP37 or heparin-binding protein (HBP), and the MTD cell penetrating domain in the lab.

The data show results of a TOPFLASH assay. TOPFLASH reporter cells were treated with conditioned media from CHO cells expressing the three different secreted ScpIBS for 16 h in the presence of LiCl. Data are the means±SE for 8 replicates.

The schematic in FIG. 21 represents the accumulated mutation/deletion/truncation evaluation of the essential domains of the IBS protein. All mutations/deletions/truncations were inserted into the pcDNA3 expression vector as a co-cistronic construct with either mCherry or GFP attached to the N-terminus as an auto-cleavable reporter by a T2A element. When transiently transfected in the TOPFLASH reporter cells a nuclear localized fluorescent protein and a cytoplasmic IBS mutant is produced from a single transcript. The two proteins separate during translation.

The IBS molecule has 4 distinct functional domains.

A 20 residue long N-terminus that is required for function.

A N1 50 residue long, cysteine rich domain required for function.

A C1 ~70 residue long, cysteine rich domain can be eliminated without altering function. A 20 residue long C-terminus required for function.

The chart maps the domain in boxes, cysteine residues as black, green or white bars, putative disulfide bridging shown by connectors and negatively charged key residues at the N- and C-termini shown in red.

N1 Cys mutants had selected cysteine residues mutated to either Alanine or Aspartic Acid. Disulfide bridging was eliminated without affecting silencing of beta catenin signaling.
E-G Mutant The three glutamic acid mutants at the extreme N-terminus were mutated to glycines. This inactivated the IBS molecule.
N-Term Mutant
Elimination of the 20 residue N-terminus inactivated the IBS molecule.

Retention of the N-terminal 20 residues, but elimination of the next 50 residues (21-71) had no effect on IBS silencing of beta catenin signaling.
C-Term Mutant Elimination of the last 20 residues of IBS inactivated the protein.

Elimination of residues 125-260 containing the C1 domain had no effect on IBS silencing of beta catenin signaling.
Nterm/Cterm Deletion A mutant IBS composed of the N-terminal 20 residues the N1 domain and the C-terminal 20 residues had the same TOPFLASH silencing activity as the full length IBS.
Comparison of the Impact of the N-1 Domain of the DKK Family on β-Catenin Signaling The N-1 domain of IBS is the critical domain required for silencing of β-catenin signaling. Alignment of the N-1 domains of all DKK family members revealed considerable organizational conservation raising the possibility that this domain in all family members may function like that of IBS. To evaluate the impact of the N-1 domains of the DKK family on IBS function, the N-1 domains of DKK1, DKK2 and DKK4 were exchanged with the N-1 domain of IBS (DKK3b) and expressed in HEK293T TopFlash reporter cells as co-cystronic GFP-T2A-IBS by transient transfection. The impact of the domain substitutions on IBS silencing of β-catenin signaling was evaluated in LiCl stimulated reporter cells. Data are reported mean±SE of triplicates of 5 independent transfections. (See FIG. 22.)

Any appropriate route of administration can be employed, for example, parenteral, intravenous, subcutaneous, intramuscular, intraventricular, intracorporeal, intraperitoneal, rectal, or oral administration. Most suitable means of administration for a particular patient will depend on the nature and severity of the disease or condition being treated or the nature of the therapy being used and on the nature of the active compound.

Solid dosage forms for oral administration include capsules, tablets, pills, powders, and granules. In such solid dosage forms, the compounds described herein or derivatives thereof are admixed with at least one inert customary excipient (or carrier) such as sodium citrate or dicalcium phosphate or (i) fillers or extenders, as for example, starches, lactose, sucrose, glucose, mannitol, and silicic acid, (ii) binders, as for example, carboxymethylcellulose, alignates, gelatin, polyvinylpyrrolidone, sucrose, and acacia, (iii) humectants, as for example, glycerol, (iv) disintegrating agents, as for example, agar-agar, calcium carbonate, potato or tapioca starch, alginic acid, certain complex silicates, and sodium carbonate, (v) solution retarders, as for example, paraffin, (vi) absorption accelerators, as for example, quaternary ammonium compounds, (vii) wetting agents, as for example, cetyl alcohol, and glycerol monostearate, (viii) adsorbents, as for example, kaolin and bentonite, and (ix) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents. Solid compositions of a similar type may also be employed as fillers in soft and hard-filled gelatin capsules using such excipients as lactose or milk sugar as well as high molecular weight polyethyleneglycols, and the like. Solid dosage forms such as tablets, dragees, capsules, pills, and granules can be prepared with coatings and shells, such as enteric coatings and others known in the art.

Liquid dosage forms for oral administration include pharmaceutically acceptable emulsions, solutions, suspensions, syrups, and elixirs. In addition to the active compounds, the liquid dosage forms may contain inert diluents commonly used in the art, such as water or other solvents, solubilizing agents, and emulsifiers, such as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil, sesame oil, glycerol, tetrahydrofurfuryl alcohol, polyethyleneglycols, and fatty acid esters of sorbitan, or mixtures of these substances, and the like. Besides such inert diluents, the composition can also include additional agents, such as wetting, emulsifying, suspending, sweetening, flavoring, or perfuming agents.

Materials, compositions, and components disclosed herein can be used for, can be used in conjunction with, can be used in preparation for, or are products of the disclosed methods and compositions. It is understood that when combinations, subsets, interactions, groups, etc. of these materials are disclosed that while specific reference of each various individual and collective combinations and permutations of these compounds may not be explicitly disclosed, each is specifically contemplated and described herein. For example, if a method is disclosed and discussed and a number of modifications that can be made to a number of molecules including in the method are discussed, each and every combination and permutation of the method, and the modifications that are possible are specifically contemplated unless specifically indicated to the contrary. Likewise, any subset or combination of these is also specifically contemplated and disclosed. This concept applies to all aspects of this disclosure including, but not limited to, steps in methods using the disclosed compositions. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed.

Certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

Isomeric mixtures containing any of a variety of isomer ratios may be utilized in accordance with the present invention. For example, where only two isomers are combined, mixtures containing 50:50, 60:40, 70:30, 80:20, 90:10, 95:5, 96:4, 97:3, 98:2, 99:1, or 100:0 isomer ratios are contemplated by the present invention. Those of ordinary skill in the art will readily appreciate that analogous ratios are contemplated for more complex isomer mixtures.

If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic methods well known in the art, and subsequent recovery of the pure enantiomers.

Applicant's disclosure is described herein in preferred embodiments with reference to the Figures, in which like numbers represent the same or similar elements. Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

The described features, structures, or characteristics of Applicant's disclosure may be combined in any suitable manner in one or more embodiments. In the following description, numerous specific details are recited to provide a thorough understanding of embodiments of the invention. One skilled in the relevant art will recognize, however, that Applicant's composition and/or method may be practiced without one or more of the specific details, or with other methods, components, materials, and so forth. In other instances, well-known structures, materials, or operations are not shown or described in detail to avoid obscuring aspects of the disclosure.

In this specification and the appended claims, the singular forms "a," "an," and "the" include plural reference, unless the context clearly dictates otherwise.

Unless defined otherwise, all technical and scientific terms used herein have the same meaning as commonly understood by one of ordinary skill in the art. Although any methods and materials similar or equivalent to those described herein can also be used in the practice or testing of the present disclosure, the preferred methods and materials are now described. Methods recited herein may be carried out in any order that is logically possible, in addition to a particular order disclosed.

INCORPORATION BY REFERENCE

References and citations to other documents, such as patents, patent applications, patent publications, journals, books, papers, web contents, have been made in this disclosure. All such documents are hereby incorporated herein by reference in their entirety for all purposes. Any material, or portion thereof, that is said to be incorporated by reference herein, but which conflicts with existing definitions, statements, or other disclosure material explicitly set forth herein is only incorporated to the extent that no conflict arises between that incorporated material and the present disclosure material. In the event of a conflict, the conflict is to be resolved in favor of the present disclosure as the preferred disclosure.

EQUIVALENTS

The representative examples are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples and the references to the scientific and patent literature included herein. The examples contain important additional information, exemplification and guidance that can be adapted to the practice of this invention in its various embodiments and equivalents thereof.

What is claimed is:

1. A variant of human Dickkopf-3b (DKK3b) comprising:
   (i) amino acids 1-20 of the N-terminus of human DKK3b;
   (ii) the N-terminal cysteine rich domain of human DKK3b; and
   (iii) the C-terminus 20 amino acids of human DKK3b,
   wherein the variant is an inhibitor of β catenin signaling and wherein the variant does not comprise the C-terminal cysteine-rich domain of human DKK3b.

2. A fusion protein comprising the variant of claim 1.

3. The fusion protein of claim 2, comprising a cell penetrating (cp) domain fused to the N-terminus of the variant.

4. The fusion protein of claim 3, wherein the cp domain comprises a polycationic α-helix.

5. The fusion protein of claim 3, wherein the cp domain comprises polyarginine or TAT.

6. The fusion protein of claim 3, further comprising a signal recognition peptide (SRP) domain fused to the N-terminus of the cp domain.

7. The fusion protein of claim 6, wherein the SRP domain comprises an SRP domain of any secretory protein that engages the SRP receptor in the endoplasmic reticulum (ER) membrane.

8. The fusion protein of claim 7, wherein the SRP domain comprises the SRP domain of human phosphatase and tensin homolog (PTEN).

9. The fusion protein of claim 7, wherein the SRP domain comprises the N-terminal 62 amino acids of the human PTEN protein.

10. The fusion protein of claim 7, wherein the SRP domain comprises the SRP from azuricidin or heparin binding protein.

11. The variant of claim 1, wherein at least one cysteine residue in the N1 domain is mutated to alanine or glutamic acid.

12. A nucleic acid encoding the variant of claim 1.

13. A host cell transformed with an expression vector comprising a nucleic acid of claim 12.

14. The host cell of claim 13, selected from a bacterial host cell, a viral host cell or a mammalian host cell.

15. The host cell of claim 14, wherein the host cell is a Chinese Hamster ovary (CHO) cell.

16. A pharmaceutical composition comprising the variant of claim 1 and an excipient or diluent.

17. A method of inhibiting β-catenin signaling in a subject, comprising administering to the subject a pharmaceutical composition of claim 16.

18. The method of claim 17, wherein the subject is suffering from cancer.

19. The method of claim 18, further comprising administering a anti-tumor agent other than the variant.

20. The variant of claim 1, wherein the variant does not comprise amino acids 21-71 of human DKK3b.

* * * * *